United States Patent [19]

Jungheim et al.

[11] Patent Number: 5,461,154

[45] Date of Patent: Oct. 24, 1995

[54] INTERMEDIATE AND PROCESS FOR MAKING

[75] Inventors: Louis N. Jungheim, Indianapolis; Timothy A. Shepherd, Indiana, both of Ind.

[73] Assignee: Eli Lilly and Company, Indianapolis, Ind.

[21] Appl. No.: 190,630

[22] Filed: Feb. 2, 1994

[51] Int. Cl.$^6$ ............ C07D 401/00; C07D 403/00
[52] U.S. Cl. ............ 544/360; 544/364; 544/372; 544/390; 514/252
[58] Field of Search ............ 544/360, 364, 544/372, 390; 514/252

[56] References Cited

U.S. PATENT DOCUMENTS 4,191,765  3/1980  Fritsch et al. ............ 544/401

OTHER PUBLICATIONS

Ornstein et al, Bioorg. Med. Chem. Lett (1993), 3(1), 43–8. Chem. Abst. 118–213469 (1993).

Ziegler et al, J. Med. Chem. (1990), 33(1), 142–6 Chem. Abst. 112–35810 (1990).

*Primary Examiner*—Cecilia Tsang
*Attorney, Agent, or Firm*—Janet T. McClain; Gerald V. Dahling

[57] ABSTRACT

The present invention provides novel HIV protease inhibitors, pharmaceutical formulations containing those compounds and methods of treating and/or preventing HIV infection and/or AIDS.

1 Claim, No Drawings

INTERMEDIATE AND PROCESS FOR MAKING

BACKGROUND OF THE INVENTION

A retrovirus designated human immuno-deficiency virus (HIV) is the causative agent of the complex disease termed Acquired Immune Deficiency Syndrome (AIDS), and is a member of the lentivirus family of retroviruses. M. A. Gonda, F. Wong-Staal, R. C. Gallo, "Sequence Homology and Morphological Similarity of HTLV III And Visna Virus, A Pathogenic Lentivirus", Science, 227, 173, (1985); P. Sonigo, N. Alizon, et al., "Nucleotide Sequence of the Visna Lentivirus: Relationship to the AIDS Virus", Cell, 42, 369, (1985). The complex disease AIDS includes progressive destruction of the immune system and degeneration of the central and peripheral nervous systems. The HIV virus was previously known or referred to as LAV, HTLV-III or ARV.

A common feature of retrovirus replication is the post-translational processing of precursor polyproteins by a virally encoded protease to generate mature viral proteins required for viral assembly and function. Interruption of this processing appears to prevent the production of normally infectious virus. Unprocessed structural proteins also have been observed in clones of non-infectious HIV strains isolated from human patients. The results suggest that the inhibition of HIV protease represents a viable method for the treatment or prevention of AIDS and/or the treatment or prevention of infection by HIV.

The HIV genome encodes structural protein precursors known as gag and pol, which are processed to afford the protease, reverse transcriptase and endonuclease/integrase. The protease further cleaves gag and gag-pol polyproteins to yield mature structural proteins of the virus core.

Considerable efforts are being directed toward the control of HIV by means of the structural protein precursors which are processed to yield the retroviral protease, reverse transcriptase and endonuclease/integrase. For example, a currently used therapeutic, AZT, is an inhibitor of the viral reverse transcriptase. H. Mitsuya, N. S. Broder, "Inhibition of the In Vitro Infectivity in Cytopathic Effects of HTLV III", Proc. Natl. Acad. Sci. USA, 83, 1911 (1986).

Research efforts have also been directed toward HIV protease inhibitors. For example, European Patent Application (EPA) 361 341; EPA 346 847; EPA 402 646; and EPA 337 714 all disclose compounds which are said to be useful as HIV protease inhibitors.

Unfortunately, many of the known HIV protease inhibitors suffer from toxicity problems, lack of bioavailability or short in vivo half-lives. In particular, it is believed that oral bioavailability is a necessary characteristic of an HIV protease inhibitor due to the chronic nature of the disease. However, peptides and peptide mimetics are notorious for their inability to be orally absorbed. Thus, despite the recognized therapeutic potential associated with a protease inhibitor and the research efforts expended thus far, a viable therapeutic agent has not yet emerged.

Accordingly, a primary object of the present invention is to provide novel HIV protease inhibitors which are useful in the treatment or prevention of HIV infection and/or the resulting acquired immune deficiency syndrome (AIDS).

A further object of the present invention is to provide therapeutic compositions that are of value in the treatment or prevention of HIV infection and/or the treatment or prevention of AIDS.

Still another object is to provide methods for the treatment or prevention of HIV infection and/or AIDS.

Other objects, features and advantages will become apparent to those skilled in the art from the following description and claims.

SUMMARY OF THE INVENTION

The present invention relates to compounds of formula I, below, and pharmaceutically acceptable salts thereof that inhibit the protease encoded by human immunodeficiency virus (HIV) type 1 (HIV-1) or type 2 (HIV-2). These compounds are useful in the treatment or prevention of inflection by HIV and the treatment or prevention of the resulting acquired immune deficiency syndrome (AIDS). The compounds, their pharmaceutically acceptable salts, and the pharmaceutical compositions of the present invention can be used alone or in combination with other antivirals, immunomodulators, antibiotics or vaccines. Methods of treating or preventing AIDS, methods of treating or preventing HIV infection and methods of inhibiting HIV replication are disclosed.

The present invention relates to a method for inhibiting HIV replication in an HIV infected cell, a cell susceptible to HIV infection or a primate in need thereof, thus treating or preventing HIV infection and/or AIDS, comprising administering an effective amount of a compound of formula I

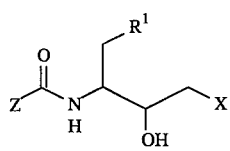

wherein:

Z is a group having the structure:

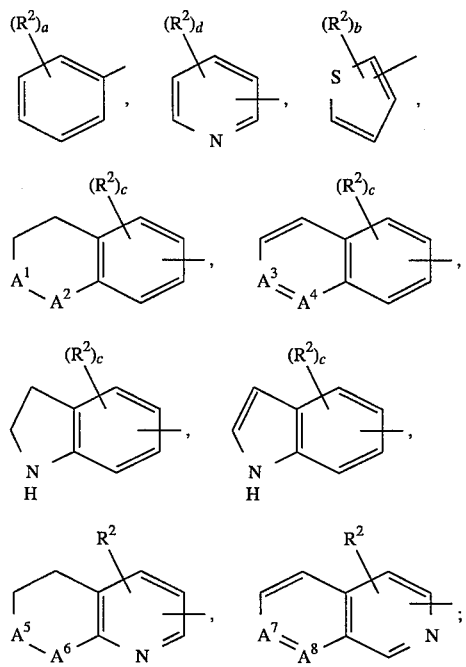

where:

a is 1, 2, 3, 4, or 5;

b is 1, or 2;

c is 1, or 2;

d is 1, 2, 3, or 4;

each $R^2$ is independently hydrogen, hydroxy, thiol, halo, amino, $C_1$–$C_4$ alkylamino, di($C_1$–$C_4$)alkylamino, nitro, carboxy, $C_1$–$C_6$ alkyl, $C_1$–$C_6$ alkoxy, $C_1$–$C_6$ alkylthio, halo($C_1$–$C_4$)alkyl, hydroxy($C_1$–$C_4$)alkyl, $C_1$–$C_6$ alkylthio ($C_1$–$C_6$)alkyl, $C_1$–$C_4$ alkoxycarbonyl, carbamoyl, N-($C_1$–$C_4$)alkylcarbamoyl, $C_1$–$C_4$ alkylsulfonyl, N,N-di($C_1$–$C_4$)alkylcarbamoyl, or $C_1$–$C_4$ alkylsulfonylamino;

$A^1$ and $A^2$ are independently —$CH_2$— or —$N(R^8)$—;

$A^3$ and $A^4$ are independently —CH— or —N—;

$A^5$ and $A^6$ are independently —$CH_2$— or —$N(R^9)$—;

$A^7$ and $A^8$ are independently —CH— or —N—;

$R^8$ is hydrogen or $C_1$–$C_4$ alkyl;

$R^9$ is hydrogen or $C_1$–$C_4$ alkyl;

$R^1$ is aryl, or —S-aryl;

X is a group having the structure:

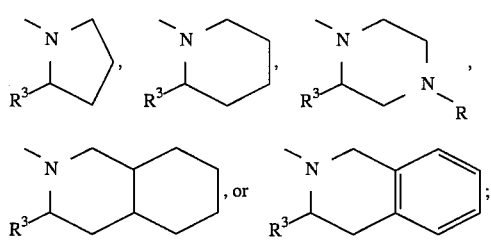

where:

R is hydrogen, $C_1$–$C_4$ alkyl, or —$CH_2$-pyridyl;

$R^3$ is a group having the structure:

1) —C(O)—$NR^4R^4$,

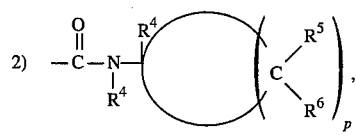

or

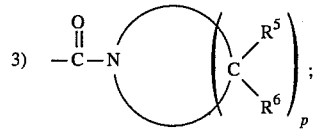

p is 4 or 5;

$R^4$ at each occurrence is independently hydrogen, $C_1$–$C_6$ alkyl or hydroxy ($C_1$–$C_4$)alkyl; and $R^5$ and $R^6$ are independently selected from hydrogen, hydroxy, $C_1$–$C_6$ alkyl, $C_1$–$C_6$ alkoxy, or hydroxy($C_1$–$C_4$)alkyl; with the provisos that:

(1) one of $A^1$ and $A^2$ must be —$N(R^8)$—;

(2) $A^1$ and $A^2$ cannot both be —$N(R^8)$—;

(3) $A^3$ and $A^4$ cannot both be —N—;

(4) one of $A^5$ and $A^6$ must be —$N(R^9)$—;

(5) $A^5$ and $A^6$ cannot both be —$N(R^9)$—;

(6) $A^7$ and $A^8$ cannot both be —N—;

or a pharmaceutically acceptable salt thereof.

The present invention also relates to a compound of formula I, or a pharmaceutically acceptable salt thereof, wherein $R^1$, Z and X are as defined above in formula I.

The present invention further provides pharmaceutical formulations comprising a compound of formula I or a pharmaceutically acceptable salt thereof, in combination with a pharmaceutically acceptable carrier, diluent or excipient therefor.

The present invention further provides a process for producing a compound of formula II

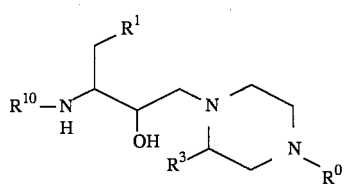

wherein:

$R^1$ is aryl, or —S-aryl;

$R^{10}$ is hydrogen or an amino-protecting group;

$R^0$ is $C_1$–$C_4$ alkyl or —$CH_2$-pyridyl;

$R^3$ is a group having the structure:

1) —C(O)—$NR^4R^4$,

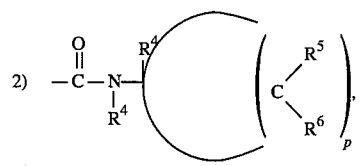

or

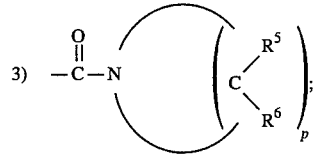

p is 4 or 5;

$R^4$ at each occurrence is independently hydrogen, $C_1$–$C_6$ alkyl or hydroxy($C_1$–$C_4$)alkyl; and $R^5$ and $R^6$ are independently selected from hydrogen, hydroxy, $C_1$–$C_6$ alkyl, $C_1$–$C_6$ alkoxy, or hydroxy ($C_1$–$C_4$)alkyl;

or a pharmaceutically acceptable salt thereof; comprising:

(a) reducing a compound of the formula

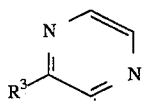

provide a piperazine compound;

(b) alkylating the piperazine compound to provide a compound of the formula

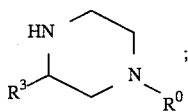

and then (c) reacting the piperazine compound of step (b) with an epoxide of the formula

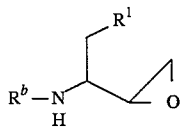

where $R^b$ is an amino protecting group; in an alcoholic solvent at a temperature of from about 20° C. to 100° C. to form a compound of formula II wherein $R^{10}$ is an amino-protecting group; and d) optionally removing the amino-protecting group to form a compound of formula II wherein $R^{10}$ is hydrogen.

The present invention also provides a useful intermediate of formula II

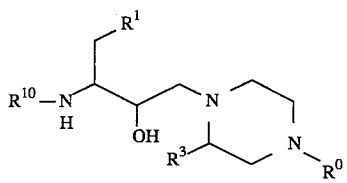

wherein:

$R^1$ is aryl, or —S-aryl;

$R^{10}$ is hydrogen or an amino-protecting group;

$R^0$ is $C_1$–$C_4$ alkyl or —$CH_2$-pyridyl;

$R^3$ is a group having the structure:

1) —C(O)—$NR^4R^4$,

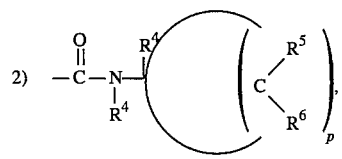

or

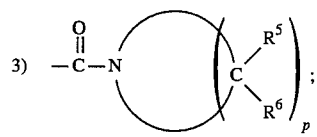

p is 4 or 5;

$R^4$ at each occurrence is independently hydrogen, $C_1$–$C_6$ alkyl or hydroxy($C_1$–$C_4$)alkyl; and $R^5$ and $R^6$ are independently selected from hydrogen, hydroxy, $C_1$–$C_6$ alkyl, $C_1$–$C_6$ alkoxy, or hydroxy($C_1$–$C_4$)alkyl;

or a pharmaceutically acceptable salt thereof.

DETAILED DESCRIPTION OF THE INVENTION

The present invention provides new compounds of formula I, as described above, that are useful for treating and/or preventing HIV infection and/or AIDS.

All temperatures stated herein are in degrees Celsius (°C.). All units of measurement employed herein are in weight units except for liquids which are in volume units.

The term "$C_1$–$C_6$ alkyl" represents a straight or branched alkyl chain having from one to six carbon atoms. Typical $C_1$–$C_6$ alkyl groups include methyl, ethyl, propyl, isopropyl, butyl, isobutyl, sec-butyl, t-butyl, pentyl, neo-pentyl, hexyl, and the like. The term "$C_1$–$C_6$ alkyl" includes within its definition the term "$C_1$–$C_4$ alkyl".

The term "halo" represents chloro, fluoro, bromo or iodo.

The term "halo($C_1$–$C_4$)alkyl" represents a straight or branched alkyl chain having from one to four carbon atoms with 1–3 halogen atoms attached to it. Typical halo($C_1$–$C_4$)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl, and the like.

The term "hydroxy($C_1$–$C_4$)alkyl" represents a straight or branched alkyl chain having from one to four carbon atoms with a hydroxy group attached to it. Typical hydroxy($C_1$–$C_4$)alkyl groups include hydroxymethyl, 2-hydroxyethyl, 3-hydroxypropyl, 2-hydroxyisopropyl, 4-hydroxybutyl, and the like.

The term "$C_1$–$C_6$ alkylthio" represents a straight or branched alkyl chain having from one to six carbon atoms attached to a sulfur atom. Typical $C_1$–$C_6$ alkylthio groups include methylthio, ethylthio, propylthio, isopropylthio, butylthio, sec-butylthio, t-butylthio, pentylthio, hexylthio, and the like.

The term "$C_1$–$C_4$ alkylamino" represents a straight or branched alkyl chain having from one to four carbon atoms attached to an amino group. Typical $C_1$–$C_4$ alkylamino groups include methylamino, ethylamino, propylamino, isopropylamino, butylamino, sec-butylamino, and the like.

The term "di($C_1$–$C_4$)alkylamino" represents two straight or branched alkyl chains, each having from one to four carbon atoms attached to a common amino group. Typical di($C_1$–$C_4$)alkylamino groups include dimethylamino, ethylmethylamino, methylpropylamino, ethylisopropylamino, butylmethylamino, sec-butylethylamino, and the like.

The term "$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, sec-butoxy, t-butoxy, pentoxy, hexoxy, and the like. The term "$C_1$–$C_6$ alkoxy" includes within its definition the term "$C_1$–$C_4$ alkoxy".

The term "$C_1$–$C_4$ alkoxycarbonyl" represents a straight or branched alkoxy chain having from one to four carbon atoms attached to a carbonyl moiety. Typical $C_1$–$C_4$ alkoxycarbonyl groups include methoxycarbonyl, ethoxycarbonyl, propoxycarbonyl, isopropoxycarbonyl, butoxycarbonyl, and the like.

The term "N-($C_1$–$C_4$)alkylcarbamoyl" represents a straight or branched alkyl chain having from one to four carbon atoms attached to the nitrogen atom of a carbamoyl moiety. Typical N-($C_1$–$C_4$)alkylcarbamoyl groups include N-methylcarbamoyl, N-ethylcarbamoyl, N-propylcarbamoyl, N-isopropylcarbamoyl, N-butylcarbamoyl, and N-t-butylcarbamoyl, and the like.

The term "N,N-di($C_1$–$C_4$)alkylcarbamoyl" represents two straight or branched alkyl chains, each having from one to four carbon atoms attached to the nitrogen atom of a carbamoyl moiety. Typical N,N-di($C_1$–$C_4$)alkylcarbamoyl groups include N,N-dimethylcarbamoyl, N,N-ethylmethylcarbamoyl, N,N-methylpropylcarbamoyl, N,N-ethylisopropylcarbamoyl, N,N-butylmethylcarbamoyl, N,N-sec-butylethylcarbamoyl, and the like.

The term "$C_1$–$C_4$ alkylsulfonyl" represents a straight or branched alkyl chain having from one to four carbon atoms attached to a sulfonyl moiety. Typical $C_1$–$C_4$ alkylsulfonyl groups include methylsulfonyl, ethylsulfonyl, propylsulfonyl, isopropylsulfonyl, butylsulfonyl, sec-butylsulfonyl, t-butylsulfonyl and the like.

The term "$C_1$–$C_4$ alkylsulfonylamino" represents a straight or branched alkyl chain having from one to four carbon atoms attached to a sulfonylamino moiety. Typical $C_1$–$C_4$ alkylsulfonylamino groups include methylsulfonylamino, ethylsulfonylamino, propylsulfonylamino, isopropylsulfonylamino, butylsulfonylamino, sec-butylsulfonylamino, t-butylsulfonylamino, and the like.

"Aryl" represents a phenyl or naphthyl ring which is optionally substituted with halo, hydroxy, or $C_1$–$C_4$ alkoxy.

The term "amino-protecting group" as used in the specification refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl; or urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxy-carbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; or benzoylmethylsulfonyl, 2-nitrophenylsulfenyl, diphenylphosphine oxide and like amino-protecting groups. The species of amino-protecting group employed is not critical so long as the derivatized amino group is stable to the condition of subsequent reaction(s) on other positions of the intermediate molecule and can be selectively removed at the appropriate point without disrupting the remainder of the molecule including any other amino-protecting group(s). Preferred amino-protecting groups are t-butoxycarbonyl (t-Boc) and benzyloxycarbonyl (CbZ). Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and sons, New York, N.Y., 1981, Chapter 7.

The compounds of the present invention have at least two asymmetric centers denoted by an asterisk in the formula below:

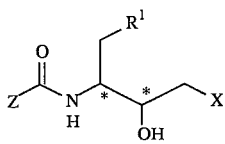

As a consequence of these asymmetric centers, the compounds of the present invention can occur as mixtures of diastereomers, racemic mixtures and as individual enantiomers. All asymmetric forms, individual isomers and combinations thereof, are within the scope of the present invention.

As mentioned above, the invention includes the pharmaceutically acceptable salts of the compounds defined by formula I. A compound of this invention may possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like.

Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

Preferred compounds of this invention are those compounds of formula I where:

Z is a group having the structure:

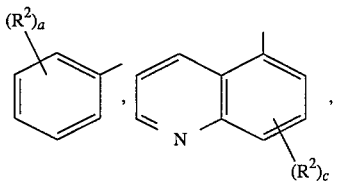

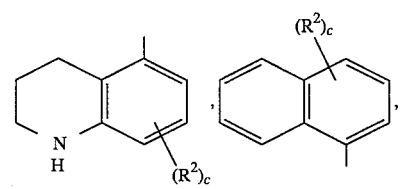

or

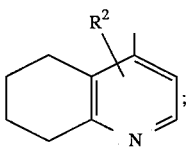

$R^2$ is hydrogen, hydroxy, $C_1$–$C_4$ alkyl, halo, amino, nitro, or trifluoromethyl;

a is 1, 2, or 3;

c is 1; and $R^3$ is —C(O)NR$^4$R$^4$; or a pharmaceutically acceptable salt thereof.

Of these preferred compounds, more preferred are those compounds where:

Z is

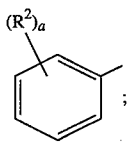

$R^2$ is hydrogen, methyl, ethyl, propyl, chloro, fluoro, hydroxy, or amino;

X is

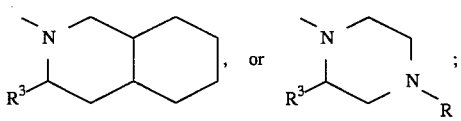

R is —CH$_2$-pyridyl;

$R^1$ is phenyl or —S-phenyl; and $R^3$ is —C(O)NH(R$^4$);

or a pharmaceutically acceptable salt thereof.

Of these preferred compounds, especially preferred are those compounds where:

Z is

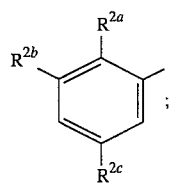

$R^{2a}$ is methyl, ethyl, or propyl;

$R^{2b}$ is hydrogen, hydroxy, or amino;

$R^{2c}$ is hydrogen, hydroxy, or amino;

X is

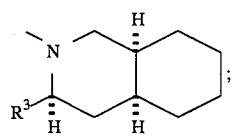

and $R^3$ is —C(O)NH(t-butyl);

or a pharmaceutically acceptable salt thereof.

The most preferred compounds are:

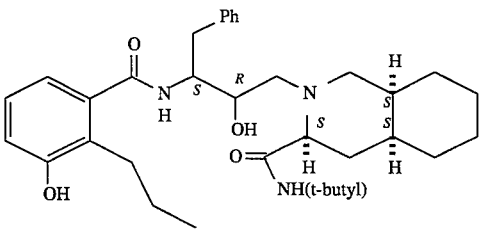

[3S-(3R*,4aR*,8aR*,2'S*,3'R*)]-2-[2'-hydroxy-3'-phenylmethyl-4'-aza-5'-oxo-5'-(2"-propyl-3"-hydroxyphenyl)pentyl] decahydroisoquinoline-3-N-t-butylcarboxamide;

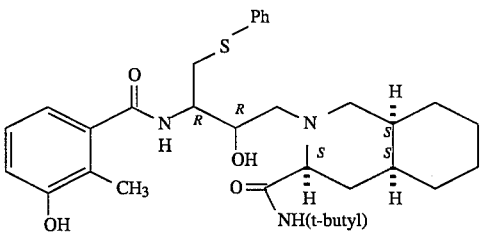

[3S-(3R*,4aR*,8aR*,2'S*,3'S*)]-2-[2'-hydroxy-3'-phenylthiomethyl-4'-aza-5'-oxo-5'-(2"-methyl-3"-hydroxyphenyl)pentyl] decahydroisoquinoline-3-N-t-butylcarboxamide;

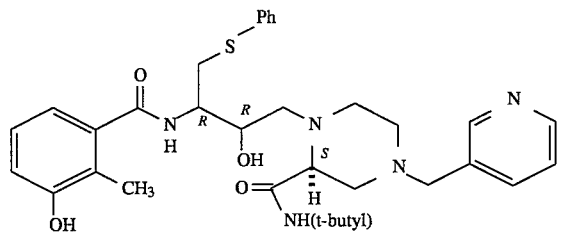

-continued

[2S-(2R*,2'S*,3'S*)]-1-[2'-hydroxy-3'-
phenylthiomethyl-4'-aza-5'oxo-5'-(3"-hydroxy-
2"-methylphenyl)pentyl]-4-pyrid-3"-ylmethyl
piperazine-2-N-t-butylcarboxamide;

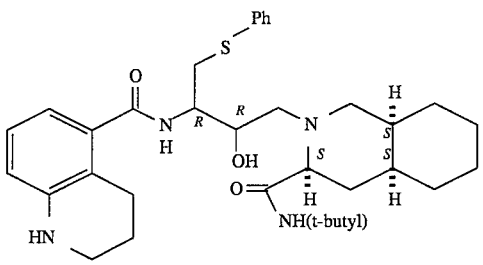

[3S-(3R*,4aR*,8aR*,2'S*,3'S*)]-2-[2'-hydroxy-3'-
phenylthiomethyl-4'-aza-5'-oxo-5'-(1",2",3",4"-
tetrahydroquinolin-5"-yl)pentyl]
decahydroisoquinoline-3-N-t-butylcarboxamide;

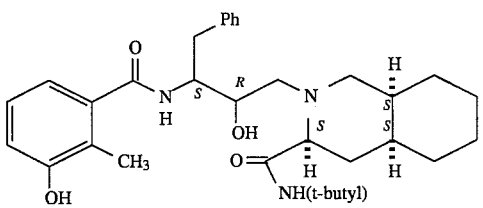

[3S-(3R*,4aR*,8aR*,2'S*,3'R*)]-2-[2'-hydroxy-3'-
phenylmethyl-4'-aza-5'-oxo-5'-(2"-methyl-3"-
hydroxyphenyl)pentyl] decahydroisoquinoline-3-
N-t-butylcarboxamide;

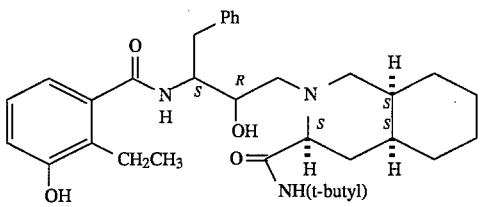

[3S-(3R*,4aR*,8aR*,2'S*,3'R*)]-2-[2'-hydroxy-3'-
phenylmethyl-4'-aza-5'-oxo-5'-(2"-ethyl-3"-
hydroxyphenyl)pentyl] decahydroisoquinoline-3-
N-t-butylcarboxamide;

or a pharmaceutically acceptable salt of any of the foregoing most preferred compounds.

The compounds of formula I can be prepared according to the following Reaction I.

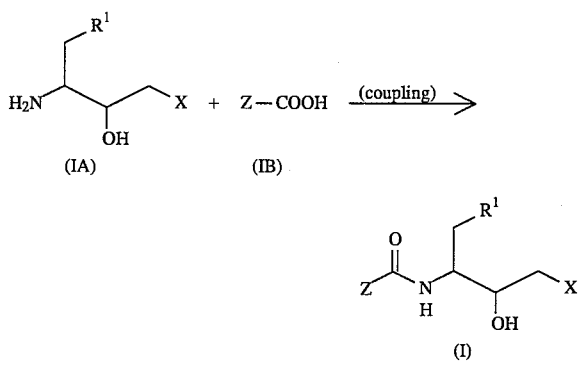

where $R^1$, X and Z are as defined for formula I above.

Reaction I is a standard coupling reaction commonly employed in the synthesis of amides which is carried out by reacting an appropriately substituted amine formula IA, with an appropriately substituted carboxylic acid reactant of formula IB, in an aprotic solvent or mixture of solvents. The reaction is carried out in the presence or absence of a promoting agent, preferably in the presence of a promoting agent, and in the presence of a coupling reagent. Typical aprotic solvents for this reaction are tetrahydrofuran and dimethylformamide, or a mixture of such solvents. The reaction is carried out at a temperature from about −30° C. to about 25° C. The amine reactant is generally employed in equimolar proportions relative to the carboxylic acid reactant, in the presence of an equimolar quantity to a slight excess of the coupling reagent. Typical coupling reagents include the carbodiimides such as dicyclohexylcarbodiimide (DCC) and N,N'-diethylcarbodiimide; the imidazoles such as carbonyldiimidazole; as well as reagents such as bis(2-oxo-3-oxazolidinyl)phosphinic chloride (BOP-Cl) or N-ethoxycarbonyl-2-ethoxy-1,2-dihydroquinoline (EEDQ). A preferred coupling reagent for this reaction is DCC. A promoting agent is preferably included for this reaction; a preferred promoting agent is hydroxybenzotriazole hydrate (HOBT.H₂O).

Once the reaction is complete, the compound may be isolated, if desired, by procedures known in the art, for example, the compound may be crystallized and then collected by filtration, or the reaction solvent may be removed by extraction, evaporation or decantation. The compound may be further purified, if desired, by common techniques such as crystallization or chromatography over solid supports such as silica gel or alumina.

The starting compounds of formula IA may be prepared according to the procedures shown in Reaction Scheme A.

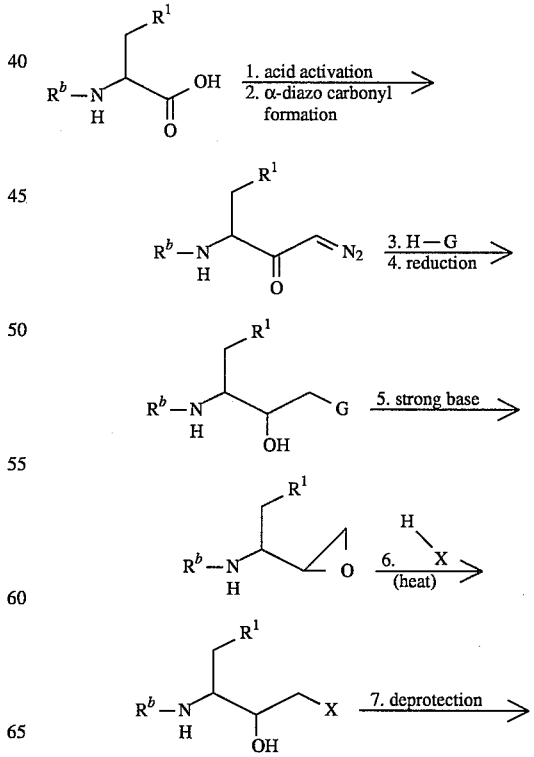

-continued
Reaction Scheme A

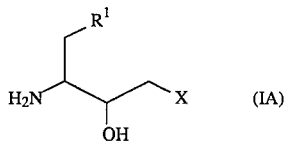

where:
R¹, and X are as defined above;
$R^b$ is an amino protecting group; and
G is halo.

Reaction Scheme A, above, is accomplished by carrying out reactions 1–7 in sequential order. Once a reaction is complete, the intermediate compound may be isolated, if desired, by procedures known in the art, for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

Reaction A.1 is carried out by activating, that is, converting, an amino-protected carboxylic acid reactant having the structure:

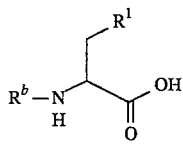

to the corresponding mixed anhydride under conditions known in the art. For example, the amino-protected carboxylic acid reactant may be reacted with a $C_1$–$C_6$ alkylchloroformate, such as isobutylchloroformate preferably in the presence of an acid scavenger. Preferred acid scavengers are the trialkylamines, preferably triethylamine. The reaction is typically carried out in an aprotic solvent such as ethyl acetate. Solvent choice is not critical so long as the solvent employed is inert to the ongoing reaction and the reactants are sufficiently solubilized to effect the desired reaction. The resulting mixed anhydride reactant is preferably used in Reaction A.2 without further isolation or purification.

Reaction A.2 is accomplished in two steps. First, a solution of sodium hydroxide, covered with a layer of an ether solvent, preferably diethylether, is reacted with a large excess of N-methyl-N-nitro-N-nitrosoguanidine to form a diazomethane reactant. The sodium hydroxide is preferably used as an aqueous solution having about four to six mol/liter of sodium hydroxide. Once this reaction is substantially complete, the organic layer is dried over a dessicant such as potassium hydroxide. This solution is then reacted with the mixed anhydride from Reaction A.1, above, to form the corresponding α-diazo carbonyl compound. The diazomethane reactant is preferably used in this reaction without isolation or purification. The reaction is typically carried out at a temperature of from about –50° C. to about –10° C., preferably about –20° C.

In Reaction A.3, the α-diazo carbonyl compound prepared in Reaction A.2 is reacted with an acid of the formula H-G where G is halo, in an aprotic solvent such as diethylether to form an α-halo carbonyl compound. A preferred acid reactant is hydrochloric acid which provides the corresponding α-chloro carbonyl compound. The reaction is typically carried out at a temperature from about –30° C. to about 0° C. Solvent choice is not critical so long as the solvent employed is inert to the ongoing reaction and the reactants are sufficiently solubilized to effect the desired reaction. The acid reactant is typically added in the form of an anhydrous gas in small increments until the reaction appears substantially complete. The reaction can be monitored by thin layer chromatography.

In Reaction A.4, the carbonyl moiety on the compound prepared in Reaction A.3 is reduced using standard conditions known in the art to form the corresponding α-chloro hydroxy compound. For example, the compound prepared in Reaction A.3 is combined with a reducing agent in a mixture of solvents. Typical reducing agents include sodium borohydride, lithium borohydride, zinc borohydride, diisobutylaluminum hydride, and sodium bis(2-methoxyethoxy)aluminum hydride. A preferred reducing agent is sodium borohydride. Typical solvent mixtures include a protic and aprotic mixture such as tetrahydrofuran/water. Solvent choice is not critical so long as the solvent employed is inert to the ongoing reaction and the reactants are sufficiently solubilized to effect the desired reaction. The reaction is typically carried out at a temperature from about –10° C. to about 10° C., preferably about 0° C.

In Reaction A.5, the α-chloro hydroxy compound prepared in Reaction A.4 is treated with a strong base to form the corresponding epoxide under standard conditions known in the art. For example, the α-chloro hydroxy compound may be reacted with a potassium hydroxide/ethanol mixture in an alcoholic solvent such as ethanol. The reaction is typically carried out at a temperature from about 0° C. to about the reflux temperature of the solvent. Preferably the reaction is carried out at room temperature.

In Reaction A.6, the epoxide prepared in Reaction A.5 is reacted with a heterocyclic reactant, H-X, in an alcoholic solvent at a temperature of from about 20° C. to 100° C. Solvent choice is not critical so long as the solvent employed is inert to the ongoing reaction and the reactants are sufficiently solubilized to effect the desired reaction. Typical solvents for this reaction include the alcohols, preferably isopropanol or ethanol. The reaction is preferably carried out at a temperature of about 80° C.

Reaction A.7 is a standard amino deprotection reaction using procedures and methods known in the art to afford the corresponding amine which is used in Reaction I, above. This amine may be reacted without purification, but it is preferably purified first.

The compounds of formula IA, where R¹ is —S-aryl, are prepared by first reacting amino-protected serine with triphenylphosphine and diethylazodicarboxylate (DEAD) in an aprotic solvent at a temperature of from about –80° C. to 0° C. to form the corresponding β-lactone. The reaction is typically carried out in an ether, such as tetrahydrofuran at a temperature of from about –80° C. to –50° C. Next, the lactone ring is opened to provide a compound having the structure:

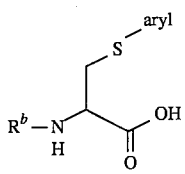

by reacting the lactone with an appropriately substituted thioanion having the structure, —S-aryl. The thioanion compound is preferably formed by reacting the corresponding thiol with a strong base, such as sodium hydride or potassium hydride. This reaction is typically carried out in an aprotic solvent at a temperature from about 0° C. to about 40° C. and under an inert atmosphere, such as nitrogen. Typical solvents for this reaction include ethers, preferably tetrahydrofuran.

Alternatively, the compounds of formula IA, where $R^1$ is —S-aryl, may be prepared using the procedures detailed in Photaki, JACS, 85, 1123 (1963), and Sasaki, N. A. et al, Tetrahedron Letters, 28, 6069 (1987). For example, the compounds may be prepared by reacting doubly protected serine (carboxy-protected and amino-protected) with toluenesulfonyl chloride in the presence of dimethylaminopyridine (DMAP) and an acid scavenger such as pyridine in an aprotic solvent such as methylene chloride to form the corresponding toluenesulfonate which may then reacted with an appropriately substituted thioanion having the structure, —S-aryl. The thioanion compound is preferably formed by reacting the corresponding thiol with a strong base as described above. The carboxy-protecting group may be removed from the resulting doubly protected arylthioalanine using conditions known in the art.

The heterocyclic reactants of the formula H-X, used in Reaction A.6, may be prepared using procedures and methods known in the art. For example, the heterocyclic reactants were typically prepared from the corresponding amino-protected amino acids by acid activation followed by treatment with an alkylamine. This reaction is typically carried out in the presence of an acid scavenger, such as N-methylmorpholine. Removal of the amino-protecting group using standard chemical deprotecting techniques then provides the desired heterocyclic reactants. Specifically, the [3S-(3R*,4aR*,8aR*)]-decahydroisoquinoline-3-N-t-butylcarboxamide was prepared using 2S-1,2,3,4-tetrahydro-3-isoquinolinecarboxylic acid by the following procedure:

1) amino-protection (t-Boc);
2) acid activation/reaction with t-butylamine;
3) catalytic hydrogenation;
4) amino-deprotection.

The piperazine reactants may be prepared by converting an appropriately substituted pyrazine compound to the corresponding piperazine compound using procedures known in the art, preferably using catalytic hydrogenation. For example, the hydrogenation may be accomplished by combining the pyrazine reactant with a catalyst under a hydrogen atmosphere in an aprotic solvent at a temperature from about 0° C. to about 60° C. Suitable catalysts include palladium-on-carbon, platinum metal, platinum oxide and the like. A preferred catalyst is platinum oxide. Typical solvents for this reaction include tetrahydrofuran, dimethylformamide or a mixture of tetrahydrofuran and dimethylformamide.

The nitrogen atom on the resultant piperazine reactant may be alkylated using procedures known in the art. For example, the piperazine reactant may be reacted with a halo($C_1$–$C_4$)alkyl, or halomethylpyridine, such as methyl iodide or chloromethylpyridine. Preferred halo substituents include chloro, bromo and iodo. The reaction is carried out at temperatures of from about 0° C. to 60° C. in a mutually inert solvent and in the presence of an acid scavenger. A preferred acid scavenger is potassium carbonate. Typical solvents include a mixture of a protic and aprotic solvents such as acetonitrile and water. Solvent choice is not critical so long as the solvent employed is inert to the ongoing reaction and the reactants are sufficiently solubilized to effect the desired reaction.

Alternatively, the alkylated piperazine reactant may be prepared using reductive amination. For example, the piperazinereactant prepared above may be reacted with an aldehyde (for example, 3-pyridine carboxylic aldehyde, ethanal, propanal) or a ketone in the presence of a reducing agent and an acid. The reaction is typically carried out in an alcoholic solvent such as methanol, ethanol or isopropanol. Typical reducing agents include sodium borohydride, lithium cyanoborohydride, sodium cyanoborohydride, and the like. A preferred reducing agent is sodium cyanoborohydride. Typical acids include any protic acid such as hydrochloric acid, sulfuric acid, methanesulfonic acid, or acetic acid. A preferred acid is acetic acid.

The carboxylic acid reactant, Z—COOH, used in Reaction I, to the extent not commercially available, can be prepared using known procedures. More particularly, this reactant may be prepared by further substitution and/or oxidation of a commercially available aryl or heterocyclic compound. For example, aryl or heterocyclic compounds of the formula Z—$CH_3$ may be oxidized using procedures known in the art. Specifically, the compound of the formula Z—$CH_3$ may be reacted with an oxidizing agent such as selenium dioxide or potassium permanganate at temperatures of from about 0° C. to 200° C. in a mutually inert solvent, such as water or diphenylether.

A second method for preparing compounds of the formula Z—COOH, involves protecting an appropriately substituted carboxylated aryl or heterocyclic with a carboxy-protecting group, and then further substituting the aryl or heterocyclic group using procedures known in the art. The carboxy-protecting group may then be removed using procedures known in the art to provide the desired carboxylic acid reactant, Z—COOH.

The term "carboxy-protecting group" as used in the specification refers to substituents of the carboxy group commonly employed to block or protect the carboxy functionality while reacting other functional groups on the compound. Examples of such carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, β-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl and like moieties. A preferred method of protecting the carboxy group involves converting the carboxy moiety to an amide moiety and then hydrolyzing the amide back to provide the desired carboxy substituent. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

A preferred procedure for protecting the carboxy moiety involves the acid activation of the carboxy moiety, followed by the formation of an amide. For example, the carboxy moiety may be converted to an acyl halide, acyl anhydride, acyl imidazole and the like, preferably in the presence of an acid scavenger to form an activated carboxy moiety. A commercially available acid chloride is typically employed, obviating the need for further acid activation. Preferred acid scavengers are the trialkylamines, preferably triethylamine. The reaction is typically carried out in an aprotic solvent such as diethylether, methylene chloride or the like. A preferred solvent is methylene chloride. Solvent choice is not critical so long as the solvent employed is inert to the ongoing reaction and the reactants are sufficiently solubilized to effect the desired reaction. The activated carboxy moiety is then reacted with an amine, $R^{11}$—$NH_2$, for example aniline, in an aprotic solvent to provide an amide reactant, Z—C(O)NH—$R^{11}$ which may then be further substituted according to known procedures.

The amide reactant, Z—C(O)NH—$R^{11}$, may be further substituted by ortho deprotonation of the heterocyclic or aryl group, Z, to provide the corresponding anion followed by reaction with a variety of reagents such as alkyl halides, or halogenating agents such as bromine. The amide reactant is generally deprotonated twice using two equivalents of a strong base such as n-butyl lithium or sec-butyl lithium relative to the amide reactant, optionally in the presence of a metal coordinating agent such as tetramethylethylenediamine (TMEDA). The reaction is typically carried out in an aprotic solvent, preferably an ether such as diethylether, tetrahydrofuran or the like at a temperature from about −78° C. to about 25° C.

The resultant compound may then be hydrolyzed using procedures known in the art to provide the desired, substituted carboxylic acid reactant, Z—COOH. For example, a suitable hydrolysis involves exposing the amide reactant to a strong mineral acid, organic acid, or a mineral acid/organic mixture at a temperature from about 100° C. to about 160° C. Typical acids which may be used in this reaction include hydrobromic acid, acetic acid, hydrochloric acid and the like. A sealed tube may optionally be employed to accelerate the reaction rate.

A third method for preparing the substituted carboxylic acid reactant Z—COOH, involves diazotization of an aniline, followed by a quenching of the resultant diazonium salt. Specifically, the amino moiety of the aniline reactant is converted to a diazonium salt by reaction with nitrous acid. Nitrous acid may be produced in situ by treating sodium nitrite with an aqueous solution of a strong acid such as hydrochloric acid, or sulfuric acid. This reaction is typically carried out at or below 5° C. The diazonium salt is then quenched by reaction with suitable reagent to provide the desired substituted aromatic system. Representative quenching reagents include water, cyanide, halide, aqueous sulfuric acid, and the like. Typically, the reaction will be heated to facilitate the desired reaction.

There are a variety of reactions that are known in the art which may be used to produce the desired substitutions on the aryl or heterocyclic rings. For example, there are a variety of aromatic electrophilic and nucleophilic substitution reactions oulined in chapters 11 and 13 of March, J., "Advanced Organic Chemistry," 3rd edition, Wiley, 1985.

In addition, the Compounds of the formula Z—COOH may be prepared by carboxylating an appropriately substituted aryl of heterocyclic compound. The carboxylation may be accomplished using a number of different reagents. For example, the aryl or heterocyclic reagent may be reacted with phosgene, oxalyl chloride, urea hydrochloride, or N,N-diethylcarbamoyl chloride in the presence of Friedel-Crafts catalysts. A variation of this method involves reacting the aryl or heterocyclic reagent with an alkyl thiolchloroformate (RSCOCl), or a carbamoyl chloride ($H_2$NCOCl) to provide an amide and a thiol ester, respectively. The amide and thiol ester may then be hydrolyzed to provide the desired carboxy group. March, at 491.

Examples of Friedel-Crafts catalysts include the Lewis acids, such as aluminum bromide ($AlBr_3$), aluminum chloride ($AlCl_3$), iron (III) chloride ($FeCl_3$), boron trichloride ($BCl_3$), boron trifluoride ($BF_3$), and the like. See also, March, J., "Advanced Organic Chemistry," 3rd edition, Wiley, 1985; Olah, "Friedel-Crafts and Related Reactions," Interscience, New York, 1963–1965; and Olah, "Friedel-Crafts Chemistry," Wiley, New York, 1973.

Additionally, the quinoline carboxylic acid reactants may be prepared by reacting an appropriately substituted aniline with glycerol using the Skraup reaction disclosed in Bradford, L. et al., J. Chem. Soc., 1947, p 437. For example, 3-amino benzoic acid may be reacted with glycerol in the presence of an oxidizing agent such as m-nitro benzene sulfonic acid or sodium m-nitro benzene sulfonate in a 60–75% aqueous solution of sulfuric acid to provide the desired carboxy-substituted quinoline. The reaction is typically carried out at a temperature from about 35° C. to reflux temperature for one to six hours, preferably from about 50° C. to reflux temperature for two to four hours.

The resultant reactants may then be reduced or hydrogenated using procedures known in the art. See e.g., March, at 700. A preferred procedure involves catalytic hydrogenation, for example by combining the quinoline carboxylic acid reactant with hydrogen gas in the presence of a catalyst. A preferred catalyst is palladium-on-carbon. Typical solvents suitable for use in this reaction include any organic solvent such as ethyl acetate. Solvent choice is not critical so long as the solvent employed is inert to the ongoing reaction. The reaction is generally substantially complete after about 1 to 24 hours when conducted at a temperature in the range of from about 25° C. to about 100° C.

As noted above, all asymmetric forms, individual isomers and combinations thereof are considered part of this invention. Such isomers may be prepared from their respective precursors by the procedures described above, by resolving the racemic mixtures, or by separating the diastereomers. The resolution can be carried out in the presence of a resolving agent, by chromatography or by repeated crystallization or by some combination of these techniques which are known in the art. Further details regarding resolutions can be found in Jacques et al., Enantiomers, Racemates, and Resolutions, John Wiley & Sons 1981.

The compounds employed as initial starting materials in the synthesis of the compounds of this invention are known and, to the extent not commercially available are readily synthesized by standard procedures commonly employed by those in the art.

The pharmaceutically acceptable salts of the invention are typically formed by reacting a compound of formula I with an equimolar or excess amount of acid or base. The reactants are generally combined in a mutual solvent such as diethylether or benzene, for acid addition salts, or water or alcohols for base addition salts. The salts normally precipitate out of solution within about one hour to about ten days and can be isolated by filtration or other conventional methods.

The following Preparations and Examples further illustrate specific aspects of the present invention. It is to be understood, however, that these examples are included for illustrative purposes only and are not intended to limit the scope of the invention in any respect and should not be so construed.

In the following Preparations and Examples, the terms melting point, nuclear magnetic resonance spectra, electron impact mass spectra, field desorption mass spectra, fast atom bombardment mass spectra, infrared spectra, ultraviolet spectra, elemental analysis, high performance liquid chromatography, and thin layer chromatography are abbreviated "m.p.", "NMR", "EIMS", "MS(FD)", "MS(FAB)", "IR", "UV", "Analysis", "HPLC", and "TLC", respectively. In addition, the absorption maxima listed for the IR spectra are only those of interest and not all of the maxima observed.

In conjunction with the NMR spectra, the following abbreviations are used: "s" is singlet, "d" is doublet, "dd" is doublet of doublets, "t" is triplet, "q" is quartet, "m" is multiplet, "dm" is a doublet of multiplets and "br.s", "br.d", "br.t", and "br.m" are broad singlet, doublet, triplet, and multiplet respectively. "J" indicates the coupling constant in Hertz (Hz). Unless otherwise noted, NMR data refers to the free base of the subject compound.

The NMR spectra were obtained on a Brüker Corp. 270 MHz instrument or on a General Electric QE-300 300 MHz instrument. The chemical shifts are expressed in delta ($\delta$) values (parts per million downfield from tetramethylsilane). MS(FD) spectra were taken on a Varian-MAT 731 Spectrometer using carbon dendrite emitters. EIMS spectra were obtained on a CEC 21-110 instrument from Consolidated Electrodynamics Corporation. MS(FAB) spectra were obtained on a VG ZAB-3 Spectrometer. IR spectra were obtained on a Perkin-Elmer 281 instrument. UV spectra were obtained on a Cary 118 instrument. TLC was carried out on E. Merck silica gel plates. Melting points are uncorrected.

Preparation 1

A. [3S-(3R*,4aR*,8aR*,2'S*,3'R*)]-2-[3'-N-(Benzyloxycarbonyl)amino- 2'-hydroxy-4'-phenyl]butyl decahydroisoquinoline-3-N-t-butylcarboximide A solution of [1'S-(1'R*,1R*)]-1-[1'-N(benzyloxycarbonyl)amino-2'-(phenyl)ethyl] oxirane and [3S -(3R*,4aR*, 8aR*)]-decahydroisoquinoline-3-N-t-butylcarboxamide in absolute ethanol was heated at 80° C. overnight. The reaction mixture was reduced to dryness under reduced pressure to provide a residue. This residue was purified using flash chromatography (gradient eluent of 10–50% ethyl acetate in methylene chloride) to provide 6.47 g of an off-white foam.

Yield: 75%.

$^1$H NMR (CDCl$_3$): $\delta$1.29 (s, 9H), 1.25–2.05 (m, 2H), 2.20–2.35 (m, 2H), 2.55–2.70 (m, 11H), 2.85–3.10 (m, 3H), 3.24 (br.s, 1H), 3.82 (br.s, 1H), 3.98 (br.s, 1H), 4.99 (br.s, 2H), 5.16–5.18 (m, 1H), 5.80 (br.s, 1H), 7.05–7.38 (m, 10H).

IR (CHCl$_3$): 3600–3100 (br.), 3031, 2929, 1714, 1673, 1512, 1455, 1368, 1232, 1199, 1047 cm$^{-1}$.

MS(FD): m/e 536 (M$^+$).

B. [3S-(3R*,4aR*,8aR*,2'S*,3'R*)]-2-[3'-Amino-2'-hydroxy-4'-phenyl]butyl decahydroisoquinoline-3-N-t-butylcarboxamide A rapidly stirring suspension of 6.37 g (11.91 mmol) of the subtitled compound of Preparation 1A and 1.2 g of 10% palladium-on-carbon in 200 mL of absolute ethanol was placed under an atmosphere of hydrogen. After approximately 48 hours, the reaction mixture was filtered through celite and reduced to dryness under reduced pressure to provide 5.09 g of the desired subtitled compound. This compound was used without further purification.

$^1$H NMR (CDCl$_3$): $\delta$1.33 (s, 9H), 1.40–1.95 (m, 10H), 2.25–2.48 (m, 2H), 2.59–2.75 (m, 3H), 2.80–3.40 (m, 7H), 3.75–3.90 (m, 1H), 6.19 (br.s, 1H), 7.18–7.35 (m, 5H).

IR (CHCl$_3$): 3600–3100 (br.), 2929, 2865, 1671, 1515, 1455, 1367, 1245, 1047 cm$^{-1}$.

MS(FD): m/e 402 (M$^+$, 100).

Preparation 2

A. 2R-N(Benzyloxycarbonyl)amino-3-naphth-2-ylthio propanoic acid

To a solution of 1.28 g (8.00 mmol) of naphthalene-2-thiol in 30 mL of tetrahydrofuran, was slowly added 1.77 g (8.16 g) of 60% sodium hydride, under nitrogen. After stirring for approximately 15 minutes, a solution of N(benzyloxycarbonyl)serine-$\beta$-lactone in 20 mL of tetrahydrofuran was slowly added. The reaction mixture was allowed to react at room temperature for approximately one hour, and then was concentrated under reduced pressure to provide a residue. This residue was dissolved in ethyl acetate and washed sequentially with 0.5N sodium bisulfate and a saturated brine solution. The resulting layers were separated and the organic layer was dried over sodium sulfate, filtered, and then concentrated under reduced pressure to provide a residue. This residue was purified using flash chromatography to provide 2.08 g of a pale yellow solid.

Yield: 68%.

$^1$H NMR (CDCl$_3$): $\delta$3.42–3.61 (br.m, 2H), 5.53–5.76 (br.s, 1H), 4.85–5.08 (br.m, 2H), 5.54–5.76 (br.s, 1H), 7.06–7.97 (m, 12H).

$[\alpha]_D$ –55.72° (c 1.0, MeOH).

IR (KBr): 3348, 3048, 1746, 1715, 1674, 1560, 1550, 1269, 1200, 1060 cm$^{-1}$.

MS(FD): m/e 381 (M$^+$), 381 (100).

Analysis for C$_{20}$H$_{19}$NO$_4$S: Calcd: C, 66.12; H, 5.02; N, 3.67; Found: C, 66.22; H, 5.04; N, 3.86.

B. 3R-1-Diazo-2-oxo-3-N-(benzyloxycarbonyl)amino-4-(naphth-2-ylthio)butane

To a cold (–30° C.) solution of 15.38 g (40.3 mmol) of subtitled compound of Preparation 2A in 230 mL of ethyl acetate, was slowly added 5.62 mL (40.3 mmol) of triethylamine, under nitrogen via syringe. To the resulting solution was then added 7.84 mL (60.5 mmol) of isobutyl chloroformate, via syringe. In a separate flask, 10 g of N(methyl)-N(nitro)-N(nitroso)-guanidine was carefully added to a bilayer mixture of 170 mL of diethylether and 170 mL of a 5N sodium hydroxide solution, resulting in a large evolution of gas. When this reaction was substantially complete, the organic layer was decanted from the aqueous layer onto potassium hydroxide and dried. This diazomethane formation and addition was repeated using identical quantities of diethylether and sodium hydroxide and 30 g of N(methyl)-N(nitro)-N(nitroso)-guanidine. The resultant diazomethane reactant was then added to the mixed anhydride solution prepared above and the reaction mixture was allowed to react cold (–30° C.) for approximately 20 minutes. When the reaction was substantially complete, as indicated by TLC, nitrogen was bubbled through the solution using a fire polished Pasteur piper to remove any excess diazomethane and then the solution was concentrated under reduced pressure to provide a residue. This residue was purified using flash chromatography (eluent of 10% ethyl acetate in methylene chloride) to provide 13.62 g of a yellow oil.

Yield: 83%.

$^1$H NMR (CDCl$_3$): $\delta$3.32–3.46 (m, 2H), 4.40–4.67 (m, 1H), 5.00–5.09 (m, 2H), 5.44 (s, 1H), 5.76 (d, J=7.8 Hz, 1H), 7.25–7.86 (m, 12H).

C. 3R-1-Chloro-2-oxo-3-N-(benzyloxycarbonyl)amino-4-(naphth-2-ylthio)butane

A short burst (about 2 seconds) of anhydrous hydrochloric acid (gas) was passed through a cold (−20° C.) solution of 13.62 g (33.59 mmol) of the subtitled compound of Preparation 2B in 230 mL of diethylether, resulting in the evolution of a gas. This procedure was repeated taking care not to add excess hydrochloric acid. When the reaction was substantially complete, as indicated by TLC, the solution was concentrated under reduced pressure to provide a residue. This residue was purified using flash chromatography (eluent of 10% ethyl acetate in methylene chloride) to provide 12.05 g of a pale tan solid.

Yield: 87%.

$^1$H NMR (CDCl$_3$): δ3.41 (dd, J=12, 6 Hz, 1H), 3.53 (dd, J=12, 6 Hz, 1H), 4.18 (AB q, J=41.9 Hz, J=15.9 Hz, 2H), 4.77 (dd, J=9, 3 Hz, 1H), 5.04 (AB q, J=12 Hz, J=10.4 Hz, 2H), 5.59 (d, J=7 Hz, 1H), 7.24–7.85 (m, 12H).

$[α]_D$ −80.00° (c 1.0, MeOH).

IR (CHCl$_3$): 3426, 3031, 3012, 1717, 1502, 1340, 1230, 1228, 1045 cm$^{-1}$.

MS(FD): m/e 413 (M$^+$), 413 (100).

Analysis for C$_{22}$H$_{20}$NO$_3$SCl: Calcd: C, 63.84; H, 4.87; N, 3.38; Found: C, 64.12; H, 4.95; N, 3.54.

D. [3R-(3R*,4S*)]-1-Chloro-2-hydroxy-3-N-(benzyloxycarbonyl)amino-4-(naphth-2-ylthio)butane To a cold (0° C.) solution of 530 mg (1.28 mmol) of the subtitled compound of Preparation 2C, in 10 mL of tetrahydrofuran and 1 mL of water, was added 73 mg (1.92 mmol) of sodium borohydride. When the reaction was substantially complete as indicated by TLC, the solution was adjusted to pH 3 using 10 mL of an aqueous saturated ammonium chloride solution and 500 μL of a 5N hydrochloric acid solution. The resultant solution was extracted twice with methylene chloride and the combined organic layers were washed with water, dried over sodium sulfate, filtered and then concentrated under reduced pressure to provide a residue. This residue was purified using radial chromatography (eluent of methylene chloride) to provide 212 mg of a tan solid.

Yield: 40%.

$^1$H NMR (CDCl$_3$): δ3.40 (s, 2H), 3.61–3.71 (m, 2H), 3.97–3.99 (m, 2H), 4.99 (s, 2H), 5.16 (br.s, 1H), 7.21–7.83 (complex, 12H).

MS(FD): m/e 415 (M$^+$), 415 (100).

$[α]_D$ −47.67° (c 0.86, MeOH).

IR (CHCl$_3$): 3630, 3412, 3011, 1720, 1502, 1236, 1044 cm$^{-1}$.

Analysis for C$_{22}$H$_{22}$NO$_3$ClS: Calcd: C, 63.53; H, 5.33; N, 3.37; Found: C, 63.72; H, 5.60; N, 3.64.

E. [1'R-(1'R*,1S*)]-1-[(1'-N-(Benzyloxycarbonyl)amino-2'-(naphth-2-ylthio)ethyl]oxirane A solution of 31 mg (0.55 mmol) of potassium hydroxide in 1 mL of ethanol was added to a solution of 190 mg (0.46 mmol) of the subtitled compound of Preparation 2D, in 6 mL of a 1:2 ethanol/ethyl acetate solution. When the reaction was substantially complete, as indicated by TLC, the reaction mixture was poured into a water/methylene chloride mixture. The resulting layers were separated, and the organic layer was washed with water, dried over sodium sulfate, filtered and then concentrated under reduced pressure to provide a residue. This residue was purified using radial chromatography (eluent of 10% ethyl acetate in methylene chloride) to provide 172 mg of a light tan solid.

Yield: 99%.

$^1$H NMR (CDCl$_3$): δ2.76 (br.s, 2H) 3.01 (br.s, 1H), 3.31 (d, J=5 Hz, 2H), 3.77 (br.s, 1H), 5.05 (s, 2H), 5.22 (d, J=6 Hz, 1H), 7.25–7.85 (complex, 12H).

$[α]_D$ −125.42° (c 0.59, MeOH).

MS(FD): m/e 379 (M$^+$), 379 (100).

IR (CHCl$_3$): 3640, 3022, 2976, 1720, 1502, 1235, 1045 cm$^{-1}$.

Analysis for C$_{22}$H$_{21}$NO$_3$S: Calcd: C, 69.63; H, 5.58; N, 3.69; Found: C, 69.41; H, 5.53; N, 3.64.

F. [2S-(2R*,2'R*,3'S*)]-1-[2'-Hydroxy-3'-(N-benzyloxycarbonyl)amino- 4'-(naphth-2-ylthio) butyl]piperidine-2-N-(t-butyl)carboxamide A solution of 0.51 g (1.34 mmol) of the subtitled compound of Preparation 2E and 0.26 g (1.41 mmol) of the subtitled compound of Preparation 4C in 25 mL of isopropanol was heated to 55° C. for approximately forty eight hours. The resultant reaction mixture was cooled and then concentrated under reduced pressure to provide a crude material. This material was purified using radial chromatography (4 mm plate; eluent of 10% acetone in methylene chloride) to provide 104 mg of a white foam.

Yield: 14%.

$^1$H NMR (CDCl$_3$): δ1.29 (s, 9H), 1.44–1.82 (m, 6H), 2.19 (m, 1H), 2.40 (m, 1H), 2.68 (m, 2H), 3.09 (m, 1H), 3.46 (m, 2H), 4.00 (m, 2H), 5.01 (s, 2H), 5.73 (d, 1H), 6.01 (br.s, 1H), 7.23–7.34 (m, 5H), 7.45 (m, 3H), 7.72–7.83 (m, 4H).

MS (FD): m/e 563 (M$^+$, 100).

G. [2S-(2R*,2'S*,3'S*)]-1-[2'-Hydroxy-3'-amino-4'-(naphth- 2-ylthio)butyl]piperidine-2-N-(t-butyl)carboxamide A solution containing 1.05 g (0.18 mmol) of the subtitled compound of Preparation 2F in 10 mL of 30% hydrobromic acid in acetic acid was reacted for approximately one hour. The resultant reaction mixture was concentrated, azeotroped three times with toluene, redissolved in methanol containing 4.5 mL each of diethylamine and ammonium hydroxide and then concentrated under reduced pressure to provide a residue. This residue was purified using radial chromatography (1 mm plate; eluent of 3% methanol in methylene chloride containing 1% acetic acid) to provide 64 mg a white foam.

Yield: 80%.

$^1$H NMR (CDCl$_3$): δ1.29 (s, 9H), 1.52–1.73 (m, 6H), 1.84 (m, 1H), 2.31–2.43 (m, 2H), 2.75–3.04 (m, 5H), 3.17 (m, 1H), 3.41 (m, 1H), 3.71 (m, 1H), 6.22 (br.s, 1H), 7.47 (m, 3H), 7.73–7.82 (m, 4H).

MS (FD): m/e 430 (M$^+$, 100).

Preparation 3

A. 2S-N-(Benzyloxycarbonyl)-2-pyrrolidinecarboxylate pentafluorophenyl ester

To a cold (0° C.) solution of 30 g (0.12 mol) of 2S-N(benzyloxycarbonyl)-2-pyrrolidinecarboxylic acid and 25.8 g (0.14 mol) of pentafluorophenol in 450 mL of tetrahydrofuran, was added 27.7 g (0.14 mol) of 1-(3-dimethylaminopropyl)- 3-ethylcarbodiimide (EDC) in one portion, followed by 150 mL of methylene chloride. The resultant reaction mixture was warmed to room temperature and reacted for approximately four hours. When the reaction was substantially complete, as indicated by TLC, the reaction mixture was concentrated under reduced pressure to provide a residue. This residue was dissolved in 500 mL of ethyl acetate and washed sequentially with water, potassium carbonate, 1N hydrochloric acid and brine, dried over sodium sulfate, filtered and then reduced to dryness under reduced pressure to provide a solid. This solid was redissolved in hexane and washed with potassium carbonate, dried over sodium sulfate, filtered and reduced to dryness under reduced pressure to provide 45.95 g of the desired subtitled compound.

Yield: 92%.

$^1$H NMR (CDCl$_3$): δ1.95–2.15 (m, 2H), 2.20–2.35 (m, 1H), 2.35–2.50 (m, 1H), 3.50–3.75 (m, 2H), 4.65–4.75 (m, 1H), 5.02–5.30 (m, 2H), 7.20–7.45 (m, 5H).

B. 2S-N-(Benzyloxycarbonyl)pyrrolidine-2-N-(t-butyl)carboxamide

To a cold (0° C.) solution of 45.90 g (0.111 mmol) of the subtitled compound of Preparation 3A in 100 mL of anhydrous methylene chloride, was slowly added 100 mL (0.952 mmol) of t-butylamine. The reaction mixture was warmed to room temperature and reacted for approximately one hour and then diluted with 1000 mL of methylene chloride and then washed sequentially with 1N potassium carbonate, 1N hydrochloric acid, 1N potassium carbonate, and brine, dried over sodium sulfate, and then plug filtered using 50% ethyl acetate in hexane to provide 37.74 g of the desired compound which was used without further purification.

$^1$H NMR (CDCl$_3$): δ0.95–1.50 (m, 9H), 1.70–2.40 (m, 4H), 3.30–3.60 (m, 2H), 4.10–4.30 (m, 1H), 4.95–5.35 (m, 2H), 5.65 (br.s, 0.5H), 6.55 (br.s, 1H), 7.20–7.50 (m, 5.5H).

C. 2S-Pyrrolidine-2-N-(t-Butyl)carboxamide

The subtitled compound of Preparation 3B (2.71 g, 8.9 mmol) was deprotected substantially as detailed in Preparation 1B, using 500 mg of 10% palladium-on-carbon and hydrogen gas (1 atmosphere) in 200 mL of ethanol.

Yield: 1.53 g (100%).

$^1$H NMR (CDCl$_3$): δ1.35 (s, 9H), 1.60–1.75 (m, 2H), 1.76–1.90 (m, 1H), 2.00–2.15 (m, 1H), 2.58 (br.s, 1H), 2.80–3.05 (m, 2H), 3.55–3.65 (m, 1H), 7.45 (br.s, 1H).

D. [2S-(2R*,2'S*,3'R*)]-1-[3'-N(Benzyloxycarbonyl)amino-2-hydroxy-4'-phenylbutyl]pyrrolidine-2-N-(t-butyl)carboxamide A solution containing 122 mg (0.72 mmol) of the subtitled compound of Preparation 3C and 200 mg (0.68 mmol) of [1S-(1R*,1'R*)]-1-[(1'-N-(benzyloxycarbonyl)amino-2'-phenyl)ethyl]oxirane in 10 mL of methanol was stirred overnight. When the reaction was substantially complete, as indicated by TLC, the reaction mixture was concentrated under reduced pressure. The desired compound was purified using column chromatography (gradient eluent of 2–4% methanol in methylene chloride) to provide 232.2 mg of a clear amorphous solid.

Yield: 55%.

[α]$_D$ –56.97° (c=0.27, MeOH).

$^1$H NMR (CDCl$_3$): δ1.33 (s, 9H), 1.55–1.95 (m, 4H), 2.05–2.25 (m, 1H), 2.40–2.55 (m, 1H), 2.65–2.75 (m, 2H), 2.80–3.00 (m, 3H), 3.15–3.30 (m, 1H), 3.65–3.75 (m, 1H), 3.85–3.95 (m, 1H), 4.86 (br.d, J=1.1 Hz, 1H), 5.03 (s, 2H), 6.95 (m, 1H), 7.15–7.40 (m, 10H).

IR (CHCl$_3$): 3700–3100 (br.), 3434, 3031, 2976, 1720, 1664, 1604, 1512, 1455, 1394, 1367, 1343, 1233, 1156, 1107, 1063, 1028, 911 cm$^{-1}$.

MS(FD): m/e 468 (M$^+$, 100).

E. [2S-(2R*,2'S*,3'R*)]-1-[3'-Amino-2'-hydroxy-4'-phenylbutyl]pyrrolidine-2-N-t-butylcarboxamide The subtitled compound of Preparation 3D (222 mg, 0.47 mmol) was deprotected substantially as detailed in Preparation 1B, using 67 mg of 10% palladium-on-carbon and hydrogen gas (1 atmosphere) in 15 mL of ethanol. The desired compound was purified using column chromatography (eluent of 10% isopropanol in methylene chloride containing 0.75% ammonium hydroxide) to provide 80 mg of an off-white solid.

Yield: 51%.

[α]$_D$ –55.26° (c=0.23, MeOH).

$^1$H NMR (CDCl$_3$): δ0.80–3.70 (m, 25H), 6.90–7.40 (m, 6H).

IR (CHCl$_3$): 3692, 3600–3200 (br.), 2975, 1657, 1603, 1522, 1497, 1479, 1455, 1393, 1366, 1232, 1198, 1137, 1049, 882 cm$^{-1}$.

MS(FD): m/e 334 (M$^+$, 100).

Preparation 4

A. 2S-N-(t-Butoxycarbonyl)piperidine-2-carboxylic acid

A solution of 1.64 g of sodium carbonate in 15 ml of water was added to a cold (0° C.) solution of 2.0 g (15.5 mol) of 2S-piperidinecarboxylic acid in 50 mL of dioxane. After approximately ten minutes, 3.7 g (17.0 mol) of di-t-butyl dicarbonate was added to the mixture. The resultant reaction mixture was reacted for approximately six hours, concentrated to one fourth of the original volume and then acidified to pH 2 using 1M sodiumhydrogen sulfate and ethyl acetate. The resulting layers were separated, and the organic layers were washed with a saturated brine solution, dried over sodium sulfate, filtered and then reduced to dryness under reduced pressure to provide 2.67 g of a white crystalline solid.

Yield: 75%.

[α]$_D$ –55.26° (c=0.23, MeOH).

$^1$H NMR (CDCl$_3$): δ1.20–1.80 (m, 15H), 2.15–2.30 (m, 1H), 2.85–3.10 (m, 1H), 3.90–4.10 (m, 2H), 4.70–5.00 (m, 1H).

IR (CHCl$_3$): 3700–1800 (br.), 3025, 3018, 3011, 2980, 2947, 2865, 1716, 1685, 1449, 1394, 1368, 1280, 1252, 1162, 1147, 1129 cm$^{-1}$.

MS(FD): m/e 229 (M$^+$, 100).

Analysis for C$_{27}$H$_{37}$N$_3$O$_4$: Calcd: C, 57.63; H, 8.35; N, 6.11; Found: C, 57.90; H, 8.35; N, 6.19.

B. 2S-N-(t-Butoxycarbonyl)piperidine-2-carboxylate, pentafluorophenylester

To a cold (0° C.) solution of 2.53 g (11.03 mol) of the subtitled compound of Preparation 4A and 2.34 g (12.7 mol) of pentafluorobenzoic acid in 50 mL of tetrahydrofuran, was added 2.42 g (12.7 mol) of EDC. The resultant reaction mixture was warmed to room temperature and reacted for approximately two hours. The mixture was then concentrated under reduced pressure to provide a solid. This solid was redissolved in methylene chloride and washed sequentially with potassium carbonate and brine, dried over sodium sulfate, filtered and then reduced to dryness under reduced pressure to provide 3.85 g of a clear oil which solidified on standing.

Yield: 88%.

$^1$H NMR (CDCl$_3$): δ1.20–1.90 (m, 15H), 2.30–2.40 (m, 1H), 2.90–3.15 (m, 1H), 3.90–4.15 (m, 1H), 5.05–5.35 (m, 1H).

C. 2S-N-(t-Butoxycarbonyl)piperidine-2-N-t-butylcarboxamide

To a cold (0° C.) solution of 3.8 g (9.6 mmol) of the subtitled compound of Preparation 4B in 200 mL of methylene chloride, was slowly added 2.53 mL (24.0 mmol) of t-butylamine. The reaction mixture was reacted for approximately four hours and then concentrated under reduced pressure to provide a residue. This residue was redissolved in methylene chloride and then washed sequentially with 1M potassium carbonate and brine, dried over sodium sulfate, filtered and then purified using column chromatography (gradient eluent of 10–20% ethyl acetate in hexane) to provide 2.52 g of a white solid.

Yield: 92%.

[α]$_D$ –41.47° (c=0.506, MeOH).

$^1$H NMR (CDCl$_3$): δ1.10–1.70 (m, 15H), 2.20–2.35 (m, 1H), 2.65–2.82 (m, 1H), 3.90–4.10 (m, 1H), 4.62 (br.s, 1H).

IR (CHCl$_3$): 3600–3300 (br.), 2978, 2945, 2869, 1677, 1512, 1455, 1413, 1394, 1367, 1317, 1280, 1255, 1162, 1144, 1127, 1078, 1042, 868 cm$^{-1}$.

MS(FD): m/e 284 (M$^+$, 100).

Analysis for C$_{15}$H$_{28}$N$_2$O$_3$: Calcd: C, 63.35; H, 9.92; N, 9.85; Found: C, 63.10; H, 9.66; N, 9.92.

D. 2S-Piperidine-2-N-t-butylcarboxamide

A solution containing 1.0 g (3.5 mol) of the subtitled compound of Preparation 4C and 3.5 mL of trifluoroacetic acid in 25 mL of methylene chloride was stirred at room temperature for approximately two hours. The reaction mixture was concentrated and azeotroped once with toluene. The resultant reaction mixture was then partitioned between methylene chloride and sodium bicarbonate. The resulting layers were separated and organic layer was dried over sodium sulfate, filtered and reduced to dryness under reduced pressure to provide 641 mg of the subtitled compound.

Yield: 99%.

[α]$_D$ –22.45° (c=0.95, MeOH).

$^1$H NMR (CDCl$_3$): δ1.20–1.50 (m, 12H), 1.51–1.62 (m, 1H), 1.64 (s, 1H), 1.75–1.88 (m, 1H), 1.90–2.00 (m, 1H), 2.60–2.72 (m, 1H), 2.98–3.10 (m, 2H), 6.63 (br.s, 1H).

IR (CHCl$_3$): 3363, 3002, 2969, 2940, 2860, 1738, 1660, 1522, 1480, 1455, 1398, 1367, 1324, 1295, 1230, 1129, 1110, 852 cm$^{-1}$.

MS(FD): m/e 184 (M$^+$, 100).

E. [2S-(2R*,2'S*,3'R*)]-N-[3'-(N-Benzyloxycarbonyl)amino-2'-hydroxy- 4'-phenyl]butyl piperidine-2-N-t-butylcarboxamide A solution containing 195 mg (1.06 mmol) of the subtitled compound of Preparation 4D and 300 mg (1.01 mmol) of [1S-(1R*,1'R*)]-1-[(1'-N(benzyloxycarbonyl)amino-2'-phenyl)ethyl]oxirane in 10 mL of isopropanol was stirred at 55° C. for approximately forty eight hours. When the reaction was substantially complete, as indicated by TLC, the reaction mixture was concentrated under reduced pressure. The desired compound was purified using column chromatography (gradient eluent of 1–5% isopropanol in methylene chloride).

Yield: 395 mg (81%).

[α]$_D$ –55.64° (c=0.22, MeOH).

$^1$H NMR (CDCl$_3$): δ1.32 (s, 9H), 1.45–1.90 (m, 6H), 2.25–2.50 (m, 2H), 2.70–3.20 (m, 5H), 3.30–3.40 (m, 1H), 3.75–4.05 (m, 2H), 4.95–5.10 (m, 3H), 6.15 (br.s, 1H), 7.18–7.40 (m, 10H).

IR (CHCl$_3$): 3700–3100 (br.), 3623, 3021, 2976, 1668, 1603, 1511, 1456, 1313, 1047, 878 cm$^{-1}$.

MS(FD): m/e 482 (M$^+$, 100).

F. [2S-(2R*,2'S*,3'R*)]-N-[3'-Amino-2'-hydroxy-4'-phenyl]butyl piperidine-2-N-t-butylcarboxamide The subtitled compound of Preparation 4E (371 mg, 0.77 mmol) was deprotected substantially as detailed in Preparation 1B, using 110 mg of 10% palladium-on-carbon and hydrogen gas in 20 mL of ethanol to provide 260 mg of a white foam.

Yield: 97%.

[α]$_D$ –64.92° (c=0.39, MeOH).

$^1$H NMR (CDCl$_3$): δ1.35 (s, 9H), 1.45–1.90 (m, 6H), 2.25–2.35 (m, 1H), 2.50–2.90 (m, 5H), 3.00–3.40 (m, 3H), 3.85–3.98 (m, 1H), 6.29 (s, 1H), 7.15–7.38 (m, 5H).

IR (CHCl$_3$): 3693, 3650–3100 (br.), 2943, 2862, 1671, 1603, 1517, 1497, 1455, 1394, 1367, 1233, 1185, 1049, 887 cm$^{-1}$.

MS(FD): m/e 348 (M$^+$, 100).

Preparation 5

A. Pyrazine-2-N-(t-butyl)carboxamide

To a slurry of 50 g (0.403 mol) pyrazine-2-carboxylic acid in 600 mL of tetrahydrofuran and 100 mL of dimethylformamide, was added 65.9 g (0.407 mol) of carbonyldiimidazole. The resultant reaction mixture was reacted at 50° C. until gas evolution ceased. After the reaction mixture cooled, 73.5 g (1.00 mol) of t-butylamine was slowly added. The reaction mixture was reacted for approximately thirty minutes, concentrated under reduced pressure, redissolved in 500 mL of methylene chloride and then washed sequentially with water, hydrochloric acid (pH 2), saturated sodium bicarbonate, water, 1M potassium hydroxide, and brine, dried over sodium sulfate, and concentrated to provide 68.5 g of a white solid.

Yield: 95%.

$^1$H NMR (CDCl$_3$): δ1.51 (s, 9H), 7.73 (br.s, 1H), 8.49 (m, 1H), 8.72 (m, 1H), 9.38 (s, 1H).

B. (±)-Piperazine-2-N-(t-butyl)carboxamide

A mixture of 68.5 g (0.382 mol) of the subtitled compound of Preparation 5A, 70 g (0.308 mol) of platinum oxide in 186 mL of ethanol was heated overnight at 40° C. under a hydrogen atmosphere (60 psi). The resultant crude material was filtered and the filtrate was concentrated to provide 65 g of white solid.

Yield: 95%.

MS(FD): m/e 185 (H$^+$, 100).

C. (±)-4-(Pyrid-3'-ylmethyl)piperazine-2-N-(t-butyl)carboxamide

To a solution of 5.0 g (0.027 mol) of the subtitled compound of Preparation 5B in 160 mL of a 1:1 mixture of water and acetonitrile, was added 18.65 g (0.135 mol) of potassium carbonate. The resultant mixture was vigorously stirred during the addition of 4.43 g (0.027 mol) of 3-chloromethylpyridine hydrochloride and then allowed to react overnight. The resultant reaction mixture was concentrated under reduced pressure, slurried in a solution of 20% isopropanol in chloroform and washed sequentially with water and brine, dried over sodium sulfate, filtered and then concentrated to provide a residue. This residue was purified using flash chromatography (eluent of 5% methanol in methylene chloride containing 1% ammonium hydroxide) to provide 1.34 g of a clear yellow oil.

Yield: 18%.

$^1$H NMR (CDCl$_3$): δ1.10 (s, 9H), 1.89–2.01 (m, 2H), 2.35 (m, 1H), 2.57–2.74 (m, 4H), 3.09 (m, 1H), 3.27 (s, 2H), 6.71 (br.s, 1H), 7.03 (m, 1H), 7.44 (m, 1H) 8.26 (m, 2H).

IR (KBr): 3691, 3611, 3366, 2974, 1666, 1602, 1521, 1479, 1456, 1427, 1393, 1366, 1324, 1139, 1047, 839 cm$^{-1}$.

MS(FD): m/e 276 (M$^+$, 100).

D. [2S-(2R*,2'S*,3'R*)]-1-[2'-Hydroxy-3'-(N-benzyloxycarbonyl)amino- 4'-phenylbutyl]-4-(pyrid-3"-ylmethyl)piperazine-2-N-(t-butyl)carboxamide A solution containing 0.377 g (1.27 mmol) of [1S-(1R*,1'R*)]-1-[(1'-N-Benzyloxycarbonyl)amino-2'-phenyl)ethyl]oxirane and 0.350 g (1.27 mmol) of the subtitled compound of Preparation 5C in 12 mL of isopropanol was reacted at 45° C. for approximately forty eight hours. The reaction mixture was cooled and then concentrated under reduced pressure to provide a crude material. This material was purified using radial chromatography (6 mm plate; gradient eluent of 5–10% isopropanol in methylene chloride) to provide 120 mg of isomer A and 68 mg of isomer B.

Yield: 26% overall.

Isomer A:

$^1$H NMR (CDCl$_3$): δ1.33 (s, 9H), 2.26–2.89 (m, 13H), 3.29 (m, 1H), 3.45 (s, 2H), 3.79–3.95 (m, 3H), 4.73 (br.s,

1H), 4.97 (br.s, 2H), 5.20 (m, 1H), 7.14–7.29 (m, 6H) 7.57 (m, 1H), 7.82 (br.s, 1H), 8.53 (m, 2H).

IR (KBr): 3692, 3434, 2970, 2829, 1714, 1661, 1604, 1579, 1512, 1455, 1427, 1393, 1365, 1231, 1149, 1029, 909 cm$^{-1}$.

MS(FD): m/e 573 (M$^+$, 100).

E. [2S-(2R*,2'S*,3'R*)]-1-[2'-Hydroxy-3'-amino-4'-phenyl]butyl- 4-(pyrid-3"-ylmethyl)piperazine-2-N-(t-butyl)carboxamide A solution containing 0.062 g (0.11 mmol) of the subtitled compound of Preparation 5D (isomer A) was stirred for approximately ninety minutes in 1.5 mL of a solution of 30% hydrobromic acid in acetic acid. The resultant mixture was concentrated, azeotroped three times with toluene, redissolved in methanol containing 1 mL each of diethylamine and ammonium hydroxide and then concentrated under reduced pressure to provide a residue. This residue was purified using radial chromatography (2 mm plate; gradient eluent of 15–25% methanol in methylene chloride containing 1% ammonium hydroxide) to provide 13 mg of a white solid.

Yield: 28%.

$^1$H NMR (CDCl$_3$): δ1.33 (s, 9H), 2.36–3.21 (m, 15H), 3.47 (d, 2H), 3.75 (m, 1H), 7.19–7.30 (m, 6H) 7.57 (m, 2H), 8.52 (m, 2H).

MS(FD): m/e 440 (M$^+$, 100).

Preparation 6

A. [2S-(2R*,2'S*,3'S*)]-1-[3'-N-(Benzyloxycarbonyl)amino-2'-hydroxy-4'-phenylthiobutyl]-4-[pyrid-3"-ylmethyl]piperazine-2-N-t-butylcarboxamide A solution of 596 mg (1.81 mmol) of [1S-(1R*,1'S*)]-1-[1'-N-(benzyloxycarbonyl)amino-2'-(phenylthio)ethyl]oxirane and 500 mg (1.81 mmol) of the subtitled compound of Preparation 5C in 15 mL of isopropanol were heated at 43° C. for approximately forty-eight hours. The reaction was monitored using TLC (10% isopropanol in methylene chloride containing 1% ammonium hydroxide; Isomer A R$_f$=0.7; Isomer B R$_f$=0.6). When the reaction was substantially complete, the reaction mixture was concentrated under reduced pressure to provide a residue. This residue was purified using radial chromatography (6 mm plate; gradient eluent of 5–15% isopropanol in methylene chloride containing 1% ammonium hydroxide) to provide 200 mg of isomer A as a light tan foam and 119 mg of an off-white foam (isomer B).

Isomer A:
Yield: 18%.

$^1$H NMR (CDCl$_3$): δ1.31 (s, 9H), 2.25–2.62 (m, 7H), 2.78–2.95 (m, 2H), 2.98–3.08 (m, 1H), 3.10–3.25 (m, 2H), 3.40–3.55 (m, 2H), 3.72–3.85 (m, 1H), 3.90–4.00 (m, 1H), 5.05 (s, 2H), 7.01 (br.s, 1H), 7.10–7.40 (m, 11H), 7.62 (d, J=7.8 Hz, 1H), 8.49 (s, 2H).

MS(FD): m/e 606 (M$^+$, 100).

Analysis for C$_{33}$H$_{43}$N$_5$O$_4$S: Calcd: C, 65.42; H, 7.15; N, 11.56; Found: C, 65.38; H, 7.27; N, 11.36.

Isomer B:
Yield: 11%.

$^1$H NMR (CDCl$_3$): δ1.33 (s, 9H), 2.25–2.85 (m, 8H), 3.20–3.32 (m, 3H), 3.47 (s, 2H), 3.78–3.95 (m, 2H), 5.06 (s, 2H), 5.30–5.38 (m, 1H), 7.10–7.42 (m, 12H), 7.55–7.85 (m, 2H), 8.50–8.60 (m, 2H).

MS (FD): m/e 606 (M), 497 (100).

HR MS (FAB) for C$_{33}$H$_{44}$N$_5$O$_4$S: Calcd: 606.3114; Found: 606.3141.

B. [2S-(2R*,2'S*,3'S*)]-1-[2'-Hydroxy-3'-amino-4'-phenylthiobutyl]-4-[pyrid-3"-ylmethyl]piperazine-2-N-t-butylcarboxamide A solution of 110 mg (0.18 mmol) of isomer B from Preparation 6A in 5 mL of 30% hydrobromic acid in acetic acid was stirred at room temperature for approximately 1 hour. The reaction mixture was concentrated under reduced pressure to provide a residue. This residue was redissolved in 4 mL of ammonium hydroxide. The resultant solution was extracted four times with 10 mL portions of a 10% solution of isopropanol in chloroform. The combined organic layers were dried over sodium sulfate, filtered and concentrated under reduced pressure to provide a residue. This residue was purified using radial chromatograghy (2 mm plate; gradient eluent of 10–30% methanol in methylene chloride containing 1% ammonium hydroxide) to provide 65 mg of a light yellow foam.

Yield: 72%.

$^1$H NMR (CDCl$_3$): δ1.25 (s, 9H), 2.25–2.78 (m, 7H), 3.00–3.32 (m, 4H), 3.47 (s, 2H), 3.60–3.75 (m, 1H), 4.18–4.35 (m, 1H), 6.90–7.65 (m, 9H), 8.40–8.60 (m, 2H).

MS(FD): m/e 473 (M$^+$, 100).

Preparation 7

A. [3S-(3R*,4aR*,8aR*,2'S*,3'S*)]-2-[3'-N-(Benzyloxycarbonyl)amino- 2'-hydroxy-4'-(naphth-2-ylthio)]butyl decahydroisoquinoline-3-N-(t-butyl)carboxamide A solution was prepared containing 165 mg (0.40 mmol) of the subtitled intermediate of Preparation 2E and 94 mg (0.43 mmol) of 3-(1-N(t-butyl)amino-1-oxomethyl)octahydro-(2H)-isoquinoline in 5 mL of ethanol. The resulting reaction mixture was allowed to react at 80° C. for approximately 19 hours. The solution was then cooled to room temperature and concentrated under reduced pressure to provide a residue. This residue was purified using radial chromatography (eluent of 10% ethyl acetate in methylene chloride) to provide 103 mg of an off-white foam.

Yield: 42%.

$^1$H NMR (CDCl$_3$): δ1.10–1.73 (m, 20H), 2.13–2.31 (m, 2H), 2.44–2.53 (m, 1H), 2.56–2.68 (m, 1H), 2.86–2.97 (m, 1H), 3.52 (br.s, 2H), 4.02 (br.s, 2H), 4.98 (s, 2H), 5.65 (s, 1H), 5.94 (s, 1H), 7.25–7.83 (complex, 13H).

MS (FD): m/e 629 (M$^+$), 138 (100). [α]$_D$ –92.45° (c 1.06, MeOH).

IR (CHCl$_3$): 3429, 3010, 2929, 1713, 1670, 1514, 1047 cm$^{-1}$.

Analysis for C$_{35}$H$_{47}$N$_3$O4S: Calcd: C, 69.98; H, 7.67; N, 6.80; Found: C, 69.86; H, 7.78; N, 6.58.

B. [3S-(3R*,4aR*,8aR*,2'S*,3'S*)]-2-[3'-amino-2'-hydroxy- 4'-(naphth-2-ylthio)]butyl decahydroisoquinoline-3-N-butyl)carboxamide A solution was prepared containing 50 mg (0.081 mmol) of the subtitled intermediate of Preparation 7A and 1 mL of a 38% aqueous hydrobromic acid solution in acetic acid. The resultant reaction mixture was allowed to react at room temperature for approximately 1 hour and then was concentrated under reduced pressure to provide a residue. This residue was slurried with toluene and then concentrated under reduced pressure to provide 61 mg of the desired subtitled intermediate. This compound was used crude without purification in Example 9.

$^1$H NMR (CDCl$_3$): δ1.14 (s, 1H), 1.17–2.07 (complex, 15H), 2.66–2.87 (m, 2H), 3.21–3.25 (m, 2H), 3.75 (d, J=12 Hz, 1H), 3.85 (d, J=6 Hz, 1H), 4.36–4.47 (m, 1H), 6.73 (s, 1H), 7.39–7.90 (complex, 7H).

MS (FD): 483 (M$^+$), 483 (100).

Preparation 8

A. 2R-2-N(Benzyloxycarbonyl)amino-3-phenylthio propanoic acid

The desired subtitled intermediate was prepared substantially in accordance with the procedure detailed in Procedure 2A, using 13.1 mL (127 mmol) of thiophenol, 4.6 g (117 mmol) of a 60% sodium hydride solution and 25.6 g (116 mmol) of L-N(benzyloxycarbonyl)serine β-lactone in 450 mL of tetrahydrofuran to provide a residue. This residue was purified using flash chromatography (gradient eluent of 0–2% acetic acid in a 4:1 methylene chloride/ethyl acetate mixture) to provide 27.9 g of a white solid.

Yield: 72%.

$^1$H NMR (CDCl$_3$): δ7.55–7.18 (m, 10H), 5.55 (d, J=7 Hz, 1H), 5.08 (s, 2H), 4.73–4.60 (m, 1H), 3.55–3.30 (m, 2H).

IR (KBr): 3304, 3035, 1687, 1532, 736 cm$^{-1}$.

MS(FD): m/e 332, 288, 271, 181.

Analysis for C$_{17}$H$_{17}$NO$_4$S: Calcd: C, 61.61; H, 5.17; N, 4.23; Found: C, 61.69; H, 5.22; N, 4.47.

B. 3S-1-Diazo-2-oxo-3-N-(benzyloxycarbonyl)amino-4-phenylthio butane

The desired subtitled compound was prepared substantially in accordance with the procedure detailed in Procedure 2B, using 12.1 g (37 mmol) of the subtitled compound of Preparation 8A, 5.09 mL (37 mmol) of triethylamine, 7.13 mL (55 mmol) isobutyl chloroformate, 146 mmol of a diazomethane solution to provide a residue. The diazomethane solution was prepared using 100 mL of diethylether, 150 mL of a 5N sodium hydroxide solution and 21 g (146 mmol) of N(methyl)-N(nitro)-N(nitroso)-guanidine as described in Preparation 2B. This residue was purified using flash chromatography (gradient eluent of 0–5% ethyl acetate in methylene chloride) to provide a yellow oil.

Yield: 73%.

$^1$H NMR (CDCl$_3$): δ7.50–7.19 (m, 10H), 5.62 (d, J=7 Hz, 1H), 5.47 (br.s, 1H), 5.11 (s, 2H), 4.50–4.32 (m, 1H), 3.33 (d, J=6 Hz, 1H).

IR (KBr): 3012, 2115, 1720, 1501, 1367, 1228 cm$^{-1}$.

MS (FD): m/e 356, 328, 242.

C. 3R-1-Chloro-2-oxo-3-N-(benzyloxycarbonyl)amino-4-phenylthio butane

The desired subtitled compound was prepared substantially in accordance with the procedure detailed in Procedure 2C, using 22.3 g (63 mmol) of the subtitled compound of Preparation 8B and small quantities of hydrochloric acid (gas) in 400 mL of diethylether to provide 21 g of a white solid. This solid was used without further purification.

$^1$H NMR (CDCl$_3$): δ7.50–7.15 (m, 10H), 5.56 (dd, J=2, 6.7 Hz, 1H), 5.11 (s, 2H), 4.78–4.67 (m, 1H), 4.20 (d, J=15.9 Hz, 1H), 4.12 (d, J=15.9 Hz, 1H), 3.48–3.23 (m, 2H).

IR (KBr): 3349, 1732, 1684, 1515, 1266 cm$^{-1}$.

MS (FD): m/e 363 (M$^+$).

Analysis for C$_{18}$H$_{18}$NO$_3$SCl: Calcd: C, 59.42; H, 4.99; N, 3.85; Found: C, 59.57; H, 5.09; N, 4.13.

D. [2S-(2R*,3S*)]-1-Chloro-2-hydroxy-3-N-(benzyoxycarbonyl)amino- 4-phenylthio butane The desired subtitled compound was prepared substantially in accordance with the procedure detailed in Procedure 2D, using 21 g (58 mmol) of the subtitled compound of Preparation 8C, 2.4 g (63 mmol) of sodium borohydride in 300 mL of tetrahydrofuran to provide a residue. This residue was purified using flash chromatography (gradient eluent of 0–2% methanol in methylene chloride) followed by flash chromatography (gradient eluent of 0–2% ethyl acetate in chloroform) and then recrystallized from methylene chloride at −78° C. to provide 8.3 g of the subtitled compound.

Yield: 39%.

$^1$H NMR (CDCl$_3$): δ7.47–7.19 (m, 10H), 5.22–5.03 (m, 1H), 5.09 (s, 2H), 4.01–3.89 (m, 2H), 3.75–3.58 (m, 2H), 3.32 (d, J=4 Hz, 2H).

IR (KBr): 3321, 2951, 1688, 1542, 1246, 738 cm$^{-1}$.

MS (FD): m/e 366 (M$^+$), 119.

Analysis for C$_{18}$H$_{20}$NO$_3$SCl: Calcd: C, 59.09; H, 5.51; N, 3.83; Found: C, 59.03; H, 5.50; N, 3.96.

E. [1'R-(1'R*,1S*)]-1-[(1'-N-(benzyoxycarbonyl)amino-2'-phenylthio)ethyl oxirane The desired subtitled compound was prepared substantially in accordance with the procedure detailed in Procedure 2E, using 8.3 g (23 mmol) of the subtitled compound of Preparation 8D, 1.4 g (25 mmol) of potassium hydroxide in 400 mL of ethanol to provide a residue. This residue was purified using flash chromatography (gradient eluent of 0–2% ethyl acetate in methylene chloride) to provide 6.4 g of a white solid.

Yield: 85%.

$^1$H NMR (CDCl$_3$): δ7.45–7.15 (m, 10H), 5.12 (s, 1H), 5.08 (s, 2H), 3.77–3.62 (m, 1H), 3.21 (d, J=6 Hz, 2H), 2.99 (m, 1H), 2.77 (m, 2H).

IR (KBr): 3303, 3067, 1694, 1538, 1257, 741 cm$^{-1}$.

MS (FD) m/e 329.

Analysis for C$_{32}$H$_{45}$N$_3$O$_4$S: Calcd: C, 65.63; H, 5.81; N, 4.25; Found: C, 65.48; H, 5.82; N, 4.29.

F. [3S-(3R*,4aR*,8aR*,2'S*,3'S*)]-2-[3'-N-(benzyloxycarbonyl)amino-2'-hydroxy-4'-(phenyl)thio]butyl decahydroisoquinoline-3-N-t-butyl carboxamide The desired subtitled compound was prepared substantially in accordance with the procedure detailed in Procedure 2F, using 6.3 g (19 mmol) of the subtitled compound of Preparation 8E, 5 g (21 mmol) of [3S-(3R*,4aR*,8aR*)]-decahydroisoquinoline-3-N-t-butylcarboxamide in 300 mL of ethanol to provide a residue. This residue was purified using flash chromatography (gradient eluent of 0–20% ethyl acetate in methylene chloride) to provide 4.3 g of a white solid.

Yield: 40%.

$^1$H NMR (CDCl$_3$): δ7.41–7.11 (m, 10H), 5.90 (d, J=5 Hz, 1H), 5.64 (s, 1H), 5.05 (d, J=4 Hz, 2H), 4.08–3.90 (m, 2H), 3.40 (d, J=6, 2H), 3.05 (s, 1H), 2.95–2.85 (m, 1H), 2.62–2.45 (m, 2H), 2.28–2.15 (m, 2H), 2.05–1.88 (m, 2H), 1.78–1.10 (m, 7H), 1.29 (s, 9H).

IR (KBr): 3330, 2925, 2862, 1706, 1661, 1520, 1454, 1246, 738, 694 cm$^{-1}$.

MS (FD): m/e 568 (M$^+$), 467.

Analysis for C$_{32}$H$_{45}$N$_3$O$_4$S: Calcd: C, 67.69; H, 7.99; N, 7.40; Found: C, 67.64; H, 8.20; N, 7.45.

G. [3S-(3R*,4aR*,8aR*,2'S*,3'S*)]-2-[3'-amino-2'-hydroxy- 4'-(phenyl)thio]butyl decahydroisoquinoline-3-N-t-butyl carboxamide The desired subtitled compound was prepared substantially in accordance with the procedure detailed in Procedure 2G using 1 g (1.8 mmol) of the subtitled compound of Preparation 8F and 40 mL of a 30% hydrobromic acid in acetic acid solution, with the exception that the crude material was dissolved in 30 mL of methanol. To the resulting solution, was added 2 mL of diethylamine and 2 mL of concentrated ammonium hydroxide and then the mixture was concentrated under reduced pressure to provide a residue. This residue was redissolved in water and ethyl acetate. The resulting layers were separated and the organic layer was washed sequentially with an aqueous sodium bicarbonate solution and brine, dried over sodium sulfate, filtered and then reduced to dryness under reduced pressure to provide a residue. This residue was purified using flash chromatography (gradient eluent of 0–10% methanol in chloroform (containing 3 drops of ammonium hydroxide per 1000 mL of chloroform) to provide 0.54 g of a white foam.

Yield: 71%. separate $^1$H NMR (CDCl$_3$): δ7.41–7.16 (m, 5H), 6.07 (s, 1H), 3.78–3.70 (m, 1H), 3.45–3.38 (m, 1H), 3.03–2.84 (m, 3H), 2.38–2.20 (m, 3H), 2.00–1.05 (m, 12H), 1.33 (s, 9H).

IR (KBr): 2924, 2862, 1660, 1517, 1454, 1439, 737, 691 cm$^{-1}$.

MS (FD): m/e 434 (M$^+$), 293.

Preparation 9

A. 3-Methoxy-N-phenylbenzamide

A solution of 13.4 mL (147 mmol) of aniline in 30.7 mL of triethylamine was slowly added to a solution containing 25.1 g (147 mmol) of 3-methoxybenzoyl chloride in methylene chloride. The resulting reaction mixture was reacted for approximately thirty minutes and then diluted with 1N sodium bicarbonate. The resultant layers were separated and the organic layer was washed sequentially with water, 1M sodium hydroxide and then brine, dried over sodium sulfate, filtered and then reduced to dryness under reduced pressure to provide 31.6 g of an off-white solid.

Yield: 95%.

B. 3-Methoxy-2-methyl-N-phenylbenzamide

To a cold (–70° C.) solution of 4.54 g (20 mmol) of the subtitled compound of Preparation 9A and 5.11 g (44 mmol) of TMEDA in 70 mL of anhydrous tetrahydrofuran, was added 26.9 mL of a 1.56M solution of n-butyl lithium in hexane. The resultant reaction mixture was warmed to –15° C. and stirred for approximately 45 minutes to provide a yellow slurry. The slurry was then recooled to –70° C. and 2.89 g (20 mmol) of methyl iodide was added, resulting in the formation of a white precipitate. The reaction mixture was stirred overnight at room temperature, quenched with saturated ammonium chloride and diluted with diethylether. The resulting layers were separated and the organic phase washed sequentially with saturated ammonium chloride, water, saturated sodium bicarbonate and brine solutions. The organic extracts were then dried over sodium sulfate and concentrated to provide a white solid which was purified by recrystallization from a 2:1 ethyl acetate/hexane solution to provide 4.00 g of needles.

Yield: 99%.

$^1$H NMR (CDCl$_3$): δ2.36 (s, 3H), 3.88 (s, 3H), 3.89 (s, 1H), 6.90–7.70 (m, 8H).

IR (CHCl$_3$): 3424, 3013, 2963, 2943, 2840, 1678, 1597, 1585, 1519, 1463, 1438, 1383, 1321, 1264, 1240, 1178, 1083, 1069 cm$^{-1}$.

MS(FD): m/e 241 (M$^+$, 100).

Analysis for C$_{15}$H$_{15}$NO$_2$: Calcd: C, 74.67; H, 6.27; N, 5.80; Found: C, 74.65; H, 6.29; N, 5.82.

C. 3-Hydroxy-2-methylbenzoic acid

A mixture of 1.21 g (5.00 mmol) of the subtitled compound of Preparation 9B, 35 mL of 5N hydrochloric acid and 20 mL of a 30% solution of hydrobromic acid in acetic acid were heated at reflux for 24 hours. After cooling, the reaction mixture was diluted with 100 mL of ethyl acetate and 100 mL of water. The resulting layers were separated and the organic layer was washed once with water and then basified to pH 11 using 0.5N sodium hydroxide. The resulting layers were separated and the aqueous layer reacidified to pH 1 using 5N hydrochloric acid. The desired compound was then extracted from this aqueous layer using ethyl acetate. The ethyl acetate extracts were then washed with brine, dried over sodium sulfate, filtered, and then concentrated to provide a residue which after two concentrations from hexane yielded 750 mg of a white solid.

Yield: 98%.

$^1$H NMR (DMSO-d$_6$): δ2.26 (s, 3H), 6.98 (d, J=8.03 Hz, 1H), 7.02 (t, J=7.69 Hz, 1H), 7.15 (d, J=7.37 Hz, 1H), 9.55 (br.s, 1H).

IR (CHCl$_3$): 3600–2100 (br.), 3602, 2983, 1696, 1588, 1462, 1406, 1338, 1279, 1174, 1154, 1075, 1038, 920, 892, 854, 816 cm$^{-1}$.

MS(FD): m/e 152 (M$^+$, 100).

Analysis for C$_8$H$_8$O$_3$: Calcd: C, 63.15; H, 5.30; Found: C, 63.18; H, 5.21.

Alternatively, the desired subtitled compound was prepared by adding 22.6 g (0.33 mol) of sodium nitrite in small portions to a cooled (–10° C.) solution of 45 g (0.30 mol) of 3-amino-2-methylbenzoic acid and 106 g (58 mL; 1.08 mol) of concentrated sulfuric acid in 400 mL of water, while maintaining the temperature below 7° C. The resultant reaction mixture was stirred for approximately 30 minutes at –10° C., poured into a solution of 240 mL of concentrated sulfuric acid in 1.2 L water, and then slowly heated to 80° C. (heavy gas evolution occurs between the temperatures of 40°–60° C.). When the gas evolution stopped, the reaction mixture was cooled to room temperature and the subtitled compound was extracted five times with ethyl acetate (600 mL). The combined organic phases were combined with 500 mL of an aqueous saturated sodium carbonate soluton. The resultant layers were separated and the aqueous layer was acidified to pH 2 with concentrated hydrochloric acid. The titled compound was then extracted using ethyl acetate (500 mL) and the combined organic phases were washed with brine, dried over sodium sulfate, filtered and then concentrated under reduced pressure to provide a crude material. This material was purified using two recrystallizations from a ethyl acetate/chloroform mixture to provide 23.2 g of a light orange powder.

Yield: 52%.

Preparation 10

A. 2-Ethyl-3-methoxy-N-phenylbenzamide

The subtitled compound was prepared substantially in accordance with the procedure detailed in Preparation 9B, using 13.5 mL (21 mmol) of 1.56M n-butyl lithium, 2.27 g (10.0 mmol) of the subtitled compound of Preparation 9A, 2.56 g (22.0 mmol) of TMEDA and 1.56 g (10.0 mmol) of ethyl iodide in 50 mL of anhydrous tetrahydrofuran. The resultant crude material was purified by recrystallization from a 3:1 solution of ethyl acetate/hexane to provide 1.57 g of needles.

Yield: 62%.

$^1$H NMR (CDCl$_3$): δ1.22 (t, J=7.4 Hz, 3H), 2.81 (q, J=7.4 Hz, 2H), 3.88 (s, 3H), 6.96 (d, J=8.2 Hz, 1H), 7.05 (d, J=7.6 Hz, 1H), 7.10–7.45 (m, 4H), 7.50 (s, 1H), 7.62 (d, J=7.95 Hz, 1H).

MS(FD): m/e 255 (M+, 100).

Analysis for C$_{16}$H$_{17}$NO$_2$: Calcd: C, 75.27; H, 6.71; N, 5.49; Found: C, 75.39; H, 6.72; N, 5.43.

B. 2-Ethyl-3-hydroxybenzoic Acid

A solution containing 180 mg (0.71 mmol) of the subtitled compound of Preparation 10A, 3 mL of 5N hydrochloric acid and 3 mL of a 30% solution of hydrobromic acid/acetic acid were heated for 20 hours in a sealed tube at 155° C. After cooling, the reaction mixture was diluted with ethyl acetate and water. The resulting layers were separated and the organic layer was extracted once with water and then basified to pH 11 using 0.5N sodium hydroxide. The resulting layers were separated and the aqueous layer reacidified to pH 1 using 5N hydrochloric acid. The desired compound was then extracted from this aqueous layer using ethyl acetate. The ethyl acetate extracts were washed with brine, dried over sodium sulfate, filtered and then concentrated to provide 103 mg of a pale red solid.

Yield: 88%.

$^1$H NMR (acetone-$d_6$): δ1.16 (t, J=7.4 Hz, 3H), 2.98 (q, J=7.4 Hz, 2H), 7.00–7.15 (m, 2H), 7.32–7.36 (m, 1H), 8.48 (br.s, 1H).

MS(FD): m/e 166 ($M^+$, 100).

Preparation 11

A. 2-Fluoro-3-methoxy-N-phenylbenzamide

The desired subtitled compound was prepared substantially in accordance with the procedure detailed in Preparation 9B, by adding a solution of 3.15 g (10.0 mmol) of N-fluorobenzenesulfonimide in 5 mL of tetrahydrofuran to a solution containing 13.5 mL (21.0 mmol) of 1.56M n-butyl lithium, 2.27 g (10.0 mmol) of the subtitled compound of Preparation 9A and 2.56 g (22.0 mmol) of TMEDA in 50 mL of anhydrous tetrahydrofuran. The resultant crude material was recrystallized twice from a 2:1 solution of ethyl acetate/hexane and then further purified using radial chromatography (6 mm, 0.5% ethyl acetate in methylene chloride) to provide 540 mg of an off-white solid.

Yield: 22%.

$^1$H NMR (CDCl$_3$): δ3.94 (s, 3H), 7.05–7.80 (m, 8H), 8.35–8.50 (m, 1H).

MS(FD): m/e 245 ($H^+$, 100).

B. 2-Fluoro-3-hydroxybenzoic Acid

The subtitled compound was prepared substantially in accordance with the procedure detailed in Preparation 9C, using a solution of 255 mg (1.02 mmol) of the subtitled compound of Preparation 11A, 3 mL of 5N hydrochloric acid and 5 mL of a 30% solution of hydrobromic acid in acetic acid to provide 134 mg of a white solid.

Yield: 86%.

$^1$H NMR (acetone-$d_6$): δ7.05–7.50 (m, 5H).

MS (FD): m/e 156 ($M^+$, 100).

Preparation 12

A. 4-N-(phenyl)carbamoyl pyridine

A solution of 22.8 mL (250 mmol) of aniline in 104.5 mL (750 mmol) of triethylamine was slowly added to a solution of 44.5 g (250 mmol) of 4-chloroformyl pyridinium hydrochloride in 500 mL of chloroform. The resulting reaction mixture was stirred overnight and then refluxed for 2 hours. After cooling, the reaction mixture was diluted with 600 mL of water which resulted in the formation of a precipitate. After adding 200 mL of isopropanol to the mixture, the resultant layers were separated and the organic layer was washed sequentially with 0.1N sodium hydroxide, water and then brine, dried over sodium sulfate, filtered and then concentrated under reduced pressure at 70° C. to provide a white solid with a brown tinge. This solid was washed with 200 mL of ethyl acetate to provide 38.9 g of the desired subtitled compound.

Yield: 78%.

B. 4-N-(Phenyl)carbamoyl pyridine N-oxide

To a hot (85°–90° C.) solution of 19.8 g (100 mmol) of the subtitled compound of Preparation 12A in 60 mL of glacial acetic acid, was slowly added 51 mL of hydrogen peroxide behind a blast shield. The resultant reaction mixture was reacted for approximately four hours at 90° C., cooled to room temperature, diluted in about 60 mL of a mixture of isopropanol and chloroform and then basified to pH 12. The resultant layers were separated and the combined organic extracts were dried over sodium sulfate, filtered and concentrated under reduced pressure to provide a pale yellow solid. This solid was triturated with 250 mL of methylene chloride and reduced to dryness to provide 15.95 g of an off-white solid.

Yield: 75%.

C. 2-Chloro-4-N-(phenyl)carbamoyl pyridine

To a solution of 20.2 g (97.0 mmol) of phosphorus pentachloride in 27 mL (289 mmol) of phosphorous oxychloride, was added 14.4 g (67.2 mmol) of the subtitled compound of Preparation 12B. The resultant reaction mixture was slowly heated to 130° C. and reacted for approximately 40 minutes. The reaction mixture was cooled to room temperature and then concentrated under reduced pressure to provide a residue. This residue was redissolved in 80 mL of water and then diluted with 80 mL of aqueous potassium carbonate resulting in the formation of a yellow precipitate. The precipitate was isolated by filtration, dissolved in 250 mL of hot ethanol and then hot filtered to provide a dark yellow solution. This solution was concentrated under reduced pressure to approximately 160 mL and then hot filtered again before the addition of about 50–60 mL of water. The resultant solution was cooled and the desired compound was isolated by recrystallization to provide 8.0 g of pale yellow and white needles.

Yield: 51%.

D. 2-Methoxy-4-N-(phenyl)carbamoyl pyridine

To a slurry of 4.09 g (18.0 mmol) of the subtitled compound of Preparation 12C in 30 mL of methanol, was added 2.92 g (42.0 mmol) of sodium methoxide. The resultant reaction mixture was refluxed for approximately eighteen hours, cooled and concentrated under reduced pressure to provide a solid. This solid was washed with water and triturated with cold benzene to provide 1.8 g of a solid. Analysis of this solid indicated that the reaction was not complete, so an additional 10.01 g (144 mmol) of sodium methoxide was added to the solid in methanol. The resultant reaction mixture was refluxed in methanol for fifteen hours and worked up identically to provide 300 mg of a solid. This solid was purified using column chromatography (2 mm plate; eluent of 40% ethyl acetate in hexane) followed by recrystallization from hot hexane to provide 140 mg of the desired compound.

Yield: 3%.

E. 2-Methoxy-3-methyl-4-N-(phenyl)carbamoyl pyridine

The subtitled compound was prepared substantially in accordance with the procedure detailed in Preparation 9B, using 260 mg (1.17 mmol) of the subtitled compound of Preparation 12D, 404 µL (2.68 mmol) of TMEDA, 1.78 mL (2.68 mmol) of n-butyl lithium, and 329 µL (5.61 mmol) of methyl iodide in 2 mL of tetrahydrofuran. The crude material was purified using radial chromatography (2 mm plate; eluent of 40% ethyl acetate in hexane) followed by recyrstallization from hot hexane to provide 140 mg of the desired subtitled compound.

F. 3-methyl-2-pyridone-4-carboxylic acid

A slurry of 150 mg (0.598 mmol) of the subtitled compound of Preparation 12E in 4 mL of 5N hydrochloric acid (aqueous) was refluxed for approximately five hours. After cooling, the reaction mixture was concentrated under reduced pressure to provide a yellow oil. This oil was dissolved in 15 mL of water and the resultant solution was adjusted to pH 8 using potassium hydroxide and then diluted with 10 mL of toluene. The resulting layers were separated and the aqueous layer was acidified to pH 3.5 using a 5N hydrochloric acid solution and then concentrated under reduced pressure to provide a yellow solid. This solid was slurried in 2 mL of hot ethanol and filtered through a cotton plug. The filtrate was then reduced to dryness under reduced pressure to provide 130 mg of a solid. This solid was washed with 5 mL of hot 10% acetic acid in ethyl acetate to provide 17 mg of a solid which was then crystallized in ethanol to provide 6.8 mg of the desired subtitled compound.

Yield: 6%.

Preparation 13

2,6-Dichloro-3-hydroxy benzoic acid

Chlorine gas (20 g; 282 mmol) was slowly bubbled through a cold (−70° C.) solution of 20 g (145 mmol) of 3-hydroxy benzoic acid in 100 mL of methanol, under nitrogen, resulting in a temperature increase to about −5° C. The reaction mixture was recooled and after approximately thirty minutes, the chlorine gas was flushed out with nitrogen. The reaction mixture was then warmed to room temperature and diluted with 100 mL of water. The desired titled compound was isolated by recrystallization to provide a white solid. This solid was purified by recyrstallization from 90 mL of water followed by recrystallization from 250 mL of benzene containing 10 mL of acetone to provide 4.8 g of the desired titled compound.

Yield: 16%.

Preparation 14

2-Chloro-3-hydroxy benzoic acid

Chlorine gas (10.3 g; 147 mmol) was slowly bubbled through a cold solution of 20 g (145 mmol) of 3-hydroxy benzoic acid in 100-mL of methanol, under nitrogen, while maintaining the temperature below −60° C. After approximately thirty minutes, the chlorine gas was flushed out with nitrogen and the reaction mixture was allowed to warmed to room temperature and diluted with 100 mL of water. The desired titled compound was isolated by recrystallization to provide a white solid. This solid was purified by recyrstallization from 50 mL of water followed by recrystallization from 130 mL of benzene containing 10 mL of acetone to provide the desired titled compound.

Preparation 15

A. 2-Methyl-3-methoxy benzoate methyl ester

A slurry of 306 mg (2.00 mmol) of the subtitled compound of Preparation 9C, 1.06 mL (20.0 mmol) of methyl iodide and 1.38 g (10.0 mmol) of potassium carbonate in 8 mL of acetone was refluxed for approximately 3 hours. Since the reaction was not complete, an additional 2 mL (37.7 mmol) of methyl iodide, 2 g (14.5 mmol) of potassium carbonate and 10 mL of acetone were added to the reaction mixture. After refluxing the mixture for approximately sixteen hours, the mixture was filtered. The filtrate was then concentrated under reduced pressure to provide a residue. This residue was dissolved in ethyl acetate and washed with water and then reduced to dryness under reduced pressure to provide 188 mg of material which was 88% desired product.

B. 2-Methyl-3-methoxy benzoic acid

A solution of 116 mg (4.86 mmol) of lithium hydroxide in 1 mL of water,was added to a solution of 175 mg (0.97 mmol) of the subtitled compound of Preparation 15A in 3 mL of tetrahydrofuran. The resultant reaction mixture was stirred rapidly. When the reaction was substantially complete, as indicated by TLC, the reaction mixture was concentrated under reduced pressure to provide a residue. This residue was redissolved with 10 mL of hexane, 25 mL of water and 3 mL of 1N sodium hydroxide. The resulting layers were separated and the aqueous layer was diluted with ethyl acetate and then acidifed to pH 1 using 1M hydrochloric acid. The resulting layers were separated and the ethyl acetate layer was washed with brine, dried over sodium sulfate, filtered and reduced to dryness under reduced pressure to provide 73 mg of the desired subtitled compound.

Preparation 16

A. 2-Butyl-3-methoxy-N-phenylbenzamide

The desired subtitled compound was prepared substantially in accordance with the procedure detailed in Preparation 9B, using 11.95 mL of 1.51M of n-butyl lithium in hexanes (18.04 mmol), 1.95 g (8.95 mmol) of the subtitled compound of Preparation 9A, 2.19 g (18.89 mmol) of TMEDA and 1.60 g (9.45 mmol) butyl iodide in 30 mL of anhydrous tetrahydrofuran. The resultant crude material was purified using radial chromatography (4 mm plate; eluent of 15% ethyl acetate in hexane) to provide 83 mg of a clear, colorless oil.

Yield: 3.5%.

$^1$H NMR (CDCl$_3$): δ0.89 (t, J=7.27 Hz, 3H), 1.36 (m, 2H), 1.56 (m, 2H), 2.78 (m, 2H), 3.84 (s, 3H), 6.92 (d, J=7.98 Hz, 1H), 7.00 (d, J=7.36 Hz, 1H), 7.11–7.22 (m, 2H), 7.35 (t, 2H), 7.59 (m, 2H).

IR (CHCl$_3$): 3691, 3619, 3424, 3024, 3010, 2963, 2874, 1679, 1602, 1580, 1517, 145.9, 1437, 1315, 1265, 1177, 1055, 877 cm$^{-1}$.

MS(FD): m/e 283 (M$^+$, 100).

B. 2-Butyl-3-hydroxybenzoic Acid

The desired subtitled compound was prepared substantially in accordance with the procedure detailed in Preparation 10B, using 80 mg (0.28 mmol) of the subtitled compound of Preparation 16A in 2 mL of 5N hydrochloric acid, and 2 mL of 30% hydrobromic acid in acetic acid to provide 44 mg of crude material which was used without further purification.

Yield: 60% (by $^1$H NMR).

$^1$H NMR (CDCl$_3$): δ0.96 (t, J=8.09 Hz, 3H), 1.44 (m, 2H), 1.59 (m, 2H), 3.03 (m, 2H), 6.99 (d, J=8.03 Hz, 1H), 7.15 (t, J=7.77 Hz, 1H), 7.59 (d, J=6.85 Hz, 1H).

Preparation 17

A. 3-Methoxy-2-propyl-N-phenylbenzamide

The desired subtitled compound was prepared substantially in accordance with the procedure detailed in Preparation 9B, using 2.5 g (11.0 mmol) of the subtitled compound of Preparation 9A, 2.81 g (24.2 mmol) of TMEDA, 15.23 mL (23.13 mmol) of n-butyl lithium and 1.33 g (11.0 mmol) of allyl bromide in 30 mL of tetrahydrofuran to provide 2.5 g of crude material. This material was dissolved in 30 mL of absolute ethanol in the presence of 0.5 g of 10% palladium-on-carbon and the resulting mixture was reacted under a hydrogen atmosphere for approximately twelve hours. The mixture was then filtered over celite and the filtrate was concentrated under reduced pressure to provide an orange oil. This oil was purified using radial chromatography (6 mm plate; eluent of 10% ethyl acetate in hexane) to provide 438 mg of a white foam.

Yield: 15%.

$^1$H NMR (CDCl$_3$): δ0.94 (t, J=7.35 Hz, 3H), 1.62 (m, 2H), 2.75 (m, 2H), 3.84 (s, 3H), 6.92 (d, J=8.06 Hz, 1H), 7.00 (d, J=7.39 Hz, 1H), 7.16 (m, 2H), 7.34 (t, 2H), 7.59 (d, 2H), 7.69 (br.s, 1H).

B. 3-Hydroxy-2-propylbenzoic Acid

The desired subtitled compound was prepared substantially in accordance with the procedure detailed in Preparation 10B, using 438 mg (1.62 mmol) of the subtitled compound of Preparation 17A in 7 mL of 5N hydrochloric acid and 7 mL of 30% hydrobromic acid in acetic acid to provide a tan solid. This solid was purified by recrystallization from hot toluene to provide 84 mg of a tan solid.

Yield: 29%.

$^1$H NMR (CDCl$_3$): δ1.01 (t, J=7.33 Hz, 3H), 1.63 (m, 2H), 2.98 (m, 2H), 6.98 (d, J=7.97 Hz, 1H), 7.14 (t, J=7.86 Hz, 1H), 7.57 (d, J=7.28 Hz, 1H).

IR (KBr): 3383, 3047, 2962, 2872, 2641, 1698, 1458, 1412, 1341, 1296, 1278, 1223, 1174, 1086, 929, 815, 752 cm$^{-1}$.

MS(FD): m/e 180 (M$^+$, 100).

Preparation 18

A. 2-Isopropyl-3-methoxybenzonitrile

To a mixture of 2.76 g (0.115 mol) of magnesium in 75 mL of diethylether, was slowly added 24.31 g (0.143 mol) isopropyl iodide. The resulting reaction mixture was allowed to react until all of the magnesium was consumed. then, a solution of 15.0 g (0.92 mol) of 2,3-dimethoxy benzonitrile in 75 mL of diethylether was added over ninety minutes. The resulting reaction mixture was reacted overnight at room temperature and then refluxed for four hours. The resultant reaction mixture was then cooled to 0° C., and the top layer was decanted into saturated ammonium chloride and ice. The resultant layers were separated and the organic layer was washed sequentially with a dilute sodium hydroxide solution, water, and a dilute hydrochloric acid solution, dried over sodium sulfate, filtered and then concentrated to provide an orange oil. This oil was distilled under reduced pressure (5 inch vigreux column; 0.2 mm Hg) to provide 6.25 g of an orange oil.

Yield: 39%.

$^1$H NMR (CDCl$_3$): δ1.37 (d, J=6.47 Hz, 6H), 3.55 (m, 1H), 3.83 (s, 3H), 7.04 (d, J=7.79 Hz, 1H), 7.18 (m, 2H).

IR (CHCl$_3$): 3690, 3617, 3019, 2968, 2939, 2841, 2228, 1577, 1470, 1457, 1440, 1387, 1363, 1265, 1100, 1070, 1045, 878 cm$^{-1}$.

MS(FD): m/e 175 (M$^+$, 100).

B. 3-Hydroxy-2-isopropyl benzoic acid

The desired subtitled compound was prepared substantially in accordance with the procedure detailed in Preparation 10B, using 330 mg (1.88 mmol) of the subtitled compound of Preparation 18A in 2 mL of 5N hydrochloric acid and 30% hydrobromic acid in acetic acid. The crude product was purified using radial chromatography (2 mm plate; eluent of 3% methanol in methylene chloride containing 1% acetic acid) to provide 125 mg of a rose colored solid.

Yield: 37%.

$^1$H NMR (CDCl$_3$): δ1.40 (d, J=6.92 Hz, 6H), 3.62 (m, 1H), 6.83 (d, J=7.86 Hz, 1H), 7.06 (t, J=7.89 Hz, 1H), 7.24 (d, J=7.55 Hz, 1H).

IR (CHCl$_3$): 3599, 3025, 2965, 2876, 1695, 1603, 1584, 1466, 1454, 1404, 1360, 1275, 1234, 1166, 1148, 1086, 1057, 926 cm$^{-1}$.

MS(FD): m/e 180 (M$^+$, 100).

Analysis for C$_{10}$H$_{12}$O$_3$: Calcd: C, 66.65; H, 6.71; Found: C, 66.53; H, 6.84.

Preparation 19

3-methylisonicotinic acid

To a hot (155° C.) solution of 10.7 g (0.1 mol) of 3,4-lutidine in 100 mL diphenylether, was added 18 g (0.16 mol) selenium dioxide in portions. After about 20 minutes, the reaction was heated to 185° C. and allowed to react for approximately thirty minutes. After cooling, the reaction mixture was diluted with water and filtered. The filtrate was extracted with chloroform and the chloroform extracts were then concentrated under reduced pressure to provide 6.0 g of a pale brown solid.

Yield: 44%.

$^1$H NMR (CDCl$_3$): δ2.43 (s, 3H), 7.61 (d, J=4.98 Hz, 1H), 8.49 (d, J=4.99 Hz, 1H), 8.53 (s, 1H).

$^{13}$C NMR (CDCl$_3$): δ17.91, 123.21, 132.81, 138.15, 148.12, 152.71, 167.89 ppm.

IR (KBr): 3425, 2418, 1724, 1606, 1445, 1387, 1303, 1278, 1235, 1100, 1072, 850 cm$^{-1}$.

MS(FD): m/e 138 (M$^+$, 100).

Preparation 20

5-quinolinecarboxylic acid

To a solution containing 15 g (0.1 mol) of m-aminobenzoic acid, 27 g (0.13 mol) of m-nitrobenzene sulfonate and 25 g (0.4 mol) of glycerol, was added 125 g of 70% sulfuric acid. The resultant reaction mixture was refluxed for about 2.5 hours, diluted with 125 mL of water, basified to pH 9 using ammonium hydroxide, stirred overnight with 5 g of charcoal, and then filtered. The filtrate was then boiled with 5 g charcoal, filtered, and then cooled to 50° C., acidified to pH 5 with glacial acetic acid (15 mL), and filtered to provide a brown solid. This solid was boiled in 300 mL of water containing 10 mL of acetic acid and hot filtered to provide crude material. This material was purified using recrystallization from boiling acetic acid to provide 6.1 g of a pale brown solid.

Yield: 32%.

$^1$H NMR (CDCl$_3$): δ7.62 (m, 1H), 7.81 (t, J=7.82 Hz, 1H), 8.20 (m, 2H), 8.93 (d, J=3.79 Hz, 1H), 9.24 (d, J=8.58 Hz, 1H).

IR (KBr): 2772, 2431, 1906, 1708, 1610, 1589, 1507, 1363, 1323, 1269, 1235, 1211, 1141, 1076, 1034, 999, 866, 807 cm$^{-1}$.

MS(FD): m/e 173 (M$^+$, 100).

Preparation 21

1,2,3,4-tetrahydro-5-quinolinecarboxylic acid

A solution containing 1.03 g (5.95 mmol) of the titled compound of Preparation 20, 1.87 g (29.77 mmol) of ammonium formate in 100 nil of ethanol was purged with nitrogen for 10 minutes. To this solution was added 0.5 g of palladium black and the resultant reaction mixture was heated to 65° C. After approximately three hours, the reaction mixture was filtered; the resultant filtrate was concentrated under reduced pressure to provide a residue. This residue was partitioned between water (pH 4) and a solution of 10% isopropanol in chloroform. The resulting layers were separated, and the organic layer was washed with water (pH=4), dried over sodium sulfate, filtered, and concentrated to provide crude material. This material was purified using radial chromatography (2 mm plate; gradient eluent of 5–10% methanol in methylene chloride containing 1% acetic acid) to provide 87 mg of a tan solid.

Yield: 8%.

$^1$H NMR (CDCl$_3$): δ1.04 (m, 2H), 2.16 (t, 2H), 2.40 (m, 2H), 5.81 (d, J=8.05 Hz, 1H), 6.09 (t, J=7.78 Hz, 1H), 6.23 (d, J=7.96 Hz, 1H).

IR(KBr): 3296, 2965, 2929, 1691, 1597, 1474, 1461, 1443, 1350, 1305, 1279, 1236, 1184, 1159, 1106, 1073, 1022, 827 cm$^{-1}$.

MS(FD): m/e 177 (M$^+$, 100).

Analysis for $C_{10}H_{11}NO_2$: Calcd: C, 67.78; H, 6.26; N, 7.90; Found: C, 67.96; H, 6.10; N, 7.88.

Preparation 22

A. 3-Amino-2-methyl benzoate methyl ester

A solution of 10 g (66.2 mmol) of 3-amino-2-methyl benzoic acid and 20 g of p-toluenesulfonic acid monohydrate in 400 mL of methanol was refluxed overnight and then diluted with a mixture of ethyl acetate and 1M potassium carbonate. The resulting layers were cooled and then separated. The organic layer was then washed sequentially with 1M potassium carbonate, and brine, dried over sodium sulfate, filtered and then concentrated to provide 9.23 g of an orange oil.

Yield: 85%.

$^1$H NMR (CDCl$_3$): δ2.34 (s, 3H), 3.73 (br.s, 2H), 3.88 (s, 3H), 6.81 (d, J=7.96 Hz, 1H), 7.05 (t, J=7.78 Hz, 1H), 7.19–7.30 (m, 1H).

IR (CHCl$_3$): 3406, 3027, 3012, 2978, 2953, 1718, 1621, 1467, 1435, 1315, 1301, 1265, 1196, 1159, 1108, 1066, 1045, 810 cm$^{-1}$.

MS(FD): m/e 165 (M$^+$, 100).

B. 3-N-(Methylsulfonyl)amino-2-methyl benzoate methyl ester

To a cold (0° C.) solution of 1.07 g (6.48 mmol) of the subtitled compound of Preparation 22A in 50 mL of anhydrous methylene chloride, was added 1.18 g (6.80 mmol) of methylsulfonic anhydride. The resultant reaction mixture was reacted overnight at room temperature and then diluted with 100 mL of methylene chloride, washed twice with a sodium bicarbonate solution, dried over sodium sulfate, filtered, concentrated, redissolved in hexane and then concentrated again to provide a residue. This residue was then triturated three times in hexane and then reduced to dryness under reduced pressure to provide 1.46 g of a pink solid. This solid was then recrystallized using 20 mL of a 30% hexane/50% ethyl acetate/20% methanol mixture.

Yield: 57%.

$^1$H NMR (DMSO-d$_6$): δ2.25–2.45 (m, 4.5H), 2.97 (s, 1.5H), 3.80 (s, 3H), 7.23–7.63 (m, 3H), 9.24 (s, 1H).

IR (KBr): 3900–2400 (br.), 3298, 1713, 1466, 1320, 1290, 1265, 1248, 1210, 1183, 1156, 1047, 971, 964, 752, 563, 519 cm$^{-1}$.

MS(FD): m/e 243 (M$^+$, 100).

Analysis for $C_{10}H_{13}NO_4S$: Calcd: C, 49.37; H, 5.39; N, 5.76; Found: C, 49.15; H, 5.54; N, 5.80.

C. 3-N-(Methylsulfonyl)amino-2-methyl benzoic acid

The desired subtitled compound was prepared substantially in accordance with the procedure detailed in Preparation 15B, using 400 mg (1.64 mmol) of the subtitled compound of Preparation 22S, and 118 mg (4.93 mmol) of lithium hydroxide in 20 mL of tetrahydrofuran and 8 mL of water, to provide 206 mg of a white solid.

Yield: 55%.

$^1$H NMR (DMSO-d$_6$): δ2.43 (s, 3H), 2.97 (s, 3H), 7.26 (t, J=7.87 Hz, 1H), 7.43 (d, J=7.79 Hz, 1H), 7.60 (d, J=7.17 Hz, 1H).

IR (KBr): 3800–2200 (br.), 3252, 1685, 1404, 1334, 1309, 1277, 1149, 982, 965, 914, 780, 763, 748, 632, 518, 498 cm$^{-1}$.

MS(FD): m/e 243 (M$^+$, 100).

Example 1

[3S-(3R*,4aR*,8aR*,2'S*,3'R*)]-2-[2'-Hydroxy-3'-phenylmethyl- 4'-aza-5'-oxo-5'-(2"-fluoro-3"-hydroxyphenyl)pentyl]decahydroisoquinoline- 3-N-t-butylcarboxamide To a cold (−10° C.) solution containing 80 mg (0.20 mmol) of the subtitled compound of Preparation 1B, 31 mg (0.20 mmol) of Preparation 11B and 27 mg (0.20 mmol) of 1-hydroxybenzotriazole hydrate (HOBT.H$_2$O) in 3 mL of anhydrous tetrahydrofuran, was added 41 mg (0.20 mmol) of 1,3-dicyclohexylcarbodiimide (DCC). The reaction mixture was stirred for 36 hours at room temperature and then concentrated under reduced pressure. The resultant residue was redissolved in ethyl acetate, filtered through celite, washed sequentially with saturated sodium bicarbonate and brine, dried over sodium sulfate, filtered and concentrated. The crude product was purifed using radial chromatography (1 mm plate; gradient eluent of 2–5% methanol in methylene chloride) to provide 79 mg of a white foam.

Yield: 73%.

[α]$_D$ −90.80° (c=0.333, MeOH).

$^1$H NMR (CDCl$_3$): δ1.24 s, 9H), 1.16–2.05 (m, 14H), 2.20–2.40 (m, 2H), 2.55–2.70 (m, 2H), 2.90–3.04 (m, 2H), 3.10–3.25 (m, 1H), 4.03 (br.s, 1H), 4.51 (br.s, 1H), 6.01 (s, 1H), 6.90–7.35 (m, 9H).

IR (CHCl$_3$): 3580, 3550–3100 (br.), 2929, 2865, 1662, 1596, 1521, 1472, 1455, 1394, 1368, 1293, 1157, 1047, 879, 839 cm$^{-1}$.

MS(FD): m/e 540 (M$^+$, 100).

HR MS (FAB): m/e for $C_{31}H_{43}N_3O_4F$: Calcd: 540.3238; Found: 540.3228.

Example 2

[3S-(3R*,4aR*,8aR*,2'S*,3'R*)]-2-[2'-Hydroxy-3'-phenylmethyl- 4'-aza-5'-oxo-5'-(2"-chloro-pyrid-3"-yl)pentyl]decahydroisoquinoline-3-N-t-butylcarboxamide The titled compound was prepared substantially in accordance with the procedure detailed in Example 1, using 80 mg (0.20 mmol) of the subtitled compound of Preparation 1B, 31 mg (0.20 mmol) of 2-chloronicotinic acid, 41 mg (0.20 mmol) of DCC and 27 mg (0.20 mmol) of HOBT.H$_2$O in 3 mL of anhydrous tetrahydrofuran. The crude product was purified using radial chromatography (1 mm plate; gradient eluent of 0–5% methanol in methylene chloride) to provide 58 mg of an off-white foam.

Yield: 54%.

[α]$_D$ −70.64° (c=0.224, MeOH).

$^1$H NMR (CDCl$_3$): δ1.16 (s, 9H), 1.17–2.10 (m, 12H), 2.25–2.37 (m, 2H), 2.52–2.70 (m, 2H), 2.97–3.06 (m, 2H), 3.44–3.53 (m, 2H), 4.05 (br.s, 1H), 4.60–4.70 (m, 1H), 5.64 (s, 1H), 7.18–7.38 (m, 7H), 7.60–7.63 (m, 1H), 8.38–8.40 (m, 1H).

IR (CHCl$_3$): 3618, 3428, 3650–3100 (br.), 2929, 1667, 1583, 1515, 1455, 1401, 1368, 1247, 1071, 1046, 877 cm$^{-1}$.

MS(FD): m/e 541 (M$^+$), 440 (100).

Analysis for $C_{30}H_{41}N_4O_3Cl$: Calcd: C, 66.59; H, 7.64; N, 10.35; Cl, 6.55; Found: C, 66.60; H, 7.58; N, 10.17; Cl, 6.84.

Example 3

[3S-(3R*,4aR*,8aR*,2'S*,3'R*)]-2-[2'-Hydroxy-3'-phenylmethyl- 4'-aza-5'-oxo-5'-(2"-ethyl-3"-hydroxyphenyl)pentyl] decahydroisoquinoline-3-N-t-butylcarboxamide The titled compound was prepared substantially in accordance with the procedure detailed in Example 1, using 80 mg (0.20 mmol) of the subtitled compound of Preparation 1B, 35 mg (0.21 mmol) of the subtitled compound of Preparation 10B, 41 mg (0.20 mmol) of DCC and 27 mg (0.20 mmol) of HOBT.H$_2$O in 3 mL of anhydrous tetrahydrofuran. The crude product was purified using radial chromatography (1 mm plate; gradient eluent of 3–5% methanol in methylene chloride) to provide 71 mg of an off-white foam.

Yield: 65%.

[α]$_D$: −76.29° (c=0.291, MeOH).

$^1$H NMR (CDCl$_3$): δ1.03 (t, J=7.42 Hz, 3H), 1.21 (s, 9H), 1.22–2.10 (m, 11H), 2.24–2.35 (m, 2H), 2.44–2.70 (m, 4H), 2.96–3.05 (m, 2H), 3.26–3.40 (m, 1H), 3.96–4.23 (m, 2H), 4.53 (br.s, 1H), 5.80 (s, 1H), 6.30–6.56 (m, 3H), 6.77 (d, J=7.77 Hz, 1H), 6.88 (t, J=7.75 Hz, 1H), 7.19–7.39 (m, 5H).

IR (CHCl$_3$): 3700–3100 (br.), 3429, 3327, 3011, 2971, 2930, 2867, 1662, 1604, 1585, 1514, 1455, 1394, 1368, 1278, 1155, 1087, 1046, 910 cm$^{-1}$.

MS(FD): m/e 550 (M$^+$, 100).

HR MS(FAB): m/e for C$_{33}$H$_{48}$N$_3$O$_4$: Calcd: 550.3645; Found: 550.3664.

Example 4

[2S-(2R*,2'S*,3'R*)]-1-[2'-Hydroxy-3'-phenylmethyl-4'-aza- 5'-oxo-5'-(2"-methyl-3"-hydroxyphenyl)pentyl]pyrrolidine-2-N-t-butylcarboxamide The titled compound was prepared substantially in accordance with the procedure detailed in Example 1, using 55 mg (0.16 mmol) of the subtitled compound of Preparation 3E, 25 mg (0.16 mmol) of the subtitled compound of Preparation 9B, 33 mg (0.16 mmol) of DCC and 22 mg (0.16 mmol) of HOBT.H$_2$O in 2 mL of anhydrous tetrahydrofuran. The crude product was purified using radial chromatography (1 mm plate; gradient eluent of 4–8% methanol in methylene chloride) to provide 52 mg of a white solid.

Yield: 69%.

[α]$_D$: −72.15° (c=0.211, MeOH).

$^1$H NMR (CD$_3$OD): δ1.33 (s, 9H), 1.70–1.90 (m, 4H), 2.06–2.20 (m, 1H), 2.45–3.30 (m, 8H), 3.60–3.70 (m, 1H), 4.25–4.38 (m, 1H), 6.48 (d, J=8.8 Hz, 1H), 6.74 (d, J=7.7 Hz, 1H), 6.93 (t, J=7.7 Hz, 1H), 7.15–7.32 (m, 5H).

IR (CHCl$_3$): 3600–2700 (br.), 3450, 3255, 2968, 2928, 1653, 1632, 1588, 1513, 1454, 1364, 1291, 1233, 1064, 884, 836 cm$^{-1}$.

MS(FD): m/e 468 (M$^+$, 100).

Analysis for C$_{27}$H$_{37}$N$_3$O$_4$: Calcd: C, 69.35; H, 7.98; N, 8.99. Found: C, 69.54; H, 8.10; N, 9.19.

Example 5

[3S-(3R*,4aR*,8aR*,2'S*,3'R*)]-2-[2'-Hydroxy-3'-phenylmethyl- 4'-aza-5'-oxo-5'-(pyrid-3"-yl-N-oxidyl)pentyl]decahydroisoquinoline-3-N-t-butylcarboxamide The titled compound was prepared substantially in accordance with the procedure detailed in Example 1, using 80 mg (0.20 mmol) of the subtitled compound of Preparation 1B, 28 mg (0.20 mmol) of nicotinic acid N-oxide, 41 mg (0.20 mmol) of DCC and 27 mg (0.20 mmol) of HOBT.H$_2$O in 3 mL of anhydrous tetrahydrofuran. The crude product was purified using radial chromatography (1 mm plate; gradient eluent of 5–10% methanol in methylene chloride) to provide 81 mg of a white foam.

Yield: 76%.

[α]$_D$: −104.39° (c=0.213, MeOH).

$^1$H NMR (DMSO-d$_6$): δ1.19 (s, 9H), 1.19–2.10 (m, 14H), 2.50–2.60 (m, 1H), 2.65–2.79 (m, 1H), 2.95–3.10 (m, 2H), 3.83 (br.s, 1H), 4.22–4.32 (m, 1H), 4.87 (d, J=5.5 Hz, 1H), 7.06–7.11 (m, 1H), 7.17–7.22 (m, 2H), 7.33–7.44 (m, 3H), 7.57 (d, J=8.0 Hz, 1H), 8.26 (d, J=6.4 Hz, 1H), 8.44–8.48 (m, 2H).

IR (CHCl$_3$): 3600–3100 (br.), 3428, 2930, 2864, 1669, 1603, 1515, 1479, 1455, 1432, 1394, 1368, 1300, 1279, 1245, 1135, 1083, 1046, 1017 cm$^{-1}$.

MS(FD): m/e 522 (M$^+$, 100).

Example 6

[2S-(2R*,2'S*,3'R*)]-1-[2'-Hydroxy-3'-phenylmethyl-4'-aza- 5'-oxo-5'-(2"-methyl-3"-hydroxyphenyl)pentyl]piperidine-2-N-t-butylcarboxamide The titled compound was prepared substantially in accordance with the procedure detailed in Example 1, using 100 mg (0.29 mmol) of the subtitled compound of Preparation 4F, 44 mg (0.29 mmol) of the subtitled compound of Preparation 9S, 59 mg (0.29 mmol) of DCC and 39 mg (0.29 mmol) of HOBT.H$_2$O in 5 mL of anhydrous tetrahydrofuran. The crude product was purified using radial chromatography (1 mm plate; gradient eluent of 1.5–7% methanol in methylene chloride) to provide 57 mg of an off-white foam.

Yield: 41%.

[α]$_D$: −58.90° (c=0.163, MeOH).

$^1$H NMR (CD$_3$OD): δ1.29 (s, 9H), 1.50–2.20 (m, 10H), 2.60–2.75 (m, 4H), 3.10–3.35 (m, 4H), 3.85–4.02 (m, 2H), 4.10–4.35 (m, 2H), 4.85 (s, 1H), 3.85–4.02 (m, 2H), 4.10–4.35 (m, 2H), 4.85 (s, 1H), 6.55 (d, J=7.29 Hz, 1H), 6.75 (d, J=7.83 Hz, 1H), 6.90–6.96 (m, 1H), 7.15–7.35 (m, 5H).

IR (CDCl$_3$): 3601, 3600–3100 (br), 3428, 3340, 3008, 2941, 2861, 1661, 1601, 1587, 1514, 1455, 1394, 1367, 1284, 1156, 1086, 1047, 832 cm$^{-1}$.

MS(FD): m/e 482 (M$^+$, 100).

Analysis for C$_{28}$H$_{39}$N$_3$O$_4$: Calcd: C, 69.83; H, 8.16; N, 8.72. Found: C, 69.84; H, 8.46; N, 8.50.

Example 7

[3S-(3R*,4aR*,8aR*,2'S*,3'R*)]-2-[2'-Hydroxy-3'-phenylmethyl- 4'-aza-5'-oxo-5'-(2"-methyl-3"-fluorophenyl)pentyl]decahydroisoquinoline- 3-N-t-butylcarboxamide The titled compound was prepared substantially in accordance with the procedure detailed in Example 1, using 80 mg (0.20 mmol) of the subtitled compound of Preparation 1B, 31 mg (0.20 mmol) of 3-fluoro-2-methylbenzoic acid, 41 mg (0.20 mmol) of DCC and 27 mg (0.20 mmol) of HOBT.H$_2$O in 3 mL of anhydrous tetrahydrofuran. The crude product was purified using radial chromatography (1 mm plate; gradient eluent of 1.5–3% methanol in methylene chloride) to provide 40 mg of a white foam.

Yield: 37%.

[α]$_D$: −80.10° (c=0.132, MeOH).

$^1$H NMR (CDCl$_3$): δ1.13 (s, 9H), 1.13–2.10 (m, 16H), 2.20–2.35 (m, 2H), 2.50–2.70 (m, 2H), 2.95–3.05 (m, 2H), 3.53–3.58 (m, 1H), 3.98 (s, 1H), 4.03–4.10 (m, 1H), 5.68 (s, 1H), 6.83–7.07 (m, 3H), 7.10–7.40 (m, 5H).

IR (CHCl$_3$): 3650–3150 (br), 3429, 3030, 3008, 2930, 2863, 1672, 1608, 1514, 1455, 1394, 1368, 1277, 1046, 910, 830 cm$^{-1}$.

MS(FD): m/e 538 (M$^+$, 100).

HR MS(FAB): m/e for C$_{32}$H$_{45}$N$_3$O$_3$F: Calcd: 538.3445; Found: 538.3469.

Example 8

[3S-(3R*,4aR*,8aR*,2'S*,3'R*)]-2-[2'-Hydroxy-3'-phenylmethyl- 4'-aza-5'-oxo-5'-(2"-chloro-3",5"-dihydroxyphenyl)pentyl]decahydroisoquinoline- 3-N-t-butylcarboxamide The titled compound was prepared substantially in accordance with the procedure detailed in Example 1, using 100 mg (0.25 mmol) of the subtitled compound of Preparation 1B, 47 mg (0.25 mmol) of 2-chloro-3,5-dihydroxy benzoic acid, 51 mg (0.25 mmol) of DCC and 34 mg (0.25 mmol) of HOBT.H$_2$O in 2 mL of anhydrous tetrahydrofuran. The crude product was purified using radial chromatography (2 mm plate; gradient eluent of 2–10% methanol in methylene chloride) to provide 47 mg of a white solid.

Yield: 33%.

$[\alpha]_D$: −53.79° (c=0.097, MeOH).

$^1$H NMR (CDCl$_3$): δ0.5–3.10 (m, 32H), 3.70–4.60 (m, 2H), 6.00–7.50 (m, 8H).

IR (CHCl$_3$): 3700–3100 (br.), 2930, 2865, 1658, 1604, 1521, 1455, 1368, 1246, 1156, 1047, 1014, 856 cm$^{-1}$.

MS(FD): 572 (M$^+$, 100).

Analysis for C$_{31}$H$_{42}$N$_3$O$_5$Cl: Calcd: C, 65.08; H, 7.40; N, 7.34. Found: C, 65.30; H, 7.35; N, 7.43.

Example 9

[3S-(3R*,4aR*,8aR*,2'S*,3'R*)]-2-[2'-Hydroxy-3'-phenyl-methyl- 4'-aza-5'-oxo-5'-(2"-methyl-3",5"-diaminophenyl-)pentyl]decahydroisoquinoline- 3-N-t-butylcarboxamide The titled compound was prepared substantially in accordance with the procedure detailed in Example 1, using 100 mg (0.25 mmol) of the subtitled compound of Preparation 1B, 41 mg (0.25 mmol) of 3,5-diamino-2-methyl benzoic acid, 51 mg (0.25 mmol) of DCC and 34 mg (0.25 mmol) of HOBT.H$_2$O in 2 mL of anhydrous tetrahydrofuran and 0.5 mL of dimethylformamide. The crude product was purified using radial chromatography (1 mm plate; gradient eluent of 1–10% methanol in methylene chloride) to provide mg of a light orange foam.

Yield: 22%

$[\alpha]_D$ −89.27° (c=0.137, MeOH).

$^1$H NMR (CDCl$_3$): δ1.21 (s, 9H), 1.30–2.02 (m, 16H), 2.19–2.35 (m, 2H), 2.48–2.70 (m, 2H), 2.90–3.07 (m, 2H), 3.10–3.23 (m, 1H), 3.50 (br.s, 4H), 3.94 (br.s, 1H), 4.40–4.50 (m, 1H), 5.70 (s, 1H), 5.89–5.95 (m, 2H), 6.30 (d, J=8.4 Hz, 1H), 7.15–7.33 (m, 5H).

IR (CHCl$_3$): 3600–3100 (br), 3029, 3005, 2928, 2865, 1664, 1621, 1513, 1455, 1392, 1367, 1276, 1244, 1171, 1047, 841 cm$^{-1}$.

MS(FD): m/e 550 (M$^+$, 100).

HR MS(FAB): m/e for C$_{32}$H$_{48}$N$_5$O$_3$: Calcd: 550.3757; Found: 550.3762.

Example 10

[3S-(3R*,4aR*,8aR*,2'S*,3'R*)]-2-[2'-Hydroxy-3'-phenyl-methyl-4'-aza-5'-oxo-5'-(2"-methyl-3",5"-dinitrophenyl-)pentyl]decahydroisoquinoline- 3-N-t-butylcarboxamide The titled compound was prepared substantially in accordance with the procedure detailed in Example 1, using 100 mg (0.25 mmol) of the subtitled compound of Preparation 1B, 56 mg (0.25 mmol).of 3,5-dinitro-2-methyl benzoic acid, 51 mg (0.25 mmol) of DCC and 34 mg (0.25 mmol) of HOBT.H$_2$O in 3 mL of anhydrous tetrahydrofuran. The crude product was purified using radial chromatography (1 mm plate; gradient eluent of 0–3% methanol in methylene chloride) to provide 61 mg of an off-white foam.

Yield: 41%.

$[\alpha]_D$ −105.96° (c=0.302, MeOH).

$^1$H NMR (CDCl$_3$): δ1.02 (s, 9H), 1.02–2.60 (m, 20H), 2.90–3.06 (m, 2H), 3.21 (br.s, 1H), 3.60–3.75 (m, 1H), 4.05–4.20 (m, 1H), 4.65–4.80 (m, 1H), 5.47 (s, 1H), 7.20–7.50 (m, 5H), 8.00–8.20 (m, 2H), 8.56 (s, 1H).

IR (CHCl$_3$): 3621, 3500–3100 (br), 3428, 3024, 2977, 2931, 1665, 1615, 1539, 1455, 1347, 1278, 1245, 1047, 878 cm$^{-1}$.

MS(FD): m/e 610 (M$^+$, 100).

HR MS(FAB): m/e for C$_{32}$H$_{44}$N$_5$O$_7$: Calcd: 610.3241; Found: 610.3240.

Example 11

[3S-(3R*,4aR*,8aR*,2'S*,3'R*)]-2-[2'-Hydroxy-3'-phenyl-methyl- 4'-aza-5'-oxo-5'-(2"-chloro-3"-hydroxymethyl)pentyl]decahydroisoquinoline- 3-N-t-butylcarboxamide The titled compound was prepared substantially in accordance with the procedure detailed in Example 1, using 116 mg (0.29 mmol) of the subtitled compound of Preparation 1B, 50 mg (0.29 mmol) of the titled compound of Preparation 14, 60 mg (0.29 mmol) of DCC and 39 mg (0.29 mmol) of HOBT.H$_2$O in 4 mL of anhydrous tetrahydrofuran. The crude product was purified using radial chromatography (1 mm plate; gradient eluent of 2.5–5% methanol in methylene chloride) to provide 83 mg of a white solid.

Yield: 51%.

$[\alpha]_D$ −74.29° (c=0.140, MeOH).

$^1$H NMR (CDCl$_3$): δ1.19 (s, 9H), 1.19–2.80 (m, 16H), 2.90–3.15 (m, 2H), 3.35 (br.s, 1H), 4.06 (br.s, 1H), 4.56 (br.s, 1H), 5.85 (br.s, 1H), 6.60–6.70 (m, 1H), 6.90–7.35 (m, 8H).

IR (CHCl$_3$): 3621, 3600–3100 (br), 3429, 2977, 2929, 1671, 1584, 1515, 1445, 1394, 1368, 1292, 1182, 1046, 878, 823 cm$^{-1}$.

MS(FD): m/e 556 (M$^+$, 100).

Analysis for C$_{31}$H$_{42}$N$_3$O$_4$Cl: Calcd: C, 66.95; H, 7.61; N, 7.56. Found: C, 66.76; H, 7.72; N, 7.69.

Example 12

[3S-(3R*,4aR*,8aR*,2'S*,3'R*)]-2-[2'-Hydroxy-3'- phenyl-methyl-4'-aza-5'-oxo-5'-(2"-methyl-3"-hydroxyphenyl)pentyl]decahydroisoquinoline-3-N-t-butylcarboxamide The titled compound was prepared substantially in accordance with the procedure detailed in Example 1, using 261 mg (0.65 mmol) of the subtitled compound of Preparation 1B, 100 mg (0.65 mmol) of the subtitled compound of Preparation 9B, 134 mg (0.65 mmol) of DCC and 88 mg (0.65 mmol) of HOBT.H$_2$O in 6 mL of anhydrous tetrahydrofuran and 0.2 mL of anhydrous dimethylformamide. The crude product was purified using radial chromatography (2 mm plate; gradient eluent of 1–5% methanol in methylene chloride) to provide 304 mg of a white solid.

Yield: 87%.

$[\alpha]_D$ −75.00° (c=0.200, MeOH).

$^1$H NMR (CDCl$_3$): δ1.18 (s, 9H), 1.19–2.05 (m, 18H), 2.20–2.35 (m, 2H), 2.50–2.70 (m, 2H), 2.90–3.05 (m, 2H), 3.22–3.35 (m, 1H), 3.96–4.05 (m, 1H) 4.45–4.55 (m, 1H), 5.77 (s, 1H), 6.53 (d, J=7.4 Hz, 2H), 6.75 (d, J=7.8 Hz, 1H), 6.85–6.90 (m, 1H), 7.15–7.35 (m, 6H).

IR (CHCl$_3$): 3606, 3600–3100 (br.), 3429, 3011, 2929, 2865, 1663, 1604, 1587, 1514, 1455, 1367, 1277, 1200, 1156, 1046, 910 cm$^{-1}$.

MS(FD): m/e 537 (M$^+$, 100).

HR MS(FAB): m/e for C$_{32}$H$_{46}$N$_3$O$_4$: Calcd: 536.3488; Found: 536.3488.

Example 13

[3S-(3R*,4aR*,8aR*,2'S*,3'R*)]-2-[2'-Hydroxy-3'-phenyl-methyl-4'-aza-5'-oxo-5'-(2"-methyl-3"-methoxyphenyl)pentyl]decahydroisoquinoline- 3-N-t-butylcarboxamide The titled compound was prepared substantially in accordance with the procedure detailed in Example 1, using 80 mg (0.20 mmol) of the subtitled compound of Preparation 1B, 33 mg (0.20 mmol) of the subtitled compound of Preparation 15B, 41 mg (0.20 mmol) of DCC and 27 mg (0.20 mmol) of HOBT.H$_2$O in 2 mL of anhydrous tetrahydrofuran. The crude product was purified using radial chromatography (2 mm plate; eluent of 2.5% methanol in methylene chloride) to provide 93 mg of a white foam.

Yield: 84%.

$^1$H NMR (CDCl$_3$): δ1.17 (s, 9H), 1.17–2.05 (m, 12H), 2.05 (s, 3H), 2.25–2.38 (m, 2H), 2.50–2.75 (m, 2H), 2.95–3.10 (m, 2H), 3.35–3.50 (m, 1H), 3.79 (s, 3H), 3.98–4.15 (m, 2H), 4.59–4.65 (m, 1H), 5.72 (s, 1H), 6.47 (br.d, J=8.21 Hz, 1H), 6.63 (d, J=7.7 Hz, 1H), 6.82 (d, J=8.12 Hz, 1H), 7.08 J=7.0 Hz, 1H), 7.15–7.45 (m, 5H).

Analysis for C$_{33}$H$_{47}$N$_3$O$_4$: Calcd: C, 72.10; H, 8.62; N, 7.64. found: C, 71.84; H, 8.49: N, 7.67.

Example 14

[3S-(3R*,4aR*,8aR*,2'S*,3'R*)]-2-[2'-Hydroxy-3'-phenylmethyl-4'-aza-5'-oxo-5'-(2",3"-dichlorophenyl)pentyl]decahydroisoquinoline-3-N-t-butylcarboxamide The titled compound was prepared substantially in accordance with the procedure detailed in Example 1, using 80 mg (0.20 mmol) of the subtitled compound of Preparation 1B, 38 mg (0.20 mmol) of 2,3-dichloro benzoic acid, 41 mg (0.20 mmol) of DCC and 27 mg (0.20 mmol) of HOBT.H$_2$O in 3 mL of anhydrous tetrahydrofuran. The crude product was purified using radial chromatography (2 mm plate; gradient eluent of 2.5–5% methanol in methylene chloride) to provide 95 mg of a white foam.

Yield: 84%.

$^1$H NMR (CDCl$_3$): δ1.16 (s, 9H), 1.17–2.05 (m, 12H), 2.20–2.38 (m, 2H), 2.50–2.75 (m, 2H), 2.95–3.10 (m, 2H), 3.40–3.55 (m, 1H), 3.69 (s, 1H), 4.00–4.10 (m, 1H), 4.58–4.72 (m, 1H), 5.77 (s, 1H), 6.98–7.47 (m, 9H).

MS(FD): m/e 574 (M$^+$), 473 (100).

Example 15

[3S-(3R*,4aR*,8aR*,2'S*,3'R*)]-2-[2'-Hydroxy-3'-phenylmethyl- 4'-aza-5'-oxo-5'-(2"-trifluoromethylphenyl)pentyl]decahydroisoquinoline- 3-N-t-butylcarboxamide The titled compound was prepared substantially in accordance with the procedure detailed in Example 1, using 80 mg (0.20 mmol) of the subtitled compound of Preparation 1B, 38 mg (0.20 mmol) of 2-trifluoromethyl benzoic acid, 41 mg (0.20 mmol) of DCC and 27 mg (0.20 mmol) of HOBT.H$_2$O in 3 mL of anhydrous tetrahydrofuran. The crude product was purified using radial chromatography (2 mm plate; gradient eluent of 2.5–5% methanol in methylene chloride) to provide 72 mg of a white foam.

Yield: 63%.

$^1$H NMR (CDCl$_3$): δ1.10 (s, 9H), 1.16–2.05 (m, 14H), 2.15–2.35 (m, 2H), 2.45–2.70 (m, 2H), 2.92–3.05 (m, 2H), 3.38–3.55 (m, 1H), 3.70 (br.s, 1H), 3.98–4.10 (m, 1H), 4.58–4.70 (m, 1H), 5.90 (s, 1H), 7.00–7.65 (m, 10H).

MS(FD): m/e 573 (M$^+$, 100).

Analysis for C$_{32}$H$_{42}$N$_3$O$_3$F$_3$: Calcd: C, 67.00; H, 7.38; N, 7.32. Found: C, 67.11; H, 7.09; N, 7.10.

Example 16

[3S-(3R*,4aR*,8aR*,2'S*,3'R*)]-2-[2'-Hydroxy-3-phenylmethyl- 4'-aza-5'-oxo-5'-(2"-oxo-3"-methyl-pyrid-4"-yl-)pentyl]decahydroisoquinoline- 3-N-t-butylcarboxamide The titled compound was prepared substantially in accordance with the procedure detailed in Example 1, using 14.7 mg (0.037 mmol) of the subtitled compound of Preparation 1B, 5.6 mg (0.037 mmol) of the subtitled compound of Preparation 12F, 7.6 mg (0.037 mmol) of DCC and 4.9 mg (0.037 mmol) of HOBT.H$_2$O in 1.3 mL of anhydrous dimethylformamide. The crude product was purified using radial chromatography (1 mm plate; eluent of 10% methanol in methylene chloride) to provide 6.5 mg of a white solid.

Yield: 34%.

$^1$H NMR (CDCl$_3$): δ1.00–3.40 (m, 32H), 4.00–4.70 (m, 3H), 5.90–6.10 (m, 1H), 6.90–7.40 (m, 8H).

MS(FD): m/e 537 (M$^+$, 100).

Example 17

[3S-(3R*,4aR*,8aR*,2'S*,3'R*)]-2-[2'-Hydroxy-3'-phenylmethyl- 4'-aza-5'-oxo-5'-(2",6"-dichloro-3"-hydroxyphenyl)pentyl]decahydroisoquinoline- 3-N-t-butylcarboxamide The titled compound was prepared substantially in accordance with the procedure detailed in Example 1, using 48 mg (0.12 mmol) of the subtitled compound of Preparation 1B, 25 mg (0.12 mmol) of the subtitled compound of Preparation 13, 2.5 mg (0.12 mmol) of DCC and 16 mg (0.12 mmol) of HOBT.H$_2$O in 2 mL of anhydrous tetrahydrofuran. The crude product was purified using radial chromatography (1 mm plate; gradient eluent of 2–5% methanol in methylene chloride) to provide 14 mg of the desired titled compound.

$^1$H NMR (CDCl$_3$): δ0.9–2.15 (m, 23H), 2.22–2.85 (m, 4H), 2.95–3.10 (m, 2H), 3.30–3.58 (m, 1H), 3.98–4.12 (m, 1H), 4.56–4.75 (m, 1H), 5.60–5.82 (m, 1H), 6.60–6.79 (m, 1H), 6.90–7.40 (m, 6H).

IR (CHCl$_3$): 3010, 2937, 1644, 1606, 1605, 1497, 1474, 1454, 1433, 1417, 1341, 1313, 1274, 1252, 1161, 1093, 1074, 1027, 991 cm$^{-1}$.

MS(FD): m/e 590 (M$^+$, 100).

Example 18

[3S-(3R*,4aR*,8aR*,2'S*,3'R*)]-2-[2'-Hydroxy-3'-phenylmethyl- 4'-aza-5'-oxo-5'-(2"-methyl-3"-aminophenyl)pentyl]decahydroisoquinoline- 3-N-t-butylcarboxamide The titled compound was prepared substantially in accordance with the procedure detailed in Example 1, using 100 mg (0.25 mmol) of the subtitled compound of Preparation 1B, 38 mg (0.25 mmol) of 3-amino-2-methyl benzoic acid, 34 mg (0.25 mmol) of HOBT.H$_2$O, 52 mg (0.25 mmol) of DCC in 3 mL of anhydrous tetrahydrofuran, with the exception that the reaction was conducted in the presence of 76 mg (0.75 mmol) of triethylamine. The resultant material was purified using radial chromatography (2 mm plate; gradient eluent of 2–5% methanol in methylene chloride) to provide 78 mg of an off-white foam.

Yield: 58%.

$^1$H NMR CDCl$_3$): δ1.19 (s, 9H), 1.20–2.08 (m, 15H), 2.20–2.35 (m, 2H), 2.50–2.70 (m, 2H), 2.92–3.05 (m, 2H), 3.28–3.38 (m, 1H), 3.61 (br.s, 1H), 3.93–4.20 (m, 2H), 4.45–4.58 (m, 1H), 5.80 (s, 1H), 6.44 (d, J=7.5 Hz, 2H), 6.63 (d, J=7.9 Hz, 1H ), 6.90 (t, J=7.7 Hz, 1H), 7.17–7.36 (m, 6H).

MS (FD): m/e 535 (M$^+$, 100).

Example 19

[2S-(2R*,2'S*,3'S*)]-1-[2'-Hydroxy-3'-phenylthiomethyl-4'-aza- 5'-oxo-5'-(3"-hydroxy-2"-methylphenyl)pentyl]-4-pyrid-3"-ylmethyl piperazine-2-N-t-butylcarboxamide The titled compound was prepared substantially in accordance with the procedure detailed in Example 1, using 50 mg (0.11 mmol) of the subtitled compound of Preparation 6B, 16 mg (0.11 mmol) of the subtitled compound of Preparation 9C, 14 mg (0.11 mmol) of HOBT.H$_2$O and 22 mg (0.11 mmol) of DCC in 2 mL of anhydrous tetrahydrofuran. The resultant material was purified using radial chromatography (1 mm plate; gradient eluent of 5–10% methanol in methylene chloride) to provide 35 mg of an off-white foam.

Yield: 55%.

$^1$H NMR (CDCl$_3$): δ1.29 (s, 9H), 2.18 (s, 3H), 2.23–2.33 (m, 1H), 2.45–2.85 (m, 7H), 3.20–3.35 (m, 3H), 3.45 (s, 1H), 4.00–4.10 (m, 1H), 4.25–4.35 (m, 1H), 5.00–5.40 (br.s, 1H), 6.61 (d, J=7.6 Hz, 1H), 6.76–6.80 (m, 2H), 6.92 (t, J=7.7 Hz, 1H), 7.12–7.43 (m, 7H), 7.57–7.62 (m, 1H), 7.78 (br.s, 1H), 8.48–8.58 (m, 2H).

MS (FD): m/e 606 (M$^+$, 100).

Example 20

[3S-(3R*,4aR*,8aR*,2'S*,3'R*)]-2-[2'-Hydroxy-3'-phenylmethyl- 4'-aza-5'-oxo-5'-(2"-isopropyl-3"-hydroxyphenyl)pentyl]decahydroisoquinoline- 3-N-t-butylcarboxamide The titled compound was prepared substantially in accordance with the procedure detailed in Example 1, using 55 mg (0.137 mmol) of the subtitled compound of Preparation 1B, 24.7 mg (0.137 mmol) of the subtitled compound of Preparation 18B, 28.25 mg (0.137 mmol) of DCC, and 18.5 mg (0.137 mmol) of HOBT.H$_2$O in 8 mL of tetrahydrofuran. The resultant crude material was purified using radial chromatography (1 mm plate; eluent of 3% methanol in methylene chloride) to provide 46 mg of a white foam.

Yield: 60%.

[α]$_D$ –84.61 (c=2.60, MeOH).

$^1$H NMR (CDCl$_3$): δ1.19 (d, J=3.7 Hz, 3H), 1.21 (d, J=3.75 Hz, 3H), 1.23 (s, 9H), 1.27–1.51 (m, 7H), 1.61–2.00 (m, 6H), 2.26–2.35 (m, 2H), 2.56–2.65 (m, 2H), 2.91–3.03 (m, 3H), 3.19–3.27 (m, 1H), 3.96 (m, 1H), 4.51 (m, 1H), 5.82 (br.s, 1H), 5.93 (br.s, 1H), 6.23 (d, J=8.53 Hz, 1H), 6.46 (d, J=7.15 Hz, 1H), 6.66 (d, J=7.17 Hz, 1H), 6.86 (t, J=7.74 Hz, 1H), 7.21–7.31 (m, 5H).

IR (CDCl$_3$): 3427, 3322, 3028, 3008, 2930, 2868, 1660, 1603, 1582, 1513, 1455, 1393, 1366, 1304, 1278, 1245, 1088, 1059 cm$^{-1}$.

MS(FD): m/e 564 (M$^+$, 100).

Analysis for C$_{34}$H$_{49}$N$_3$O$_4$: Calcd: C, 72.43; H, 8.76; N, 7.45; Found: C, 72.13; H, 8.85; N, 7.30.

Example 21

[3S-(3R*,4aR*,8aR*,2'S*,3'R*)]-2-[2'-Hydroxy-3'-phenylmethyl- 4'-aza-5'-oxo-5'-(2"-butyl-3"-hydroxyphenyl)pentyl]decahydroisoquinoline- 3-N-t-butylcarboxamide The titled compound was prepared substantially in accordance with the procedure detailed in Example 1, using 91 mg (0.227 mmol) of the subtitled compound of Preparation 1B, 44 mg (0.227 mmol) of the subtitled compound of Preparation 16B, 46.7 mg (0.227 mmol) DCC, and 30.6 mg (0.227 mmol) of HOBT.H$_2$O in 10 mL of tetrahydrofuran. The resultant crude material was purified using radial chromatography (1 mm plate; gradient eluent of 4–7% methanol in methylene chloride) to provide 72 mg of a white foam.

Yield: 55%.

[α]$_D$ –77.36 (c=0.36, MeOH).

$^1$H NMR (CDCl$_3$): δ0.84 (t, J=7.2 Hz, 3H), 1.20 (s, 9H), 1.29–2.00 (m, 18H), 2.27 (m, 2H), 2.48–2.69 (m, 4H), 2.99 (m, 2H), 3.29 (m, 1H), 3.99 (m, 1H), 4.49 (m, 1H), 5.85 (s, 1H), 6.45 (m, 1H), 6.75 (d, J=7.19 Hz, 1H), 6.86 (t, J=7.67 Hz, 1H), 7.21–7.31 (m, 5H).

IR (KBr): 3303 (br.), 3087, 3029, 2927, 2862, 1647, 1583, 1520, 1455, 13 66, 1281, 1209, 1108, 735, 698 cm$^{-1}$.

MS(FD): m/e 578 (M$^+$, 100).

HR MS(FAB): m/e for C$_{35}$H$_{51}$N$_3$O$_4$: Calcd: 578.3958; Found: 578.3962.

Example 22

[3S-(3R*,4aR*,8aR*,2'S*,3'R*)]-2-[2'-Hydroxy-3'-phenylmethyl- 4'-aza-5'-oxo-5'-(2"-propyl-3"-hydroxyphenyl)pentyl]decahydroisoquinoline- 3-N-t-butylcarboxamide The titled compound was prepared substantially in accordance with the procedure detailed in Example 1, using 67 mg (0.167 mmol) of the subtitled compound of Preparation 1B, 30 mg (0.167 mmol) of the subtitled compound of Preparation 17B, 34 mg (0.167 mmol) of DCC, and 23 mg (0.167 mmol) of HOBT.H$_2$O in 4 mL of tetrahydrofuran. The resultant crude material was purified using radial chromatography (1 mm plate; eluent of 3% methanol in methylene chloride) to provide 75 mg of a white foam.

Yield: 80%.

[α]$_D$ –43.75 (c=0.160, MeOH).

$^1$H NMR (CDCl$_3$): δ0.87 (t, 3H), 1.18 (s, 9H), 1.21–2.04 (m, 15H), 2.24–2.33 (m, 2H), 2.49–2.58 (m, 3H), 2.66 (m, 1H), 2.98 (m, 2H), 3.37 (m, 1H), 3.99 (m, 1H), 4.52 (m, 1H), 5.07 (m, 1H), 5.70 (s, 1H), 6.43 (d, J=8.32 Hz, 1H), 6.56 (d, J=7.32 Hz, 1H), 6.76 (d, J=7.12 Hz, 1H), 6.95 (t, J=7.78 Hz, 1H), 7.20–7.33 (m, 5H).

IR (KBr): 3287 (br.), 3086, 2932, 2868, 1681, 1558, 1456, 1368, 1334, 1291, 1261, 1218, 1169, 1101, 1042, 776, 734, 552 cm$^{-1}$.

MS(FD): m/e 564 (M$^+$, 100).

HR MS(FAB): m/e for C$_{34}$H$_{50}$N$_3$O$_4$: Calcd: 564.3801; Found: 564.3789.

Example 23

[3S-(3R*,4aR*,8aR*,2'S*,3'S*)]-2-[2'-Hydroxy-3'-phenylthiomethyl-4'-aza-5'-oxo-5'-(2"-methyl-3"-hydroxyphenyl)pentyl]decahydroisoquinoline- 3-N-t-butylcarboxamide The titled compound was prepared substantially in accordance with the procedure detailed in Example 1, using 70 mg (0.16 mmol) of the subtitled compound of Preparation 8G, 24.6 mg (0.16 mmol) of the subtitled compound of Preparation 9C, 33 mg (0.16 mmol) of DCC, and 22 mg (0.16 mmol) of HOBT.H$_2$O in 4 mL of tetrahydrofuran. The resultant crude material was purified using radial chromatography (1 mm plate; eluent of 3% methanol in methylene chloride) to provide 54 mg of a white foam.

Yield: 60%.

[α]$_D$ –119.23 (c=0.26, MeOH).

$^1$H NMR (CDCl$_3$): δ1.09 (s, 9H), 1.12–1.79 (m, 12H), 1.93–2.02 (m, 2H), 2.17–2.30 (m, 2H), 2.31 (s, 3H), 2.43–2.61 (m, 2H), 2.91 (m, 1H), 3.42 (m, 1H), 3.78 (m, 1H), 4.07 (m, 1H), 4.47 (m, 1H), 5.37 (m, 1H), 5.51 (br.s, 1H), 6.84 (m, 1H), 7.06 (m, 2H), 7.17–7.32 (m, 4H), 7.45 (m, 2H).

IR (KBr): 3297, 2925, 2862, 1627, 1586, 1530, 1482, 1466, 1439, 1366, 1287, 1221, 1156, 1119, 1026, 801, 735, 689 cm$^{-1}$.

MS(FD): m/e 568 (M$^+$, 100).

HR MS(FAB) for C$_{32}$H$_{46}$N$_3$O$_4$S: Calcd: 568.3209; Found: 568.3182.

Example 24

[3S-(3R*,4aR*,8aR*,2'S*,3'S*)]-2-[2'-Hydroxy-3'-(naphth-2-ylthiomethyl)-4'-aza-5'-oxo-5'-(2"-methyl-3"-hydroxyphenyl)pentyl]decahydroisoquinoline- 3-N-t-butylcarboxamide The titled compound was prepared substantially in accordance with the procedure detailed in Example 1, using 70 mg (0.145 mmol) of the subtitled compound of Preparation 7B, 22 mg (0.145 mmol) of the subtitled compound of Preparation 9C, 29 mg (0.145 mmol) of DCC, and 19 mg (0.145 mmol) of HOBT.H$_2$O in 4 mL of tetrahydrofuran. The resultant crude material was purified using flash chromatography (gradient eluent of 5–15% acetone in methylene chloride) to provide 65 mg of a white solid.
 Yield: 73%.
 $[\alpha]_D$ −112.00 (c=0.25, MeOH).
 $^1$H NMR (CDCl$_3$): δ1.10 (s, 9H), 1.15–1.80 (m, 12H), 1.93–2.06 (m, 1H), 2.17–2.28 (m, 2H), 2.29 (s, 3H), 2.42–2.61 (m, 2H), 2.94 (d, 1H), 3.51 (m, 1H), 3.83–3.92 (m, 1H), 4.10 (m, 1H), 5.36 (br.s, 1H), 5.53 (br.s, 1H), 6.79 (m, 1H), 6.93 (m, 2H), 7.21 (d, J=8.83 Hz, 1H), 7.40–7.53 (m, 3H), 7.73 (m, 3H), 7.90 (s, 1H).
 IR (KBr): 3427, 3311 (br), 2929, 2864, 1703, 1661, 1587, 1514, 1456, 1393, 1366, 1276, 1200, 1177, 1146, 1119, 1070, 1042 cm$^{-1}$.
 MS(FD): m/e 618 (M$^+$, 100).
 Analysis for C$_{34}$H$_{49}$N$_3$O$_4$: Calcd: C, 69.98; H, 7.67; N, 6.80. Found: C, 69.92; H, 7.72; N, 6.75.

Example 25

[2S-(2R*,2'S*,3'S*)]-1-[2'-Hydroxy-3'-(naphth-2-ylthiomethyl)- 4'-aza-5'-oxo-5'-(2"-methyl-3"-hydroxyphenyl)pentyl]piperidine- 2-N-t-butylcarboxamide The titled compound was prepared substantially in accordance with the procedure detailed in Example 1, using 28 mg (0.065 mmol) of the subtitled compound of Preparation 2G, 10 mg (0.065 mmol) of the subtitled compound of Preparation 9C, 13.5 mg (0.065 mmol) of DCC, and 9 mg (0.065 mmol) HOBT.H$_2$O in 2 mL of tetrahydrofuran. The resultant crude material was purified using radial chromatography (1 mm plate; eluent of 2% methanol in methylene chloride) to provide 23 mg of a white foam.
 Yield: 63%.
 $[\alpha]_D$ −233.33 (c=0.09, MeOH).
 $^1$H NMR (CDCl$_3$): δ1.17 (s, 9H), 1.26 (m, 1H), 1.56–1.73 (m, 6H), 2.19–2.23 (m, 2H), 2.25 (s, 3H), 2.42 (m, 1H), 2.62–2.73 (m, 2H), 3.11–3.19 (m, 1H), 3.50–3.72 (m, 2H), 4.10 (m, 1H), 4.45 (m, 1H), 5.89 (s, 1H), 6.77–6.87 (m, 3H), 7.00 (d, J=8.65 Hz, 1H), 7.43–7.51 (m, 3H), 7.72–7.80 (m, 3H), 7.88 (s, 1H).
 IR (KBr): 3329, 2934, 2857, 1646, 1586, 1522, 1457, 1364, 1284, 1223, 1133, 1072, 944, 835, 811, 744, 474 cm$^{-1}$.
 MS(FD): m/e 564 (M$^+$, 100).
 HR MS(FAB) for C$_{32}$H$_{42}$N$_3$O$_4$S: Calcd: 564.2896; Found: 564.2916.

Example 26

[2S-(2R*,2'S*,3'R*)]-1-[2'-Hydroxy-3'-phenylmethyl-4'-aza- 5'-oxo-5'-(2"-methyl-3"-hydroxyphenyl)pentyl]-4-(pyrid-3'''-ylmethyl)piperazine- 2-N-t-butylcarboxamide The titled compound was prepared substantially in accordance with the procedure detailed in Example 1, using 65 mg (0.148 mmol) of the subtitled compound of Preparation 5E, 22.5 mg (0.148 mmol) of the subtitled compound of Preparation 9C, 30.5 mg (0.148 mmol) of DCC, and 20 mg (0.148 mmol) of HOBT.H$_2$O in 5 mL of tetrahydrofuran. The resultant crude material was purified using radial chromatography (1 mm plate; eluent of 3% methanol in methylene chloride) to provide 64 mg of a white foam.
 Yield: 75%.
 $^1$H NMR (CDCl$_3$): δ1.33 (s, 9H), 1.86 (s, 3H), 2.30 (m, 1H), 2.49–2.98 (m, 11H), 3.33 (m, 1H), 3.46 (m, 1H), 4.02 (m, 1H), 4.46 (m, 1H), 6.29 (d, J=9.16 Hz, 1H), 6.46 (d, J=7.23 Hz, 1H), 6.73 (d, J=7.79 Hz, 1H), 6.83 (t, J=7.84 Hz, 1H), 7.17–7.31 (m, 7H), 7.60 (m, 1H), 7.95 (br.s, 1H), 8.50–8.55 (m, 2H).
 MS(FD): m/e 574 (M$^+$, 100).
 HR MS(FAB): m/e for C$_{33}$H$_{44}$N$_5$O$_4$: Calcd: 574.3393; Found: 574.3373.

Example 27

[3S-(3R*,4aR*,8aR8*,2'S*,3'R*)]-2-[2'-Hydroxy-3'-phenylmethyl- 4'-aza-5'-oxo-5'-(2"-ethyl-3"-hydroxyphenyl)pentyl]decahydroisoquinoline- 3-N-t-butylcarboxamide monomesylate salt To a cold (0° C.) solution of 35.1 mg (0.064 mmol) of the titled compound of Example 3 in 2 mL of anhydrous methylene chloride, was added dropwise 134 μL (0.067 mmol) of a 0.5M solution of methanesulfonic acid in methylene chloride. The resulting reaction was reduced to dryness under reduced pressure (0.2–0.1 Torr) to provide 38 mg (crude) of a light yellow foam.
 Yield: 90%.
 $^1$H NMR (CD$_3$OD): δ0.91 (t, J=7.39, 3H), 1.29 (s, 9H), 1.30–3.20 (m, 21H), 4.00–4.40 (m, 2H), 6.47 (d, J=7.30 Hz, 1H), 6.73 (d, J=7.78 Hz, 1H), 6.91 (t, J=7.78 Hz, 1H), 7.15–7.32 (m, 5H).

Example 28

[3S-(3R*,4aR*,8aR*,2'S*,3'R*)]-2-[2'-Hydroxy-3'-phenylmethyl- 4'-aza-5'-oxo-5'-(2"-methyl-3"-hydroxyphenyl)pentyl]decahydroisoquinoline- 3-N-t-butylcarboxamide monomesylate salt The titled compound was prepared substantially in accordance with the procedure detailed in Example 27, using 125 mg (0.23 mmol) of the titled compound of Example 13 in 5 mL of anhydrous methylene chloride, and 240 μL (0.24 mmol) of a 1.0M solution of methanesulfonic acid in methylene chloride to provide 136 mg (crude) of an off-white foam.
 Yield: 95%
 $^1$H NMR (CD$_3$OD): δ1.12 (s, 9H), 1.10–2.20 (m, 16H), 2.60–2.75 (m, 4H), 3.10–3.50 (m, 6H), 3.60–3.70 (m, 1H), 3.90–4.30 (m, 3H), 6.53 (d, J=7.35 Hz, 1H), 6.55 (t, J=7.87 Hz, 1H), 6.89 (t, J=7.82 Hz, 1H).

Example 29

[3S-(3R*,4aR*,8aR*,2'S*,3'S*)]-2-[2'-Hydroxy-3'-phenylthiomethyl-4'-aza-5'-oxo-5'-(2"-methylphenyl)pentyl] decahydroisoquinoline-3-N-t-butylcarboxamide The titled compound was prepared substantially in accordance with the procedure detailed in Example 1, using 15 mg (0.034 mmol) of the subtitled compound of Preparation 8G, 4.7 mg (0.034 mmol) of o-toluic acid, 7.13 mg (0.034 mmol) of DCC, and 4.7 mg (0.034 mmol) of HOBT.H$_2$O in 2.5 mL of tetrahydrofuran. The resultant material was purified using radial chromatography (1 mm plate; eluent 10% acetone in methylene chloride) to provide 16 mg of a white foam.
 Yield: 84%.
 $[\alpha]_D$ −80.00 (c=0.15).
 $^1$H NMR (CDCl$_3$): δ1.04 (s, 9H), 1.08–1.80 (m, 11H), 1.93 (m, 3H), 2.22 (m, 4H), 2.44 (m, 1H), 2.49 (s, 3H), 2.58 (m, 1H), 2.94 (m, 1H), 3.47 (m, 1H), 3.84 (m, 1H), 4.03 (m, 1H), 4.50 (m, 1H), 5.45 (br.s, 1H), 7.12–7.32 (m, 7H), 7.45 (m, 2H), 7.51 (d, J=7.51 Hz, 1H).
 IR (KBr): 3327, 2928, 2852, 1627, 1574, 1535, 1481, 1364, 1311, 1275, 1225, 1088, 737 cm$^{-1}$.
 HR MS(FAB) for C$_{32}$H$_{46}$N$_3$O$_3$S: Calcd: 552.3260; Found: 552.3272.

Example 30

[3S-(3R*,4aR*,8aR*,2'S*,3'S*)]-2-[2'-Hydroxy-3'-phenylthiomethyl-4'-aza-5'-oxo-5'-[3"-methyl-pyrid-4"-yl)]pentyl]decahydroisoquinoline- 3-N-t-butylcarboxamide The titled compound was prepared substantially in accordance with the procedure detailed in Example 1, using 15 mg (0.034 mmol) of the subtitled compound of Preparation 8G, 6.69 mg (0.048 mmol) of the titled compound of Preparation 19, 7.13 mg (0.034 mmol) of DCC, and 4.7 mg (0.034 mmol) of HOBT.H₂O in 1.5 mL of tetrahydrofuran and 1 mL of dimethylformamide. The resultant material was purified using radial chromatography (1 mm plate; gradient eluent of 3–5% methanol in methylene chloride) to provide 10 mg of a white foam.

Yield: 52%.

$[\alpha]_D$ –95.65 (c=0.115).

$^1$H NMR (CDCl₃): δ1.00 (s, 9H), 1.20–1.77 (m, 12H), 1.99 (m, 1H), 2.17 (m, 2H), 2.44 (m, 5H), 2.92 (m, 1H), 3.41 (m, 1H), 3.84 (m, 1H), 4.13 (m, 1H), 4.56 (m, 1H), 5.39 (s, 1H), 7.20–7.46 (m, 6H), 7.75 (d, J=8.94 Hz, 1H), 8.46 (m, 2H).

IR (KBr): 3307, 2925, 2860, 1653, 1542, 1481, 1439, 1391, 1365, 1281, 1224, 1058, 1041, 738, 691, 669 cm$^{-1}$.

HR MS(FAB) for $C_{31}H_{45}N_4O_3S$: Calcd: 553.3212; Found: 553.3222.

Example 31

[3S-(3R*,4aR*,8aR*,2'S*,3'S*)]-2-[2'-Hydroxy-3'-phenylthiomethyl-4'-aza-5'-oxo-5'-(quinolin-5"-yl)pentyl]decahydroisoquinoline-3-N-t-butylcarboxamide The titled compound was prepared substantially in accordance with the procedure detailed in Example 1, using 15 mg (0.034 mmol) of the subtitled compound of Preparation 8G, 6.0 mg (0.034 mmol) of the titled compound of Preparation 20, 7.13 mg (0.034 mmol) of DCC, and 4.7 mg (0.034 mmol) HOBT.H₂O in 2 mL of tetrahydrofuran. The resultant material was purified using radial chromatography (1 mm plate; gradient eluent of 3–5% methanol in methylene chloride) to provide 15 mg of a white foam.

Yield: 74%.

$[\alpha]_D$ –99.50 (c=0.201).

$^1$H NMR (CDCl₃): δ0.74 (s, 9H), 1.15–1.79 (m, 12H), 1.97 (m, 1H), 2.17 (m, 2H), 2.36 (m, 1H), 2.54 (m, 1H), 2.90 (m, 1H), 3.45 (m, 1H), 3.99 (m, 1H), 4.16 (m, 1H), 4.62 (m, 1H), 5.29 (s, 1H), 7.18–7.32 (m, 3H), 7.40–7.50 (m, 3H), 7.70 (m, 1H), 7.89 (m, 2H), 8.17 (m, 1H), 8.91 (m, 2H).

IR (KBr): 3299, 2923, 2862, 1644, 1546, 1481, 1439, 1390, 1327, 1279, 1222, 1207, 1037, 810, 735, 689 cm$^{-1}$.

HR MS(FAB) for $C_{34}H_{45}N_4O_3S$: Calcd: 589.3212; Found: 589.3237.

Example 32

[3S-(3R*,4aR*,8aR*,2'S*,3'S*)]-2-[2'-Hydroxy-3'-phenylthiomethyl-4'-aza-5'-oxo-5'-(1",2",3",4"-tetrahydroquinolin-5"-yl)pentyl]decahydroisoquinoline- 3-N-t-butylcarboxamide The titled compound was prepared substantially in accordance with the procedure detailed in Example 1, using 18 mg (0.04 mmol) of the subtitled compound of Preparation 8G, 7.38 mg (0.04 mmol) of the titled compound of Preparation 21, 8.56 mg (0.04 mmol) of DCC, and 5.61 mg (0.04 mmol) of HOBT.H₂O in 2 mL of tetrahydrofuran. The resultant material was purified using radial chromatography (1 mm plate; gradient eluent of 3–5% methanol in methylene chloride) to provide 12 mg of a white foam.

Yield: 50%.

$[\alpha]_D$ –98.59 (c=0.142).

$^1$H NMR (CDCl₃): δ1.13 (s, 9H), 1.14–2.04 (m, 15H), 2.19 (m, 2H), 2.45 (m, 1H), 2.57 (m, 1H), 2.75 (m, 1H), 2.90–3.09 (m, 2H), 3.26 (m, 2H), 3.44 (m, 2H), 3.75 (m, 1H), 4.01–4.14 (m, 2H), 4.42 (m, 1H), 5.56 (s, 1H), 6.49 (d, J=7.96 Hz, 1H), 6.80 (d, J=7.40 Hz, 1H), 6.93 (t, J=7.72 Hz, 1H), 7.08 (d, J=8.39 Hz, 1H), 7.18 (m, 1H), 7.27 (m, 2H), 7.42 (d, 2H).

IR (KBr): 3327, 2928, 2852, 1629, 1590, 1519, 1481, 1449, 1364, 1310, 1275, 1229, 1087, 738, 690 cm$^{-1}$.

HR MS(FAB) for $C_{34}H_{49}N_4O_3S$: Calcd: 593.3525; Found: 593.3552.

Example 33

[2S-(2R*,2'S*,3'S*)]-1-[2'-Hydroxy-3'-phenylthiomethyl-4'-aza- 5'-oxo-5'-(1",2",3",4"-tetrahydroquinolin-5"-yl)pentyl]-4-(pyrid- 3'"-ylmethyl)piperazine-2-N-t-butylcarboxamide To a cooled (–10° C.) solution containing 45 mg (0.10 mmol) of the subtitled compound of Preparation 6B, 18 mg (0.10 mmol) of 1,2,3,4-tetrahydroquinoline-5-carboxylic acid, 30 mg (0.30 mmol) of triethylamine, and 14 mg (0.10 mmol) of HOBT.H₂O in 2 mL of anhydrous tetrahydrofuran, was added 22 mg (0.11 mmol) of DCC. The resultant reaction mixture was stirred for approximately 24 hours at room temperature and then concentrated under reduced pressure to provide a residue. This residue was redissolved in ethyl acetate, and filtered through celite. The filtrate was then extracted sequentially with saturated sodium bicarbonate (twice), brine, dried over sodium sulfate, filtered and concentrated under reduced pressure. The crude material was purified using radial chromatography (1 mm plate; gradient eluent of 2.5–5% methanol in methylene chloride) to provide 33 mg of an off-white foam.

Yield: 62%.

$^1$H NMR (CDCl₃): δ1.29 (s, 9H), 1.79–1.97 (m, 2H), 2.26–3.00 (m, 11H), 3.20–3.50 (m, 9H), 3.95–4.05 (m, 1H), 4.23–4.35 (m, 1H), 6.43–6.62 (m, 2H), 6.89 (t, J=7.8 Hz, 1H), 7.12–7.35 (m, 6H), 7.41 (d, J=7.7 Hz, 2H), 7.57–7.70 (m, 2H), 8.50–8.58 (m, 2H).

MS(FD): m/e 631 (M$^+$, 100).

Example 34

[2S-(2R*,2'S*,3'S*)]-1-[2'-Hydroxy-3'-phenylthiomethyl-4'-aza- 5'-oxo-5'-(quinolin-5"-yl)pentyl]-4-(pyrid-3'"-ylmethyl)piperazine-2-N-t-butylcarboxamide The titled compound was isolated from Example 33 Yield: 13 mg of an off-white foam.

$^1$H NMR (CDCl₃): δ1.18 (s, 9H), 2.27–2.90 (m, 9H), 3.17–3.60 (m, 5H), 4.07–4.19 (m, 1H), 4.40–4.55 (m, 1H), 4.75–4.95 (m, 1H), 6.90–7.68 (m, 11H), 8.16 (d, J=8.1 Hz, 1H), 8.48–8.60 (m, 2H), 8.80 (d, J=8.4 Hz, 1H), 8.89–8.97 (m, 1H).

MS(FD): m/e 527 (M$^+$, 100).

Example 35

[2S-(2R*,2'S*,3'S*)]-1-[2'-Hydroxy-3'-phenylthiomethyl-4'-aza- 5'-oxo-5'-[3"-methyl-pyrid-4"-yl)]pentyl]-4-(pyrid-3'"-ylmethyl)piperazine-2-N-t-butylcarboxamide The titled compound was prepared substantially in accordance with the procedure detailed in Example 1, using 20.3 mg (0.148 mmol) of the titled compound of Preparation 19, 70 mg (0.148 mmol) of the subtitled compound of Preparation 19, 31 mg (0.148 mmol) of DCC, and 20 mg (0.148 mmol) of HOBT.H$_2$O in tetrahydrofuran containing 62 mL of triethylamine. The resultant material was purified using radial chromatography (2 mm plate; gradient eluent of 2.5–15% methanol in methylene chloride) to provide 48 mg of a white foam.

Yield: 55%.

$^1$H NMR (CDCl$_3$): δ1.23 (s, 9H), 2.30–2.90 (m, 12H), 3.16–3.50 (m, 5H), 4.02–4.10 (m, 1H), 4.30–4.42.41 (m, 1H), 4.85 (br.s, 1H), 6.90–7.60 (m, 10H), 8.38–8.57 (m, 3H).

MS(FAB): m/e 591.4 (M$^+$, 100).

Example 36

[3S-(3R*,4aR*,8aR*,2'S*,3'S*)]-2-[2'-Hydroxy-3'-phenylmethyl- 4'-aza-5'-oxo-5'-[2"-methyl-3"-N-(methylsulfonyl)amino-phenyl)]pentyl]decahydroisoquinoline-3-N-t-butylcarboxamide The titled compound was prepared substantially in accordance with the procedure detailed in Example 1, using 70 mg (0.17 mmol) of the subtitled compound of Preparation 1B, 40 mg (0.17 mmol) of the titled compound of Preparation 22, 35 mg (0.17 mmol) of DCC, and 23 mg (0.17 mmol) of HOBT.H$_2$O in 2 mL of anhydrous tetrahydrofuran. The resultant material was purified using radial chromatography (2 mm plate; gradient eluent of 1–5% methanol in methylene chloride) to provide 72 mg of an off-white solid.

Yield: 69%.

$^1$H NMR (CDCl$_3$): δ1.14 (s, 9H), 1.19–2.38 (m, 19H), 2.50–2.70 (m, 2H), 2.92–3.06 (m, 4H), 3.43–3.55 (m, 1H), 4.01–4.10 (m, 1H), 4.58–4.70 (m, 1H), 5.66 (s, 1H), 6.37 (br.s, 1H), 6.82–6.93 (m, 2H), 7.10–7.39 (m, 6H), 7.48 (d, J=8.16 Hz, 1H).

IR (KBr): 3691, 3600–3300 (br.), 2929, 2866, 1672, 1603, 1513, 1455, 1393, 1368, 1327, 1277, 1154, 1047, 972, 909, 877 cm$^{-1}$.

MS(FD): m/e M$^+$, 100).

Example 37

[3S-(3R*,4aR*,8aR*,2'S*,3'S*)]-2-[2'-Hydroxy-3'-phenylmethyl- 4'-aza-5'-oxo-5'-[(1",2",3",4"-tetrahydroquinolin-5"-yl)]pentyl]decahydroisoquinoline-3-N-t-butylcarboxamide The titled compound was prepared substantially in accordance with the procedure detailed in Example 1, using 18.5 mg (0.046 mmol) of the subtitled compound of Preparation 1B, 8.14 mg (0.046 mmol) of the titled compound of Preparation 20, 9.48 mg (0.046 mmol) of DCC, and 6.21 mg (0.046 mmol) of HOBT.H$_2$O in 2 mL of anhydrous tetrahydrofuran. The resultant material was purified using radial chromatography (1 mm plate; gradient eluent of 2–5% methanol in methylene chloride) to provide 11 mg of a foam.

Yield: 43%.

$^1$H NMR (CDCl$_3$): δ1.20 (s, 9H), 1.25–2.02 (m, 15H), 2.28 (m, 2H), 2.46–2.70 (m, 4H), 2.99 (m, 2H), 3.21 (m, 1H), 3.35 (m, 1H), 3.98 (m, 1H), 4.49 (m, 1H), 5.75 (br.s, 1H), 6.38 (m, 3H), 6.83 (t, 1H), 7.21–7.33 (m, 5H).

Example 38

[3S-(3R*,4aR*,8aR*,2'S*,3'S*)]-2-[2'-Hydroxy-3'-phenylthiomethyl-4'-aza-5'-oxo-5'-[6"-methyl-(1",2",3",4"-tetrahydroquinolin-5"-yl)]pentyl] decahydroisoquinoline-3-N-t-butylcarboxamide The titled compound was prepared substantially in accordance with the procedure detailed in Example 1, using 15 mg (0.035 mmol) of the subtitled compound of Preparation 8G, 6.5 mg (0.035 mmol) of 6-methyl-1,2,3,4-tetrahydro-5-quinoline carboxylic acid, 7.15 mg (0.035 mmol) of DCC, and 4.7 mg (0.035 mmol) of HOBT.H$_2$O in 2 mL of tetrahydrofuran and 1 mL of dimethylformamide. The resultant material was purified using radial chromatography (1 mm plate; gradient eluent of 3–5% methanol in methylene chloride) to provide 12.5 mg of a white solid.

Yield: 60%.

HR MS(FAB) for C$_{35}$H$_{47}$N$_4$O$_3$S: Calcd: 603.3369; Found: 603.3384.

Example 39

[3S-(3R*,4aR*,8aR*,2'S*,3'S*)]-2-[2'-Hydroxy-3'-phenylthiomethyl-4'-aza-5'-oxo-5'-[2",6"-dimethyl-3"-hydroxyphenyl] pentyl]decahydroisoquinoline-3-N-t-butylcarboxamide The titled compound was prepared substantially in accordance with the procedure detailed in Example 1, using 20 mg (0.046 mmol) of the subtitled compound of Preparation 8G, 11.53 mg (0.0694 mmol) of 2,6-dimethyl-3-hydroxy benzoic acid, 9.54 mg (0.046 mmol) of DCC, and 6.25 mg (0.046 mmol) of HOBT.H$_2$O in 3 mL of tetrahydrofuran. The resultant material was purified using radial chromatography (1 mm plate; eluent of 4% methanol in methylene chloride) to provide 14 mg of a white solid.

Yield: 52%.

HR MS(FAB) for C$_{33}$H$_{48}$N$_3$O$_4$S: Calcd: 582.3375; Found: 582.3373.

As noted above, the compounds of the present invention are useful for inhibiting HIV protease, which is an enzyme associated with viral component production and assembly. An embodiment of the present invention is a method of treating or preventing HIV infection comprising administering to a primate in need thereof an effective amount of a compound of formula I or a pharmaceutically acceptable salt thereof. Another embodiment of the present invention is a method of treating or preventing AIDS comprising administering to a primate in need thereof an effective amount of a compound of formula I or a pharmaceutically acceptable salt thereof. A further embodiment of the present invention is a method of inhibiting HIV replication comprising administering to an HIV infected cell, a cell susceptible to HIV infection or a primate in need, thereof, an effective amount of a compound of formula I or a pharmaceutically acceptable salt thereof.

The term "effective amount" as used herein, means an amount of a compound of formula I which is capable of inhibiting the HIV protease mediated viral component production and assembly. The HIV protease inhibition contemplated by the present method includes either therapeutic or prophylactic treatment, as appropriate. The specific dose of compound administered according to this invention to obtain therapeutic or prophylactic effects will, of course, be determined by the particular circumstances surrounding the case, including, for example, the compound administered, the route of administration, the condition being treated and the individual being treated. A typical daily dose (administered in single or divided doses) will contain a dosage level of from about 0.01 mg/kg to about 50 mg/kg of body weight of an active compound of this invention. Preferred daily doses generally will be from about 0.05 mg/kg to about 20 mg/kg and ideally from about 0.1 mg/kg to about 10 mg/kg.

The compounds can be administered by a variety of routes including oral, rectal, transdermal, subcutaneous, intravenous, intramuscular and intranasal. The compounds of the present invention are preferably formulated prior to administration. Therefore, another embodiment of the present invention is a pharmaceutical formulation comprising an effective amount of a compound of formula I or a pharmaceutically acceptable salt thereof and a pharmaceutically acceptable carrier, diluent or excipient therefor.

The active ingredient in such formulations comprises from 0.1% to 99.9% by weight of the formulation. By "pharmaceutically acceptable" it is meant that the carrier, diluent or excipient is compatible with the other ingredients of the formulation and not deleterious to the recipient thereof.

The present pharmaceutical formulations can be prepared by known procedures using known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

The following formulation examples are illustrative only and are not intended to limit the scope of the invention in any way. The term "active ingredient" represents a compound of formula I or a pharmaceutically acceptable salt thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
| --- | --- |
| Active ingredient | 0.25 |
| Methanol | 25.75 |
| Propellent 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

|  | Quantity (mg/tablet) |
| --- | --- |
| Active ingredient | 60 |
| Starch | 45 |
| Microcrystalline cellulose | 35 |
| Polyvinylpyrrolidone (as 10% solution in water) | 4 |
| Sodium carboxymethyl starch | 4.5 |
| Magnesium stearate | 0.5 |
| Talc | 1 |
| Total | 150 |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

|  | Quantity (mg/capsule) |
| --- | --- |
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 mL dose, are made as follows:

| Active ingredient | 50 mg |
|---|---|
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1,000 mL |

The solution of the above ingredients generally is administered intravenously to a subject at a rate of 1 mL per minute.

The following experiment (Fluorescence HIV-1 Protease Inhibitor Assay) was carried out to demonstrate the ability of the compounds of the present invention to inhibit HIV protease.

As used herein, the abbreviations are defined as follows:
BSA—bovine serum albumin
BOC—t-butoxycarbonyl
BrZ—2-bromobenzyloxycarbonyl
2-ClZ—2-chlorobenzyloxycarbonyl
DCC—dicyclohexylcarbodiimide
DIEA—diisopropylethylamine
DTT—dithiothreitol
EDTA—ethylenediaminetetraacetic acid
FITC—fluorescein isothiocarbamyl
HEPES—4-(2-hydroxyethyl)-1-piperazineethanesulfonic acid
MES—4 morpholineethanesulfonic acid
PAM—phenylacetimidomethyl
TAPS—3-[tris(hydroxymethyl)methyl]amino-1-sulfonic acid
TRIS—tris(hydroxymethyl)aminomethane
TOS—p-toluenesulfonyl (tosyl)

I. Preparation of Protease and Gag Fractions

A. Culture of E. coli K12 L507/pHP10D

Lyophils of E. Coli K12 L507/pHP10D were obtained from the Northern Regional Research Laboratory, Peoria, Ill. 61604, under the accession number NRRL B-18560 (deposited Nov. 14, 1989). The lyophils were decanted into tubes containing 10 mL LB medium (10 g Bacto-tryptone, 5 g Bacto-yeast extract, and 10 g aqueous sodium chloride per liter; the pH was adjusted to 7.5 and incubated at 32° C., overnight).

A small portion of the overnight culture was placed on LB-agar (LB medium with 15 g/L Bacto-agar) plates containing 12.5 µg/mL tetracycline in a manner so as to obtain a single colony isolate of E. coli K12 L507/pHP10D. The single colony obtained was inoculated into 10 mL of LB medium containing 12.5 µg/mL tetracycline and incubated overnight at 32° C. with vigorous shaking. The 10 mL overnight culture was inoculated into LB medium containing 12.5 µg/mL tetracycline and incubated at 32° C. with vigorous shaking until the culture reached mid-log phase.

B. Culture of E. coli K12 L507/pHGAG

Lyophils of E. coli K12 L507/pHGAG were obtained from the NRRL under the accession number NRRL B-18561 (deposited Nov. 14, 1989). A purified colony of E. coli K 12 L507/pHGAG was isolated, and used as an inoculum for a culture which was grown to mid-log phase in substantial accordance with the teaching of Step A, above, for E. Coli K12 L507/pHP10D.

C. Preparation of Protease Fraction

A culture of E. coli K12 L507/pHP10D was grown to mid-log phase at 32° C. in LB media containing 12.5 µg/mL tetracycline. The cultivation temperature was quickly elevated to 40° C. to induce gene expression, and the cells were allowed to grow for 2.5 hours at this temperature before the culture was quickly chilled on ice. The cells were centrifuged and the cell pellet was resuspended in 20 mL of 50 mmol MES buffer (pH 6.0) containing 1 mmol EDTA, 1 mmol DTT, 1 mmol PMSF and 10% glycerol ("Buffer A"). Cells were lysed by sonication using a Fischer Model 300 Dismembrator and a microtip probe. Following centrifugation at 27,000×g, the supernatant was diluted to a total volume of 60 mL with Buffer A and loaded onto a 2.0×19 cm QAE-Sepharose column (1 mL/min, 4° C.), that had been equilibrated in Buffer A. The column was washed isocratically for 180 min and then eluted with a gradient eluent of 0–1.0M aqueous sodium chloride in Buffer A over 120 min. Enzymatic activity was measured by HPLC using the synthetic peptide Ser-Gln-Asn-Tyr-Pro-Ile-Val as described in Margolin et al., Biochem. Biophys. Res. Common., 167, 554–560 (1990); the production of the p1 peptide (Ser-Gln-Asn-Tyr) was measured.

The active fractions were combined, adjusted to pH 1.2M in ammonium sulfate, and applied to a 2.0×18 cm hexyl agarose column that had been equilibrated in Buffer A containing 1.2M ammonium sulfate. The sample was loaded at a flow rate of 1 mL/min at 4° C., washed with the equilibration buffer for 240 min (1 mL/min) and then eluted using a reverse linear gradient of 1.2–0M ammonium sulfate in Buffer A for 120 min at the same flow rate. The column was then washed isocratically in Buffer A for 120 min.

The active fractions were combined, concentrated to 10 mL using an Amicon stirred cell with a YM-10 membrane and then applied to a MonoS cation exchange column (1.0×10 cm) that had been equilibrated in Buffer A. The sample was loaded at a flow rate of 1 mL/min at 25° C. After washing isocratically for 30 min, the protease was eluted using a linear gradient of 0–0.45M aqueous sodium chloride in Buffer A over 40 min. The column was washed isocratically in Buffer A containing 0.45M aqueous sodium chloride for 30 minutes.

The active fractions were combined and concentrated to 200 μL using an Amicon stirred cell and a YM-10 membrane and then the protease was applied to a Superose 6 size exclusion column equilibrated in Buffer A containing 0.1M aqueous sodium chloride. The column was washed isocratically in this buffer at a flow rate of 0.5 ml/min, following which the HIV protease was eluted as a single peak.

QAE-Sepharose, and hexyl agarose were purchased from Sigma Chemical Company. Superose 6 and MonoS were were purchased from Pharmacia. Buffers and reagents were obtained from Sigma.

D. Preparation of Gag Fraction

In an analogous manner, a culture of *E. coli* K12 507/pHGAG was grown to mid-log phase at 32° C. then shifted to 40° C. for about 4 to 5 hours. The culture was chilled on ice and centrifuged, then the pellet was resuspended in 8 mL lysis buffer containing 5 mg/mL lysozyme. Lysis buffer was comprised of 50 mM Tris-HCl (pH 7.8), 5 mM EDTA, 1 mM DTT, 100 mM NaCl, 1 μg/mL E64 and 2 μg/mL aprotinin. The culture was incubated about 30 to 60 minutes at 4° C., then briefly sonicated in a Branson® Cell Disrupter at 60% power, for three 20 second bursts with chilling between each burst. The culture was then centrifuged at 15,000×g. The supernatant, which contains the unprocessed gag protein, was partially purified by size exclusion chromatography on a Sephadex G-50 column and stored at −20° C. in 50% glycerol and lysis buffer.

II. Preparation of Substrate: $N^\alpha$-Biotin-Gly-Ser-Gln-Asn-Tyr-Pro-Ile-Val-Gly-Lys($N^\epsilon$-FITC)-OH A. Preparation of the amino-terminal biotinylated peptide The protected peptide-resin $N^\alpha$-Boc-Gly-Ser-Gln-Asn-Tyr(BrZ)-Pro-Ile-Val-Gly-Lys(2-ClZ)-OCH$_2$-PAM-resin was synthesized on an Advanced Chemtech Model 200 peptide synthesizer at 1.5 mmol scale using the standard double-couple protocol. The amino terminal t-Boc group was removed with 50% trifluoroacetic acid in methylene chloride and the resulting resin neutralized with 5% diisopropylethylamine (DIEA) in methylene chloride. Then, 1.1 g (4.5 mmol) of biotin in 20 mL of dimethylsulfoxide was added to the peptide resin, followed by 4.5 mmol of dicyclohexylcarbodiimide (DCC) in 9 mL of methylene chloride. The resulting reaction mixture was diluted to 40 mL total volume using 11 mL of methylene chloride, and then allowed to react for approximately 5 hours. The reaction solution was concentrated, the resin washed sequentially with dimethylsulfoxide, dimethylformamide and methylene chloride and then neutralized with 5% DIEA in methylene chloride. This reaction was repeated twice, with the reaction time being extended to 12 hours per reaction. Ninhydrin analysis of the resin indicated complete reaction of the biotin with the glycine amine group. The final peptide resin was washed extensively with dimethylformamide and methylene chloride and dried to provide 4.3 g (98%).

B. Deprotection

The peptide was deprotected and cleaved from the resin using 50 mL of a hydrofluoric acid/m-cresol solution, 0° C., 1 hour. After removal of the hydrofluoric acid by vacuum distillation, the m-cresol was extracted from the reaction mixture using 100 mL of diethylether. The peptide was then solubilized in 50% aqueous acetic acid, frozen and lyophilized to provide 2.14 g.

C. Purification

The crude peptide, biotinylated at the amino terminal, was dissolved in 200 mL of a 5% acetonitrile in water solution containing 0.1% trifluoroacetic acid and then filtered through a 0.22 micron filter. The resulting solution was applied to a 2.2×25 cm. reverse phase column of octadecylsilica (Vydac C-18) which had been equilibrated with the same buffer. The peptide was eluted using an 855 minute linear gradient of 7.5–25% acetonitrile, at 2 mL/minute, with collection of fractions. These fractions were analyzed using Analytical HPLC was performed on a 4.6×250 mm Vydac C-18 column using similar buffer conditions. The fractions containing the desired material were combined, frozen and lyophilized to provide 1.206 g (62%).

Amino acid analysis of the isolated biotinylated peptide gave the following ratios: Asn 1.1; Ser 0.96; Gln 1.1; Pro 1.1; Gly 2.1; Val 0.80; Ile 0.78; Tyr 1.1; Lys 1.1; in agreement with theory. Fast-atom bombardment mass spectrometry gave a molecular ion mass peak of 1288, in agreement with theory.

D. Labeling

The purified biotinylated peptide was then labeled with a fluorescent marker at the C-terminal end for use in the Pandex assay. First, the biotinylate peptide (1.206 g, 0.936 mmol) was dissolved in 100 mL of 0.1M sodium borate, pH 9.5. Then, a solution of 3 g (7.7 mmol) of fluorescein isothiocyanate in 15 mL of dimethylsulfoxide was added to the reaction mixture in 10 equal portions over two hours. The resulting mixture was allowed to react for one hour after the final addition. The solution was adjusted to pH 3 using 5N hydrochloric acid, resulting in the formation of a precipitate which was removed by centrifugation.

The peptide solution was then adjusted to pH 7.8 using 5N sodium hydroxide and then diluted to 200 mL by the addition of 0.1M ammonium acetate, pH 7.5. The resulting solution was then filtered through a 0.22 micron filter and loaded onto a 2.2×25 cm column of Vydac C-18 which had been equilibrated with of 5% acetonitrile in 0.1M ammonium acetate (pH 7.5). The peptide was eluted from the column using an 855 minute linear gradient of 5–25% acetonitrile, at 2 mL/minute, with collection of fractions. Analytical HPLC was used to analyze the fractions. The fractions containing the desired product were then combined, frozen and lyophilized to provide 190.2 mg (12%).

Amino acid analysis of the purified peptide gave the following: Asn 1.1; Ser 1.0; Gln 1.1; Pro 1.1; Gly 2.1; Val 0.8; Ile 0.8; Tyr 1.1; Lys 1.0; in agreement with theory. Fast-atom bombardment mass spectrometry gave amolecular ion mass peak of 1678, in agreement with theory.

E. Fluorescence HIV-1 Protease Inhibitor Assay

The following buffers and solutions are used in the Fluorescence HIV-1 Protease Inhibitor Assay:

| | |
|---|---|
| MES-ALB Buffer: | 0.05$\underline{M}$ 4-morpholuneethane sulfonic acid, pH 5.5 |
| | 0.02$\underline{M}$ NaCl |
| | 0.002$\underline{M}$ EDTA |
| | 0.001$\underline{M}$ DTT |
| | 1.0 mg/mL BSA |
| TBSA Buffer: | 0.02$\underline{M}$ TRIS |
| | 0.15$\underline{M}$ NaCl |
| | 1.0 mg/mL BSA |

| | |
|---|---|
| Avidin Coated Beads Solution: | 0.1% solution of Fluoricon Avidin Assay Particles (Avidin conjugated to solid polystyrene beads, 0.6–0.8 microns in diameter in TBSA Buffer |
| Enzyme Solution: | 27 IU/mL of purified HIV-1 protease in MES-ALB buffer (1 IU equals the amount of enzyme required to hydrolyze 1 μmole of substrate per minute at 37° C. |

To each well of a round bottom, 96-well plate is added 20 μL of the Enzyme Solution followed by 10 μL of the compound to be evaluated in a 20% aqueous dimethylsulfoxide solution. Purified HIV-1 protease was obtained as described above. The resulting solution is incubated for one hour at room temperature and then 20 μL of a solution containing the substrate, prepared above, in MES-ALB buffer (1.5 μL/mL) is added to each well. The solutions are then incubated for 16 hours at room temperature and then each well is diluted with 150 μL of MES-ALB buffer.

To each well of a second round bottom, 96-well Pandex plate is added 25 uL of the Avidin Coated Beads Solution. Then, to each well is added 25 μL of the diluted incubation solutions, prepared above. The solutions are mixed thoroughly and the plates are loaded into a Pandex® machine, washed, evacuated and read. Sample detection was performed by excitation at 485 nm, reading the resulting epifluorescence at 535 nm.

The IC$_{50}$ results obtained in the Fluorescence Assay for the compounds of the present invention are set forth below in Table 1. All values have been normalized to a positive control which is [1S-(1R*,4R*,5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-2-quinolinyl carboxamide.

TABLE 1

Inhibitory Activity of Formula I Compounds

| Example No. | Fluorescence Assay IC$_{50}$ in ng/mL |
|---|---|
| Control | 1.0 |
| 1 | 962 |
| 2 | 1083 |
| 3 | 24.2 |
| 4 | 1425* |
| 5 | 2631 |
| 6 | 513* |
| 7 | 255* |
| 8 | 16.4 |
| 9 | 17 |
| 10 | N.T. |
| 11 | 5.1 |
| 12 | 8.3* |
| 13 | 346 |
| 14 | 101 |
| 15 | 377 |
| 16 | 329 |
| 17 | 269* |
| 18 | 67.2* |
| 19 | 0.32 |
| 20 | 6.5 |
| 21 | 9.4 |
| 22 | 0.73 |
| 23 | 0.25 |
| 24 | 5.8 |

TABLE 1-continued

Inhibitory Activity of Formula I Compounds

| Example No. | Fluorescence Assay IC$_{50}$ in ng/mL |
|---|---|
| 25 | 3.2 |
| 26 | 3.1 |
| 27 | N.T. |
| 28 | N.T. |
| 29 | 1.7 |
| 30 | 4.2 |
| 31 | 1.2 |
| 32 | 0.52 |
| 33 | 1.7 |
| 34 | 4.5 |
| 35 | 31.7 |
| 36 | 62 |
| 37 | 27.5 |
| 38 | 15.2 |
| 39 | 5.3 |

N.T. not tested.
*a calculated average

We claim:

1. A compound of formula II

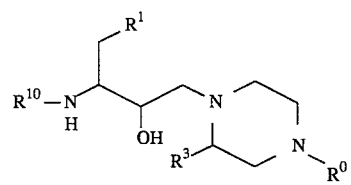

wherein:

$R^1$ is a phenyl or a naphthyl ring which is optionally substituted with halo, hydroxy, or $C_1$–$C_4$ alkoxy;

$R^{10}$ is hydrogen or an amino-protecting group;

$R^0$ is $C_1$–$C_4$ alkyl or —$CH_2$-pyridyl;

$R^3$ is a group having the structure:

1) —C(O)—NR$^4$R$^4$,

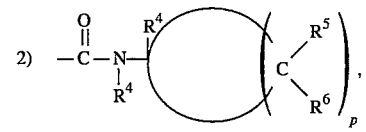

or

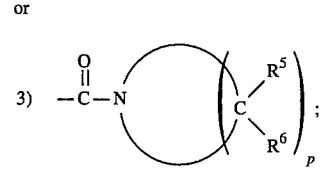

p is 4 or 5;

$R^4$ at each occurrence is independently hydrogen, $C_1$–$C_6$ alkyl or hydroxy($C_1$–$C_4$)alkyl; and $R^5$ and $R^6$ are independently selected from hydrogen, hydroxy, $C_1$–$C_6$ alkyl, $C_1$–$C_6$ alkoxy, or hydroxy($C_1$–$C_4$)alkyl;

or a pharmaceutically acceptable salt thereof.

* * * * *